(12) United States Patent
Gronlund et al.

(10) Patent No.: US 12,377,141 B2
(45) Date of Patent: Aug. 5, 2025

(54) METHOD FOR THE EXPANSION OF HPV IMMUNOGEN SPECIFIC T-CELLS

(71) Applicant: NEOGAP THERAPEUTICS AB, Stockholm (SE)

(72) Inventors: Hans Gronlund, Lidingö (SE); Ola Winqvist, Uppsala (SE)

(73) Assignee: NEOGAP THERAPEUTICS AB, Stockholm (SE)

( * ) Notice: Subject to any disclaimer, the term of this patent is extended or adjusted under 35 U.S.C. 154(b) by 1034 days.

(21) Appl. No.: 17/417,596

(22) PCT Filed: Dec. 24, 2019

(86) PCT No.: PCT/EP2019/087030
§ 371 (c)(1),
(2) Date: Jun. 23, 2021

(87) PCT Pub. No.: WO2020/136210
PCT Pub. Date: Jul. 2, 2020

(65) Prior Publication Data
US 2022/0226457 A1   Jul. 21, 2022

(30) Foreign Application Priority Data
Dec. 24, 2018   (GB) ..................... 1821207

(51) Int. Cl.
| | | |
|---|---|---|
| *A61K 39/12* | (2006.01) | |
| *A61K 40/11* | (2025.01) | |
| *A61K 40/42* | (2025.01) | |
| *A61K 40/46* | (2025.01) | |
| *C12N 5/0783* | (2010.01) | |
| *A61K 39/00* | (2006.01) | |

(52) U.S. Cl.
CPC .............. *A61K 39/12* (2013.01); *A61K 40/11* (2025.01); *A61K 40/428* (2025.01); *A61K 40/46* (2025.01); *C12N 5/0636* (2013.01); *A61K 2039/5258* (2013.01); *A61K 2039/55555* (2013.01); *A61K 2039/892* (2018.08); *C12N 2710/20011* (2013.01); *C12N 2710/20023* (2013.01); *C12N 2710/20034* (2013.01)

(58) Field of Classification Search
CPC ........ A61K 39/12; A61K 40/11; A61K 40/46; A61K 47/6929; C12N 2710/20011; C12N 2710/20034
See application file for complete search history.

(56) References Cited

U.S. PATENT DOCUMENTS

| 11,360,079 B2 | 6/2022 | Grönlund |
| 2004/0224402 A1 | 11/2004 | Bonyhadi et al. |
| 2008/0171059 A1 | 7/2008 | Howland et al. |
| 2016/0058853 A1 | 3/2016 | Sahin et al. |
| 2016/0101170 A1 | 4/2016 | Hacohen et al. |
| 2017/0072051 A1 | 3/2017 | Kaltenboeck et al. |
| 2017/0119668 A1 | 5/2017 | Keselowsky et al. |
| 2020/0140813 A1 | 5/2020 | Grönlund |
| 2022/0381771 A1 | 12/2022 | Grönlund |
| 2023/0310608 A1 | 10/2023 | Grönlund et al. |

FOREIGN PATENT DOCUMENTS

| CN | 104338126 A | * | 2/2015 |
| EP | 2987494 A1 | | 2/2016 |
| EP | 3182125 A1 | | 6/2017 |
| JP | 2014523406 A | | 9/2014 |
| JP | 2016-501870 A | | 1/2016 |
| WO | WO 1992/011030 A1 | | 7/1992 |
| WO | WO 2001/017551 A2 | | 3/2001 |
| WO | WO 2003/093511 A1 | | 11/2003 |
| WO | WO 2005/013896 A2 | | 2/2005 |

(Continued)

OTHER PUBLICATIONS

Bellone, S., et al., 2009, Human papillomavirus type 16 (HPV-16) virus-like particle L1-specfic CD8+ cytotoxic T-lymphocytes (CTLs) are equally effective as E7-specific CD8+ Ctls in killing autologous HPV-16-positive tumor cells in cervical cancer patients . . . , J. Virol. 83(13):6779-6789.*

Bellone, S., et al., Jul. 2009, Human papillomavirus type 16 (HPV-16) virus-like particle L1-specific CD8+ cytotoxic T lymphocytes (CTLs) are equally effective as E7-specific CD8+ CTLs in killing autologous HPV-16-positive tumor cells in cervical cancer patients: Implications for . . . , J. Virol. 83(13):6779-6789.*

Unger, E., et al., Feb. 2017, Laboratory procedure manual: Human papillomavirus in serum-9-plex competitive luminex immunoassay (9-plex-cLIA,), retrieved from web.archive.org/web/w0q70225212457, 8 pages.*

(Continued)

*Primary Examiner* — Jeffrey S Parkin
(74) *Attorney, Agent, or Firm* — Biospark Intellectual Property Law

(57) ABSTRACT

The present invention provides a method for the expansion of HPV immunogen specific T cells, comprising the steps of: i. providing a phagocytosable particle comprising a core and a human papillomavirus (HPV) immunogen tightly associated to the core; wherein the HPV immunogen has an amino acid sequence that corresponds to the amino acid sequence of a HPV protein, or has an amino acid sequence that corresponds to an amino acid sequence of a part of a HPV protein; ii. providing APCs; iii. contacting the phagocytosable particle comprising a core and a HPV immunogen with the APCs from step ii in vitro, and under conditions allowing phagocytosis of the HPV immunogen by the APCs; iv. providing T-cells that have been harvested from a subject; v. contacting the T-cells with the APCs from step iii) in vitro, and under conditions allowing specific activation of HPV immunogen specific T-cells. The invention further provides an expanded population of therapeutically useful T-cells and their use in the treatment or prevention of cancer, particularly HPV positive cancers.

17 Claims, 15 Drawing Sheets

Specification includes a Sequence Listing.

(56) References Cited

FOREIGN PATENT DOCUMENTS

| WO | WO 2008/019366 A2 | 2/2008 |
|---|---|---|
| WO | WO 2009/076099 A1 | 6/2009 |
| WO | WO 2011/053331 A1 | 5/2011 |
| WO | WO 2011/085231 A2 | 7/2011 |
| WO | 2012159643 A1 | 11/2012 |
| WO | WO 2014/082729 A1 | 6/2014 |
| WO | WO 2015/009604 A1 | 1/2015 |
| WO | WO 2016/040900 A1 | 3/2016 |
| WO | WO 2016/053339 A1 | 4/2016 |
| WO | WO 2016/077215 A2 | 5/2016 |
| WO | WO 2016/154544 A1 | 9/2016 |
| WO | WO 2016/187508 A2 | 11/2016 |
| WO | WO 2017/087692 A1 | 5/2017 |
| WO | WO 2017/096304 A1 | 6/2017 |
| WO | WO 2017/102921 A1 | 6/2017 |
| WO | WO 2018/050818 A1 | 3/2018 |
| WO | WO 2018/182495 A1 | 10/2018 |
| WO | WO 2018/234516 A2 | 12/2018 |

OTHER PUBLICATIONS

Luminex Corporation, May 2014, MAGPIX provides equivalent performance to the luminex 100/200 in an HPV vaccination trial, www.luminexcorp.com/download/magpix-provides-equivalent-performance-to-the-luminex-100200-in-an-hpv-vaccination-trial/, 4 pages.*

Perica, K., et al., 2015, Enrichment and Expansion with Nanoscale Artificial Antigen Presenting Cells for Adoptive Immunotherapy, ACSNANO, 9(7):6861-6871.*

Bagarazzi et al., "Immunotherapy Against HPV16/18 Generates Potent TH1 and Cytotoxic Cellular Immune Responses," Science Translational Medicine, Oct. 10, 2012, vol. 4, Issue 155, p. 155ra138.

Bang Laboratories, Inc., "Ask the Particle Doctor," 2011, pp. 1-69.

Bonaccorsi et al., "Acquisition and Presentation of Tumor Antigens by Dendritic Cells," Critical Reviews in Immunology, vol. 35, Issue 5, 2015, pp. 349-364.

Borst et al., "CD4+ T cell help in cancer immunology and immunotherapy," Nature Reviews Immunology, Oct. 2018, vol. 18, pp. 635-647.

Borysiewicz et al., "A recombinant vaccinia virus encoding human papillomavirus types 16 and 18, E6 and E7 proteins as immunotherapy for cervical cancer," Lancet, vol. 347, Issue 9014, Jun. 1996, pp. 1523-1527.

Castle et al., "Exploiting the mutanome for tumor vaccination," Cancer Research, Mar. 2012, vol. 72, Issue 5, pp. 1081-1091.

Cho, N. et al., "A multifunctional core-shell nanoparticle for dendritic cell-based cancer immunotherapy," Nature Nanotechnology, Sep. 11, 2011, vol. 6, pp. 675-682.

Chouhy et al., "Analysis of the genetic diversity and phylogenetic relationships of putative human papillomavirus types," Journal of General Virology, 2013, vol. 94, Issue 11, p. 2480-2488.

Dianzani et al., "Association of Human Papillomavirus Type 11 with Carcinoma of the Penis," Urology, 1998, vol. 51, Issue 6, Jun. 1998, pp. 1046-1048.

Forbes et al., "COSMIC: somatic cancer genetics at high-resolution," Nucleic Acids Research, vol. 45, Issue D1, Jan. 2017, pp. D777-D783.

International Preliminary Report on Patentability, Chapter 1, Patent Cooperation Treaty Application No. PCT/EP2018/066690, Dec. 24, 2019, 13 pages.

International Preliminary Report on Patentability, Chapter 1, Patent Cooperation Treaty Application No. PCT/EP2019/087029, Jun. 16, 2021, 6 pages.

International Preliminary Report on Patentability, Chapter 1, Patent Cooperation Treaty Application No. PCT/EP2019/087030, Jun. 16, 2021, 7 pages.

International Search Report and Written Opinion, Patent Cooperation Treaty Application No. PCT/EP2018/066690, Jan. 15, 2019, 20 pages.

International Search Report and Written Opinion, Patent Cooperation Treaty Application No. PCT/EP2019/087029, Feb. 20, 2020, 12 pages.

Jiang et al., "Role of IL-2 in cancer immunotherapy," Oncoimmunology, 2016, vol. 5, No. 6, e1163462, 10 pages.

Karlsson et al., "Pilot study of sentinel-node-based adoptive immunotherapy in advanced colorectal cancer," Annals of Surgical Oncology, 2010, vol. 17, pp. 1747-1757.

Kreiter et al., "Mutant MHC class II epitopes drive therapeutic immune responses to cancer," Nature, Apr. 3, 20150, vol. 520, pp. 692-696.

Kuai, R., et al., "Designer vaccine nanodiscs for personalized cancer immunotherapy (includes Methods)" with supplementary information, Nature Materials, vol. 16, No. 4, p. 489-498, Apr. 2017 (Apr. 2017), 36 pages.

Kuai, R., et al., "Subcutaneous Nanodisc Vaccination with Neoantigens for Combination Cancer Immunotherapy" with supporting information, Bioconjugate Chemistry, vol. 29, p. 771-775, Feb. 27, 2018 (Feb. 17, 2018), 18 pages.

Lee and Margolin, "Cytokines in cancer immunotherapy," Cancers, 2011, 3(4), 3856-3893.

Li, H. et al., "Alpha-alumina nanoparticles induce efficient autophagy-dependent cross-presentation and potent antitumour response," Nature Nanotechnology, Sep. 18, 2011, vol. 6, pp. 645-650.

Marits et al., "Evaluation of T and B lymphocyte function in clinical practice using a flow cytometry based proliferation assay," Clinical Immunology, vol. 153, Issue 2, Aug. 2014, pp. 332-342.

Motoyama et al., "The role of human papilloma virus in the molecular biology of cervical carcinogenesis," Kobe Journal of the Medical Sciences, 2004, vol. 50, pp. 9-19.

Munoz et al., "Chapter 1: HPV in the etiology of human cancer," Vaccine, vol. 24, Supplement 3, Aug. 21, 2006, pp. S1-S10.

Pan et al., "Altered cell cycle regulation in the lens of HPV-16 E6 or E7 transgenic mice: Implications for tumor suppressor gene function in development," Genes & Development, Jun. 1994, 8(11), pp. 1285-1299.

Pittet et al., "Cutting Edge: Cytolytic Effector Function in Human Circulating CD8+ T Cells Closely Correlates with CD56 Surface Expression," The Journal of Immunology, Feb. 2000, vol. 164, Issue 3, pp. 1148-1152.

Prickett, T.D. et al., "Durable Complete Response from Metastatic Melanoma after Transfer of Autologous T Cells Recognizing 10 Mutated Tumor Antigens," Cancer Immunology Research, Jun. 16, 2016, vol. 4, Issue 8, pp. 669-678.

Qui, F., et al., "Poly(propylacrylic acid)-peptide nanoplexes as a platform for enhancing the immunogenicity of neoantigen cancer vaccines" with supporting information, Biomaterials, vol. 182, pp. 82-91, Nov. 2018, 16 pages.

Rubin et al., "Detection and typing of human papillomavirus DNA in penile carcinoma: evidence for multiple independent pathways of penile carcinogenesis," The American Journal of Pathology, vol. 159, Issue 4, Oct. 2001, pp. 1211-1218.

Shukla, G.S., et al.. , "Immunization with tumor neoantigens displayed on T7 phage nanoparticles elicits plasma antibody and vaccine-draining lymph node B cell responses," Journal of Immunological Methods, vol. 460, Sep. 2018, pp. 51-62.

Stevanovic et al., "Complete regression of metastatic cervical cancer after treatment with human papillomavirus-targeted tumor-infiltrating T cells," Journal of Clinical Oncology, May 2015, vol. 33, Issue 14, pp. 1543-1550.

Svahn et al., "Development and evaluation of a flow-cytometric assay of specific cell-mediated immune response in activated whole blood for the detection of cell-mediated immunity against varicella-zoster virus," Journal of Immunological Methods, vol. 277, Issues 1-2, Jun. 1, 2003, pp. 17-25.

Thunberg et al., "Prolonged antigen-exposure with carbohydrate particle based vaccination prevents allergic immune responses in sensitized mice," Allergy, vol. 64, Issue 6, Jun. 2009, pp. 919-926.

Tornesello et al., "Human papillomavirus genotypes and HPV16 variants in penile carcinoma,", International Journal of Cancer, Jan. 2008, vol. 122, Issue 1, pp. 132-137.

UK Search Report, Intellectual Property Office Patent Application No. GB 1821205.0, Sep. 11, 2019, 2 pages.

(56) References Cited

OTHER PUBLICATIONS

UK Search Report, Intellectual Property Office Patent Application No. GB 1821207.6, Sep. 3, 2019, 2 pages.
United States Office Action, U.S. Appl. No. 16/624,097, filed Apr. 18, 2022, 12 pages.
Yarchoan, M. et al., "Targeting neoantigens to augment antitumour immunity," *Nature Reviews Cancer*, Feb. 24, 2017, vol. 17, pp. 209-222.
Yoon et al., "Anti-tumor immunostimulatory effect of heat-killed tumor cells," 2008, *Experimental & Molecular Medicine*, vol. 40, No. 1, pp. 130-144.
Yuan, H. et al., "Multivalent bi-specific nanobioconjugate engager for targeted cancer immunotherapy," *Nature Nanotechnology*, May 1, 2017, vol. 12, pp. 763-769.
Bellone, S. et al., "Human Papillomavirus Type 16 (HPV-16) Virus-Like Particle L1-Specific CD8$^+$ Cytotoxic T Lymphocytes (CTLs) Are Equally Effective as E7-Specific CD8+ CTLs in Killing Autologous HPV-16-Positive Tumor Cells in Cervical Cancer Patients: Implications for L1 Dendritic Cell-Based Therapeutic Vaccines," *Journal of Virology*, vol. 83, Issue 13, Jul. 1, 2009 (Jul. 1, 2009), p. 6779-6789.
Herrin, D.M. et al., "Comparison of adaptive and innate immune responses induced by licensed vaccines for human papillomavirus," *Human Vaccines & Immunotherapeutics*, vol. 10, Issue 12, Dec. 2014, p. 3446-3454.
International Search Report and Written Opinion, Patent Cooperation Treaty Application No. PCT/EP2019/087030, Mar. 9, 2020, 15 pages.
López-Toledo, G. et al., "Immunization with Human Papillomavirus 16 L1+E2 Chimeric Capsomers Elicits Cellular Immune Response and Antitumor Activity in a Mouse Model," *Viral Immunology*, vol. 29, No. 5, Jun. 3, 2016, p. 276-287.
Luminex Corporation, "MAGPIX Provides Equivalent Performance to the Luminex 100/200 in an HPV Vaccination Trial," May 22, 2014 (May 22, 2014), [Online] [Retrieved Aug. 31, 2021], Retrieved from the Internet <URL:https://www.luminexcorp.com/download/magpix-provides-equivalent-performance-to-the-luminex-100200-in-an-hpv-vaccination-trial/>, 4 pages.
Unger, E. et al., "Laboratory Procedure Manual: Human Papillomavirus in Serum—9-plex competitive Luminex Immuno Assay (9-plex cLIA)," Feb. 25, 2017 (Feb. 25, 2017), [Online][Retrieved Aug. 31, 2021], Retrieved from the Internet <URL:https://web.archive.org/web/20170225212457/https://www.cdc.gov/nchs/data/nhanes/nhanes_05_06/hpvsrm_d_met.pdf>, 8 pages.
Van Poelgeest, M. et al., "Potential use of lymph node-derived HPV-specific T cells for adoptive cell therapy of cervical cancer," *Cancer Immunology, Immunotherapy*, Sep. 12, 2016 (Sep. 12, 2016), vol. 65, No. 12, p. 1451-1463.
Warrino, D. et al., "Human Papillomavirus L1L2-E7 Virus-Like Particles Partially Mature Human Dendritic Cells and Elicit E7-Specific T-Helper Responses from Patients with Cervical Intraepithelial Neoplasia or Cervical Cancer In Vitro," *Human Immunology*, vol. 66, Issue 7, Jul. 2005, p. 762-772.
Zhao, Q. et al., "Characterization of virus-like particles in GARDASIL® by cryo transmission electron microscopy," *Human Vaccines & Immunotherapeutics*, vol. 10, Issue 3, Mar. 2014, p. 734-739.
European Search Report issued Nov. 8, 2023 in connection with European patent application No. 23174945.8.
Berglund et al., 2023, "A first in human Phase I/IIa trial of personalized Tumor-Trained Lymphocytes, pTTL, derived from regional lymph nodes for treatment of colorectal cancer", poster presented at the Society for Immunotherapy of Cancer's (SITC) 38th Annual Meeting.
Berglund et al., 2023, "A First in Human Phase I/IIA of Personalized Tumor-Trained Lymphocytes, PTTL, Derived From Regional Lymph Nodes for Treatment of Colorectal Cancer", Journal for Immuno Therapy of Cancer, 11(Suppl 1):A1-A1731.
Joly et al., 2022, "Personalized Tumour-Trained Lymphocytes Derived From Regional Lymph Nodes for Treatment of Colorectal Cancer", Journal for ImmunoTherapy of Cancer, 10(Suppl 2):A1-A1603.
Joly et al., 2022, "Personalised tumour-trained lymphocytes derived from regional lymph nodes for treatment of colorectal cancer", poster presented at the Society for Immunotherapy of Cancer's (SITC) 37th Annual Meeting.
Koppolu et al., 2013, "The effect of antigen encapsulation in chitosan particles on uptake, activation and presentation by antigen presenting cells", Biomaterials, 34:2359-2369.
Tran et al., 2009, "The role of phagosomal pH on the size-dependent efficiency of cross-presentation by dendritic cells", Biomaterials, 30:1356-1262.
Vidard et al., 1996, "Analysis of MHC class II presentation of particulate antigens of B lymphocytes", 156(8):2809-2818.
Cameron, C.J., et al., "Artificial antigen presenting cells for use in adoptive immunotherapy," *Cancer Journal*, 2010, 16(4):374-381.
Mou et al., 2017, "The Effect of Superparamagnetic Iron Oxide Nanoparticle Surface Charge on Antigen Cross-Presentation", Nanoscale Research Letters, 12(1):52.
Elamanchili et al., 2004, "Characterization of poly(D,L-lactic-co-glycolic acid) based on nanoparticulate system for enhanced delivery of antigens to dendritic cells," Vaccine 22:2406-2412.
Elamanchili et al., 2007, "'Pathogen-Mimicking' Nanoparticles for Vaccine Delivery to Dendritic Cells," J Immunother 30(4):378-395.
Fan et al., 2015, "Nanoparticle Drug Delivery Systems Designed to Improve Cancer Vaccines and Immunotherapy," Vaccines 3:662-685.
Hobo et al., 2010, "siRNA silencing of PD-L1 and PD-L2 on dendritic cells augments expansion and function of minor histocompatibility antigen-specific CD8+ T cells" Blood 116(22):4501-4511.
Joshi et al., 2012, "Targeting tumor antigens to dendritic cells using particulate carriers," Journal of Controlled Release 161: 25-37.
Mayoux et al., 2020, "Dendritic cells dictate responses to PD-L1 blockade cancer immunotherapy," Sci. Transl. Med. 12:1-11.
Rosenberg et al., 2015, "Adoptive cell transfer as personalized immunotherapy for human cancer," Science 348(6230):62-68.
Yoshida et al., 2006, "Molecular aspects of microparticle phagocytosis by dendritic cells," J Biomater: Sci. Polymer Edn 17(8):893-907.
Zhang et al., 2019, "Development of cancer immunotherapy based on PD-1/PD-L1 pathway blockade," RSC Advances 9:33903-33911.
Zhao et al., 2019, "Amplified Cancer Immunotherapy of a Surface-Engineered Antigenic Microparticle Vaccine by Synergistically Modulating Tumor Microenvironment," ACS NANO 13:12553-12566.
International Search Report mailed Oct. 15, 2021 in connection with PCT/EP2021/068267.
UK Search Report mailed Apr. 8, 2021 in connection with GB2010095.4.
Written Opinion mailed Oct. 15, 2021 in connection with PCT/EP2021/068267.
World Health Organization International Agency for Research on Cancer, 2007, "IARC Monographs on the Evaluation of Carcinogenic Risks to Humans, Human Papillomaviruses", 90:1-689.
Pineo et al., 2013, "Immunogenic assessment of plant-produced human papillomavirus type 16 L1/L2 chimaeras", Plant Biotechnology Journal, 11:964-975.

\* cited by examiner

A

B

C

A

B

C

D

E

A

B

C

A

B

A

B

A

B

C

D

B

SEQUENCE LISTING

```
<160> NUMBER OF SEQ ID NOS: 15

<210> SEQ ID NO 1
<211> LENGTH: 568
<212> TYPE: PRT
<213> ORGANISM: Human papillomavirus type 18

<400> SEQUENCE: 1

Met Cys Leu Tyr Thr Arg Val Leu Ile Leu His Tyr His Leu Leu Pro
1               5                   10                  15

Leu Tyr Gly Pro Leu Tyr His Pro Arg Pro Leu Pro Leu His Ser Ile
            20                  25                  30

Leu Val Tyr Met Val His Ile Ile Ile Cys Gly His Tyr Ile Ile Leu
        35                  40                  45

Phe Leu Arg Asn Val Asn Val Phe Pro Ile Phe Leu Gln Met Ala Leu
    50                  55                  60

Trp Arg Pro Ser Asp Asn Thr Val Tyr Leu Pro Pro Pro Ser Val Ala
65                  70                  75                  80

Arg Val Val Asn Thr Asp Asp Tyr Val Thr Pro Thr Ser Ile Phe Tyr
                85                  90                  95

His Ala Gly Ser Ser Arg Leu Leu Thr Val Gly Asn Pro Tyr Phe Arg
            100                 105                 110

Val Pro Ala Gly Gly Gly Asn Lys Gln Asp Ile Pro Lys Val Ser Ala
        115                 120                 125

Tyr Gln Tyr Arg Val Phe Arg Val Gln Leu Pro Asp Pro Asn Lys Phe
    130                 135                 140

Gly Leu Pro Asp Thr Ser Ile Tyr Asn Pro Glu Thr Gln Arg Leu Val
145                 150                 155                 160

Trp Ala Cys Ala Gly Val Glu Ile Gly Arg Gly Gln Pro Leu Gly Val
                165                 170                 175

Gly Leu Ser Gly His Pro Phe Tyr Asn Lys Leu Asp Asp Thr Glu Ser
```

```
            180                 185                 190
Ser His Ala Ala Thr Ser Asn Val Ser Glu Asp Val Arg Asp Asn Val
            195                 200                 205

Ser Val Asp Tyr Lys Gln Thr Gln Leu Cys Ile Leu Gly Cys Ala Pro
            210                 215                 220

Ala Ile Gly Glu His Trp Ala Lys Gly Thr Ala Cys Lys Ser Arg Pro
225                 230                 235                 240

Leu Ser Gln Gly Asp Cys Pro Pro Leu Glu Leu Lys Asn Thr Val Leu
                245                 250                 255

Glu Asp Gly Asp Met Val Asp Thr Gly Tyr Gly Ala Met Asp Phe Ser
                260                 265                 270

Thr Leu Gln Asp Thr Lys Cys Glu Val Pro Leu Asp Ile Cys Gln Ser
            275                 280                 285

Ile Cys Lys Tyr Pro Asp Tyr Leu Gln Met Ser Ala Asp Pro Tyr Gly
            290                 295                 300

Asp Ser Met Phe Phe Cys Leu Arg Arg Glu Gln Leu Phe Ala Arg His
305                 310                 315                 320

Phe Trp Asn Arg Ala Gly Thr Met Gly Asp Thr Val Pro Gln Ser Leu
                325                 330                 335

Tyr Ile Lys Gly Thr Gly Met Pro Ala Ser Pro Gly Ser Cys Val Tyr
                340                 345                 350

Ser Pro Ser Pro Ser Gly Ser Ile Val Thr Ser Asp Ser Gln Leu Phe
                355                 360                 365

Asn Lys Pro Tyr Trp Leu His Lys Ala Gln Gly His Asn Asn Gly Val
                370                 375                 380

Cys Trp His Asn Gln Leu Phe Val Thr Val Val Asp Thr Thr Pro Ser
385                 390                 395                 400

Thr Asn Leu Thr Ile Cys Ala Ser Thr Gln Ser Pro Val Pro Gly Gln
                405                 410                 415

Tyr Asp Ala Thr Lys Phe Lys Gln Tyr Ser Arg His Val Glu Glu Tyr
                420                 425                 430

Asp Leu Gln Phe Ile Phe Gln Leu Cys Thr Ile Thr Leu Thr Ala Asp
            435                 440                 445

Val Met Ser Tyr Ile His Ser Met Asn Ser Ser Ile Leu Glu Asp Trp
            450                 455                 460

Asn Phe Gly Val Pro Pro Pro Thr Thr Ser Leu Val Asp Thr Tyr
465                 470                 475                 480

Arg Phe Val Gln Ser Val Ala Ile Thr Cys Gln Lys Asp Ala Ala Pro
                485                 490                 495

Ala Glu Asn Lys Asp Pro Tyr Asp Lys Leu Lys Phe Trp Asn Val Asp
                500                 505                 510

Leu Lys Glu Lys Phe Ser Leu Asp Leu Asp Gln Tyr Pro Leu Gly Arg
            515                 520                 525

Lys Phe Leu Val Gln Ala Gly Leu Arg Arg Lys Pro Thr Ile Gly Pro
            530                 535                 540

Arg Lys Arg Ser Ala Pro Ser Ala Thr Thr Ser Ser Lys Pro Ala Lys
545                 550                 555                 560

Arg Val Arg Val Arg Ala Arg Lys
                565

<210> SEQ ID NO 2
<211> LENGTH: 505
<212> TYPE: PRT
<213> ORGANISM: Human papillomavirus type 16
```

-continued

<400> SEQUENCE: 2

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
```

```
                    405                 410                 415
Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505

<210> SEQ ID NO 3
<211> LENGTH: 501
<212> TYPE: PRT
<213> ORGANISM: Human papillomavirus type 11

<400> SEQUENCE: 3

Met Trp Arg Pro Ser Asp Ser Thr Val Tyr Val Pro Pro Pro Asn Pro
1               5                  10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270
```

-continued

```
Leu Val Lys Gly Gly Asn Asn Arg Ser Ser Val Ala Ser Ser Ile Tyr
            275                 280                 285

Val His Thr Pro Ser Gly Ser Leu Val Ser Ser Glu Ala Gln Leu Phe
            290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Asp Thr Thr Arg Ser
                325                 330                 335

Thr Asn Met Thr Leu Cys Ala Ser Val Ser Lys Ser Ala Thr Tyr Thr
                340                 345                 350

Asn Ser Asp Tyr Lys Glu Tyr Met Arg His Val Glu Glu Phe Asp Leu
            355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
            435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Arg Thr Ser Ala Arg Thr Gly Ile
465                 470                 475                 480

Lys Arg Pro Ala Val Ser Lys Pro Ser Thr Ala Pro Lys Arg Lys Arg
                485                 490                 495

Thr Lys Thr Lys Lys
                500

<210> SEQ ID NO 4
<211> LENGTH: 500
<212> TYPE: PRT
<213> ORGANISM: Human papillomavirus type 6a

<400> SEQUENCE: 4

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
            85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140
```

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
            165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
            195                 200                 205

Leu Gln Thr Asn Lys Ser Asp Val Pro Ile Asp Ile Cys Gly Thr Thr
210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
            245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
            275                 280                 285

Asn Thr Pro Ser Gly Ser Leu Val Ser Ser Glu Ala Gln Leu Phe Asn
290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
            325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
            355                 360                 365

Phe Ile Phe Gln Leu Cys Ser Ile Thr Leu Ser Ala Glu Val Met Ala
            370                 375                 380

Tyr Ile His Thr Met Asn Pro Ser Val Leu Glu Asp Trp Asn Phe Gly
385                 390                 395                 400

Leu Ser Pro Pro Asn Gly Thr Leu Glu Asp Thr Tyr Arg Tyr Val
            405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
            435                 440                 445

Lys Phe Ser Ser Glu Leu Asp Gln Tyr Pro Leu Gly Arg Lys Phe Leu
450                 455                 460

Leu Gln Ser Gly Tyr Arg Gly Arg Ser Ser Ile Arg Thr Gly Val Lys
465                 470                 475                 480

Arg Pro Ala Val Ser Lys Ala Ser Ala Ala Pro Lys Arg Lys Arg Ala
            485                 490                 495

Lys Thr Lys Arg
            500

<210> SEQ ID NO 5
<211> LENGTH: 500
<212> TYPE: PRT
<213> ORGANISM: Human papillomavirus type 6b

<400> SEQUENCE: 5

Met Trp Arg Pro Ser Asp Ser Thr Val Tyr Val Pro Pro Pro Asn Pro

```
1               5                   10                  15
Val Ser Lys Val Val Ala Thr Asp Ala Tyr Val Thr Arg Thr Asn Ile
            20                  25                  30
Phe Tyr His Ala Ser Ser Arg Leu Leu Ala Val Gly His Pro Tyr
            35                  40                  45
Phe Ser Ile Lys Arg Ala Asn Lys Thr Val Val Pro Lys Val Ser Gly
            50                  55                  60
Tyr Gln Tyr Arg Val Phe Lys Val Val Leu Pro Asp Pro Asn Lys Phe
65                  70                  75                  80
Ala Leu Pro Asp Ser Ser Leu Phe Asp Pro Thr Thr Gln Arg Leu Val
                85                  90                  95
Trp Ala Cys Thr Gly Leu Glu Val Gly Arg Gly Gln Pro Leu Gly Val
                100                 105                 110
Gly Val Ser Gly His Pro Phe Leu Asn Lys Tyr Asp Asp Val Glu Asn
                115                 120                 125
Ser Gly Ser Gly Gly Asn Pro Gly Gln Asp Asn Arg Val Asn Val Gly
                130                 135                 140
Met Asp Tyr Lys Gln Thr Gln Leu Cys Met Val Gly Cys Ala Pro Pro
145                 150                 155                 160
Leu Gly Glu His Trp Gly Lys Gly Lys Gln Cys Thr Asn Thr Pro Val
                165                 170                 175
Gln Ala Gly Asp Cys Pro Pro Leu Glu Leu Ile Thr Ser Val Ile Gln
                180                 185                 190
Asp Gly Asp Met Val Asp Thr Gly Phe Gly Ala Met Asn Phe Ala Asp
                195                 200                 205
Leu Gln Thr Asn Lys Ser Asp Val Pro Ile Asp Ile Cys Gly Thr Thr
                210                 215                 220
Cys Lys Tyr Pro Asp Tyr Leu Gln Met Ala Ala Asp Pro Tyr Gly Asp
225                 230                 235                 240
Arg Leu Phe Phe Phe Leu Arg Lys Glu Gln Met Phe Ala Arg His Phe
                245                 250                 255
Phe Asn Arg Ala Gly Glu Val Gly Glu Pro Val Pro Asp Thr Leu Ile
                260                 265                 270
Ile Lys Gly Ser Gly Asn Arg Thr Ser Val Gly Ser Ser Ile Tyr Val
                275                 280                 285
Asn Thr Pro Ser Gly Ser Leu Val Ser Ser Glu Ala Gln Leu Phe Asn
                290                 295                 300
Lys Pro Tyr Trp Leu Gln Lys Ala Gln Gly His Asn Asn Gly Ile Cys
305                 310                 315                 320
Trp Gly Asn Gln Leu Phe Val Thr Val Val Asp Thr Thr Arg Ser Thr
                325                 330                 335
Asn Met Thr Leu Cys Ala Ser Val Thr Thr Ser Ser Thr Tyr Thr Asn
                340                 345                 350
Ser Asp Tyr Lys Glu Tyr Met Arg His Val Glu Glu Tyr Asp Leu Gln
                355                 360                 365
Phe Ile Phe Gln Leu Cys Ser Ile Thr Leu Ser Ala Glu Val Met Ala
                370                 375                 380
Tyr Ile His Thr Met Asn Pro Ser Val Leu Glu Asp Trp Asn Phe Gly
385                 390                 395                 400
Leu Ser Pro Pro Pro Asn Gly Thr Leu Glu Asp Thr Tyr Arg Tyr Val
                405                 410                 415
Gln Ser Gln Ala Ile Thr Cys Gln Lys Pro Thr Pro Glu Lys Glu Lys
                420                 425                 430
```

```
Pro Asp Pro Tyr Lys Asn Leu Ser Phe Trp Glu Val Asn Leu Lys Glu
            435                 440                 445

Lys Phe Ser Ser Glu Leu Asp Gln Tyr Pro Leu Gly Arg Lys Phe Leu
        450                 455                 460

Leu Gln Ser Gly Tyr Arg Gly Arg Ser Ile Arg Thr Gly Val Lys
465                 470                 475                 480

Arg Pro Ala Val Ser Lys Ala Ser Ala Ala Pro Lys Arg Lys Arg Ala
            485                 490                 495

Lys Thr Lys Arg
            500

<210> SEQ ID NO 6
<211> LENGTH: 158
<212> TYPE: PRT
<213> ORGANISM: Human papillomavirus type 18

<400> SEQUENCE: 6

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val
145                 150                 155

<210> SEQ ID NO 7
<211> LENGTH: 158
<212> TYPE: PRT
<213> ORGANISM: Human papillomavirus type 16

<400> SEQUENCE: 7

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95
```

Gln Gln Tyr Asn Lys Pro Leu Cys Asp Leu Leu Ile Arg Cys Ile Asn
                100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
130                 135                 140

Ser Cys Cys Arg Ser Ser Arg Thr Arg Arg Glu Thr Gln Leu
145                 150                 155

<210> SEQ ID NO 8
<211> LENGTH: 150
<212> TYPE: PRT
<213> ORGANISM: Human papillomavirus type 11

<400> SEQUENCE: 8

Met Glu Ser Lys Asp Ala Ser Thr Ser Ala Thr Ser Ile Asp Gln Leu
1               5                   10                  15

Cys Lys Thr Phe Asn Leu Ser Leu His Thr Leu Gln Ile Gln Cys Val
                20                  25                  30

Phe Cys Arg Asn Ala Leu Thr Thr Ala Glu Ile Tyr Ala Tyr Ala Tyr
            35                  40                  45

Lys Asn Leu Lys Val Val Trp Arg Asp Asn Phe Pro Phe Ala Ala Cys
        50                  55                  60

Ala Cys Cys Leu Glu Leu Gln Gly Lys Ile Asn Gln Tyr Arg His Phe
65                  70                  75                  80

Asn Tyr Ala Ala Tyr Ala Pro Thr Val Glu Glu Glu Thr Asn Glu Asp
                85                  90                  95

Ile Leu Lys Val Leu Ile Arg Cys Tyr Leu Cys His Lys Pro Leu Cys
            100                 105                 110

Glu Ile Glu Lys Leu Lys His Ile Leu Gly Lys Ala Arg Phe Ile Lys
        115                 120                 125

Leu Asn Asn Gln Trp Lys Gly Arg Cys Leu His Cys Trp Thr Thr Cys
    130                 135                 140

Met Glu Asp Leu Leu Pro
145                 150

<210> SEQ ID NO 9
<211> LENGTH: 150
<212> TYPE: PRT
<213> ORGANISM: Human papillomavirus type 6a

<400> SEQUENCE: 9

Met Glu Ser Ala Asn Ala Ser Thr Ser Ala Thr Thr Ile Asp Gln Leu
1               5                   10                  15

Cys Lys Thr Phe Asn Leu Ser Met His Thr Leu Gln Ile Asn Cys Val
                20                  25                  30

Phe Cys Lys Asn Ala Leu Thr Thr Ala Glu Ile Tyr Ser Tyr Ala Tyr
            35                  40                  45

Lys Gln Leu Lys Val Leu Phe Arg Gly Gly Tyr Pro Tyr Ala Ala Cys
        50                  55                  60

Ala Cys Cys Leu Glu Phe His Gly Lys Ile Asn Gln Tyr Arg His Phe
65                  70                  75                  80

Asp Tyr Ala Gly Tyr Ala Thr Thr Val Glu Glu Glu Thr Lys Gln Asp
                85                  90                  95

Ile Leu Asp Val Leu Ile Arg Cys Tyr Leu Cys His Lys Pro Leu Cys
            100                 105                 110

```
Glu Val Glu Lys Val Lys His Ile Leu Thr Lys Ala Arg Phe Ile Lys
            115                 120                 125

Leu Asn Cys Thr Trp Lys Gly Arg Cys Leu His Cys Trp Thr Thr Cys
    130                 135                 140

Met Glu Asp Met Leu Pro
145                 150

<210> SEQ ID NO 10
<211> LENGTH: 105
<212> TYPE: PRT
<213> ORGANISM: Human papillomavirus type 18

<400> SEQUENCE: 10

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 11
<211> LENGTH: 98
<212> TYPE: PRT
<213> ORGANISM: Human papillomavirus type 16

<400> SEQUENCE: 11

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 12
<211> LENGTH: 98
<212> TYPE: PRT
<213> ORGANISM: Human papillomavirus type 16

<400> SEQUENCE: 12

Met His Gly Arg Leu Val Thr Leu Lys Asp Ile Val Leu Asp Leu Gln
1               5                   10                  15

Pro Pro Asp Pro Val Gly Leu His Cys Tyr Glu Gln Leu Glu Asp Ser
```

```
                    20                  25                  30

Ser Glu Asp Glu Val Asp Lys Val Asp Lys Gln Asp Ala Gln Pro Leu
            35                  40                  45

Thr Gln His Tyr Gln Ile Leu Thr Cys Cys Cys Gly Cys Asp Ser Asn
        50                  55                  60

Val Arg Leu Val Val Glu Cys Thr Asp Gly Asp Ile Arg Gln Leu Gln
 65                  70                  75                  80

Asp Leu Leu Gly Thr Leu Asn Ile Val Cys Pro Ile Cys Ala Pro
                85                  90                  95

Lys Pro

<210> SEQ ID NO 13
<211> LENGTH: 98
<212> TYPE: PRT
<213> ORGANISM: Human papillomavirus type 6a

<400> SEQUENCE: 13

Met His Gly Arg His Val Thr Leu Lys Asp Ile Val Leu Asp Leu Gln
 1               5                  10                  15

Pro Pro Asp Pro Val Gly Leu His Cys Tyr Glu Gln Leu Val Asp Ser
                20                  25                  30

Ser Glu Asp Glu Val Asp Glu Val Asp Gly Gln Asp Ser Gln Pro Leu
            35                  40                  45

Lys Gln His Phe Gln Ile Val Thr Cys Cys Cys Gly Cys Asp Ser Asn
        50                  55                  60

Val Arg Leu Val Val Gln Cys Thr Glu Thr Asp Ile Arg Glu Val Gln
 65                  70                  75                  80

Gln Leu Leu Leu Gly Thr Leu Asp Ile Val Cys Pro Ile Cys Ala Pro
                85                  90                  95

Lys Thr

<210> SEQ ID NO 14
<211> LENGTH: 98
<212> TYPE: PRT
<213> ORGANISM: Human papillomavirus type 6b

<400> SEQUENCE: 14

Met His Gly Arg His Val Thr Leu Lys Asp Ile Val Leu Asp Leu Gln
 1               5                  10                  15

Pro Pro Asp Pro Val Gly Leu His Cys Tyr Glu Gln Leu Val Asp Ser
                20                  25                  30

Ser Glu Asp Glu Val Asp Glu Val Asp Gly Gln Asp Ser Gln Pro Leu
            35                  40                  45

Lys Gln His Phe Gln Ile Val Thr Cys Cys Cys Gly Cys Asp Ser Asn
        50                  55                  60

Val Arg Leu Val Val Gln Cys Thr Glu Thr Asp Ile Arg Glu Val Gln
 65                  70                  75                  80

Gln Leu Leu Leu Gly Thr Leu Asn Ile Val Cys Pro Ile Cys Ala Pro
                85                  90                  95

Lys Thr

<210> SEQ ID NO 15
<211> LENGTH: 257
<212> TYPE: PRT
<213> ORGANISM: Artificial Sequence
<220> FEATURE:
<223> OTHER INFORMATION: Cytomegalovirus pp65 construct
```

-continued

```
<400> SEQUENCE: 15

Met Gly Ser Ser His His His His His Ser Ser Gly Ser Leu Ala
1               5                   10                  15

Glu Ala Lys Val Leu Ala Asn Arg Glu Leu Asp Lys Tyr Gly Val Ser
            20                  25                  30

Asp Tyr His Lys Asn Leu Ile Asn Asn Ala Lys Thr Val Glu Gly Val
        35                  40                  45

Lys Asp Leu Gln Ala Gln Val Val Glu Ser Ala Lys Lys Ala Arg Ile
    50                  55                  60

Ser Glu Ala Thr Asp Gly Leu Ser Asp Phe Leu Lys Ser Gln Thr Pro
65                  70                  75                  80

Ala Glu Asp Thr Val Lys Ser Ile Glu Leu Ala Glu Ala Lys Val Leu
                85                  90                  95

Ala Asn Arg Glu Leu Asp Lys Tyr Gly Val Ser Asp Tyr Tyr Lys Asn
            100                 105                 110

Leu Ile Asn Asn Ala Lys Thr Val Glu Gly Val Lys Ala Leu Ile Asp
        115                 120                 125

Glu Ile Leu Ala Ala Leu Pro Gly Gly Ser Ala Glu Thr Arg Leu Leu
130                 135                 140

Gln Thr Gly Ile His Val Arg Val Ser Gln Pro Ser Leu Ile Leu Val
145                 150                 155                 160

Gly Gly Ser Ile Ile Lys Pro Gly Lys Ile Ser His Ile Met Leu Asp
                165                 170                 175

Val Ala Phe Thr Ser His Glu His Phe Gly Gly Ser Trp Pro Pro Trp
            180                 185                 190

Gln Ala Gly Ile Leu Ala Arg Asn Leu Val Pro Met Val Ala Thr Val
            195                 200                 205

Gln Gly Gly Ser Arg Gly Pro Gln Tyr Ser Glu His Pro Thr Phe Thr
    210                 215                 220

Ser Gln Tyr Arg Ile Gln Gly Lys Leu Gly Gly Ser Gln Asn Leu Lys
225                 230                 235                 240

Tyr Gln Glu Phe Phe Trp Asp Ala Asn Asp Ile Tyr Arg Ile Phe Ala
                245                 250                 255

Glu
```

METHOD FOR THE EXPANSION OF HPV IMMUNOGEN SPECIFIC T-CELLS

CROSS-REFERENCE TO RELATED APPLICATIONS

This application is the National Stage of International Application No. PCT/EP2019/087030, filed on Dec. 24, 2019, which claims the benefit of and priority to Great Britain Patent Application No. 1821207.6, filed on Dec. 24, 2018, the contents of which are incorporated by reference in their entirety.

SEQUENCE LISTING

The instant application contains a Sequence Listing which has been submitted via EFS-Web and is hereby incorporated by reference in its entirety. Said ASCII copy, created on Mar. 2, 2022, is named 49350US_CRF_sequencelisting2.txt, and is 35,239 bytes in size.

FIELD OF THE INVENTION

The present invention relates to a method of providing therapeutically useful T-cells and their use in the treatment or prevention of cancer, particularly HPV positive cancers.

BACKGROUND

Human papillomavirus (HPV) is a DNA virus belonging to the papillomavirus family that has the capability to infect humans. HPV infection accounts for 5.2% of all cancers such as cervical cancer, oropharyngeal cancer and penile cancer, worldwide (Rubin et al., Am J Pathol. 2001, 159, 1211-1218). More than 170 HPV types have been identified (Chouhy D et al., J Gen Virol, 2013, 94, 2480-2488). Based on their risk of inducing malignancy, HPV types are grouped into high or low-risk types. The high-risk group (including HPV-8, -16, -18 and -31) are associated with cancers (Motoyama et al., Kobe J Med Sci, 2004, 50, 9-19), whereas the low-risk types (including HPV-6, and -11) can lead to benign warts and lesions without transformation. Studies on penile cancer have demonstrated that the most prevalent strain is HPV16 (Tornesello et al. Int J Cancer, 2008, 122, 132-137). Some types generally classified as 'low risk' can however, in some settings constitute higher risk infections. For example, a case report with invasive verrucous carcinoma of the penis reported association with the low risk HPV 11 (Dianzani et al., Urology, 1998, 51, 1046-1048).

The HPV genome encodes two shell proteins (L1 and L2) and six early proteins (E1, E2 and E4-E7), which support replication of the viral DNA and production of virus particles and their assembly in the infected cells (Munoz et al., Vaccine, 2006, 24 Suppl 3:S3/1-10).

Animal studies suggest the HPV proteins E6 and E7 could affect cell growth control by inactivating the tumour suppressors p53 and retinoblastoma protein (pRb), respectively (Pan et al., Genes Dev, 1994, 8, 1285-1299).

Despite the interest in immunotherapies for treating cancers, such as HPV positive cancers, they have to date had limited success. This is due to ineffective modulation or induction of a specific immune response, together with challenges associated with the safety and selectivity of the immunotherapy.

There are various approaches for modulating the immune system of a subject to treat cancer; such approaches are often referred to as "immunotherapies". Examples of immunotherapies include immune checkpoint inhibitors, adoptive cell transfer (ACT) therapies, and cancer vaccines.

There has been much success in using immune checkpoint inhibitors for treating cancer, such as the use of monoclonal antibodies that target binding interactions that are important to checkpoints of immune activation. Immune checkpoint inhibitors have been used for the treatment of various cancers, for example in the treatment of melanoma, lung cancer, bladder cancer and gastrointestinal cancers.

There has also been some success with adoptive cell transfer (ACT). For example, a study in which patients with advanced colon cancer were treated using an adoptive immunotherapy protocol was reported by Karlsson et al., (Ann Surg Oncol 2010, 17(7), 1747-57). The treatment was based on the isolation and in vitro expansion of autologous tumour-reactive lymphocytes isolated intraoperatively from the first lymph node that naturally drains the tumour (the sentinel node). Sentinel node acquired lymphocytes were collected, activated, expanded against an autologous tumour extract and returned to the patient as a transfusion. No toxic side effects or other adverse effects were observed. Total or marked regression of the disease occurred in four patients with liver and lung metastases and twelve patients displayed partial regression or stable disease.

A significant limitation for ACT is the need to prepare sufficient quantities of immunogen specific T-cells, such as tumour-infiltrating lymphocytes (TILS), for administration to a subject. For example, current methods often require the use of invasive surgical procedures to remove a cancer or cancer cells of a subject in order to obtain antigen specific T-cells. Furthermore, the cells obtained are few and are frequently unresponsive (anergic) due to immunosuppressive mechanisms from the cancer. This can lead to in vitro expansion being slow, which in turn means that it can take a long time to obtain sufficient quantities of antigen specific T cells for therapeutic use.

Genetically engineered T-cells have been developed to overcome some of the limitations of ACT. Genetically engineered T-cells may be obtained by genetically redirecting a T-cell specificity towards a patient's cancer by introduction of antigen receptors or by introducing a synthetic recognition structure termed a "chimeric antigen receptor" into a T-cell. Although genetically engineered T-cells have found success in treating hematologic cancers, the safety and selectivity of genetically engineered T-cells for treating solid cancers still requires improvement.

There have been reports of some exploratory studies on immunotherapy for HPV-induced cancers. For example, Borysiewicz L K, et al., (Lancet, 1996, 347, 1523-1527) reported on a study in which patients were vaccinated with a single dose of a live recombinant vaccinia virus expressing the E6 and E7 proteins of HPV 16 and 18 (TA-HPV). Each patient mounted an anti-vaccinia antibody response and three of the eight patients developed a HPV-specific antibody response that could be ascribed to the vaccination. HPV-specific cytotoxic T lymphocytes were detected in one of three evaluable patients. Bagarazzi et al. reported on a study of the immune relevance of the E6 and E7 proteins in HPV associated immunotherapy of cervical cancer (Bagarazzi et al. Sci Transl Med, 2012, 4, 155-138): when subjects previously treated for cervical intraepithelial neoplasia grade 2 or 3 (CIN2/3) received a three-dose (intramuscular) regimen of engineered plasmid DNA encoding HPV16 and HPV18 E6/E7, flow cytometric analysis revealed the induction of HPV-specific CD8(+) T cells that efficiently loaded granzyme B and perforin and exhibited full cytolytic functionality.

Bellone et al., (J Virol, 2009, 83, 6779-6789) reported a study comparing the efficiency of different HPV immunogen specific T cells in eliminating autologous HPV positive tumour cells from patients with cervical cancer. The study concludes that L1-specific CD8+ cytotoxic T cells are as effective as E7-specific CD8+ T-cells. Lastly, Stevanovic et al. (J Clin Onc, 2015, 43, 33(14):1543-1550) reported on a treatment of cervical cancer in which patients were treated with lymphocyte depleting chemotherapy followed by a single infusion of tumour-infiltrating lymphocytes. The tumour-infiltrating lymphocytes were obtained from the tumour. The lymphocytes infused were selected, where possible, for HPV E6 and E7 reactivity. Three of nine subjects experienced objective tumour responses, leading the authors to conclude that further investigations of therapies of this type are warranted.

Selection and expansion of the most therapeutically useful T cells is going to be central to the success of T-cell based immunotherapy of HPV-mediated cancers. There remains a need for improvements in this area to enable development of immunotherapies for use in the treatment of prophylaxis of cancers and that are also suitable for use in a clinical setting.

SUMMARY OF THE INVENTION

The present invention provides a method for the expansion of HPV immunogen specific T-cells, comprising the steps of:
 i. providing a human papillomavirus (HPV) immunogen or a phagocytosable particle comprising a core and a HPV immunogen tightly associated to the core; wherein the HPV immunogen has an amino acid sequence that corresponds to the amino acid sequence of a HPV protein, or has an amino acid sequence that corresponds to an amino acid sequence of a part of a HPV protein;
 ii. providing APCs
 iii. contacting the HPV immunogen or the phagocytosable particle comprising a core and a HPV immunogen with the APCs from step ii in vitro, and under conditions allowing phagocytosis of the HPV immunogen by the APCs;
 iv. providing T-cells that have been harvested from the subject;
 v. contacting the T-cells with the APCs from step iii) in vitro, and under conditions allowing specific activation of HPV immunogen specific T-cells.

The present inventors have found that suitable HPV immunogens include HPV proteins necessary for viral replication (e.g. E1 to E7) and HPV coat proteins (e.g. L1 and L2). The inventors have found that HPV immunogens contained in commercially available HPV vaccine (for example Gardasil®, Gardasil 9° and/or Cervarix®) are particularly effective for use with the method of the present invention. In preferred embodiments of the invention the HPV immunogens for use in the method of the invention are one or more of HPV coat protein L1 derived from any one of HPV types 6, 11, 16, 18, 31, 33, 45, 52 and 58.

In certain embodiments of the invention, the HPV immunogen for use in the method of the present invention has an amino acid sequence that corresponds to a part of a HPV protein. Preferably, the HPV immunogen has an amino acid sequence that corresponds to a part of a HPV coat protein L1 derived from any one of HPV types 6, 11, 16, 18, 31, 33, 45, 52 and 58.

The present invention also provides a population of HPV immunogen specific T-cells for use in the treatment of a HPV positive cancer in a subject, wherein the T-cells have been prepared by a process in which T-cells are obtained from the subject, and exposed ex vivo to an HPV immunogen resulting in T-cell activation and proliferation.

The resulting expanded and activated T-cells are useful in the treatment of HPV positive cancers, such as HPV positive cervical, vaginal, vulval, penile, anal, mouth, throat and head and neck cancers. The expanded and activated T cells are particularly effective for the treatment of penile cancers. It has surprisingly been found by the current inventors that lymph node derived T-cells from HPV positive penile cancer patients responded in a dose dependent manner to a HPV immunogen, resulting in T-cell activation and proliferation. Furthermore, using a model virus antigen construct (CMV), the present inventors have shown that the phagocytosable particles and ex-vivo expansion method of the present invention are surprisingly effective for expanding virus-specific T-cells isolated from a subject. As such, the present inventors provide an expansion method described herein which is an effective method for preparing HPV specific T-cells, which will find utility in adoptive T-cell therapies for HPV-mediated cancers.

The present invention also provides a method of treating or preventing a HPV positive cancer comprising the step of administering to the subject a population of HPV immunogen specific T-cells.

The present invention also provides the use of a population of HPV immunogen specific T-cells for the manufacture of a medicament for the treatment or prevention of a HPV positive cancer in a subject.

The present invention also provides an injectable pharmaceutical composition comprising a population of HPV immunogen specific T-cells, wherein the injectable pharmaceutical composition optionally further comprises a pharmaceutically acceptable excipient and/or an adjuvant.

The invention also provides a phagocytosable particle comprising a core and a HPV immunogen tightly associated to the core, wherein the HPV immunogen has an amino acid sequence that corresponds to the amino acid sequence of a HPV protein, or has an amino acid sequence that corresponds to an amino acid sequence of a part of a HPV protein. Such HPV proteins include, for example, HPV proteins necessary for viral replication (e.g. E1 to E7) and HPV coat proteins (e.g. L1 and L2). The present inventors have found that a particularly suitable source of HPV immunogens for use in the method of the invention is Gardasil®, Gardasil 9° and/or Cervarix®.

The present inventors have found that phagocytosable particles as described herein can be efficiently purified and sterilised, thus removing contaminants, such as pathogens (e.g. bacteria, fungus and viruses), endotoxins and other antigenic contaminants from the phagocytosable particles that are used in the method of the present invention. This is particularly advantageous because the removal of contaminants from the phagocytosable particles of the invention reduces contamination of the HPV specific T-cell population provided by the present invention. Reduced levels of contaminates, such as pathogens and other antigenic contaminants in the population of T-cells for administering to a subject reduces non-specific immune responses and therefore improves safety and efficacy of the HPV specific T-cell population in treating or preventing HPV positive cancers.

The core of a phagocytosable particle (e.g. a polymer particle) as described herein acts as a very effective carrier for the HPV immunogens. Without wishing to be bound by any particular theory, it is believed that phagocytosable particles as defined herein are especially effective because the entire phagocytosable particle, including the core and tightly associated HPV immunogen, are internalised by APCs by phagocytosis into a phagosome. The HPV immunogen is then cleaved from the core of the particle and processed in the phagosome. Fragments of the HPV immunogen are then presented on the surface of the APC via the major histocompatibility (MHC) class II pathway and presented on the cell surface by a MHC class II molecule. It is also believed that this is not the exclusive process for the HPV immunogen to be presented on surface of an APC, and that some fragments of the HPV immunogen may also be presented on the surface of APCs via the major histocompatibility (MHC) class I pathway and presented on the cell surface by a MHC class I molecule, in a process known as cross-presentation. Thus, although it is expected that fragments of the HPV immunogen are presented on APCs predominantly via the MHC class II pathway, it is expected that some will be presented via the MHC class I pathway, and so the present invention harnesses both pathways to a varying extent.

When antigens are presented by an MHC class II molecule, they generally activate helper T-cells (also known as CD4+ T-cells), which predominantly orchestrate immune responses by secretion of cytokines, inducing class switching of B-cells to assist the B-cells to make antibodies and stimulating activation and expansion of other T-cell types, in particular cytotoxic T-cells (e.g. CD8+ T-cells) and memory T-cells (e.g. CD8+ memory T-cells). In addition, CD4+ T-cells can directly kill other cell types (Borst et al. Nat Rev Immunol, 2018, 18(10), 635-647). This means that by administering a population of HPV immunogen specific T-cells that have been activated by the phagocytosable particles as defined herein to a subject, it is possible to administer multiple types of activated immune cells, which results in a HPV immunogen specific immune response that starts slowly (thus leading to few side effects), has a long lasting effect, and can target the cancer in many different ways by harnessing the whole immune system (rather than only activating CD8+ T-cell which can only attack the tumour cells directly). This is in contrast to what would be expected to occur when an antigen (e.g. a HPV immunogen) is provided as free peptide or a nucleotide construct that expresses the peptide. Such an antigen would be expected to be taken up into the cytosol of an APC, which results in the antigen being presented on the cell surface solely via the MHC class I pathway by an MHC class I molecule. This, in turn, results predominantly in the activation of CD8+ T-cells. Furthermore, after the administration of a first dose of antigen specific T-cells (CD4+ T-cells and CD8+ T-cells) that have been expanded ex-vivo, memory T-cells derived from the antigen specific T-cells administered to the subject remain in circulation and can mount a rapid and effective secondary immune response for as long as cancer cells expressing the HPV proteins remain in the body, or if the same cancer returns. Thus, HPV immunogen specific T-cells expanded according to the method of the present invention, when expanded and administered to a patient, will continue to work even after the original T-cells administered as a first dose to the subject have died, due to the memory T-cells that remain in circulation.

The present inventors also understand that it will not be necessary to remove the phagocytosable particles used in the ex-vivo expansion method of the invention from the population of T-cells before the population of T-cells are administered to a subject. Without wishing to be bound by theory, the inventors believe that this is because of the low toxicity of the core and the high sterility of the particles used in the method (for details of the sterilisation procedure see Examples 2 and 7). Not removing the phagocytosable particles from the expanded T-cells will advantageously reduce the number of steps required to prepare a population of T-cells for use in treatments according to the invention.

DETAILED DESCRIPTION OF THE INVENTION

HPV Immunogens and HPV Immunogen Compositions

Figure 1:
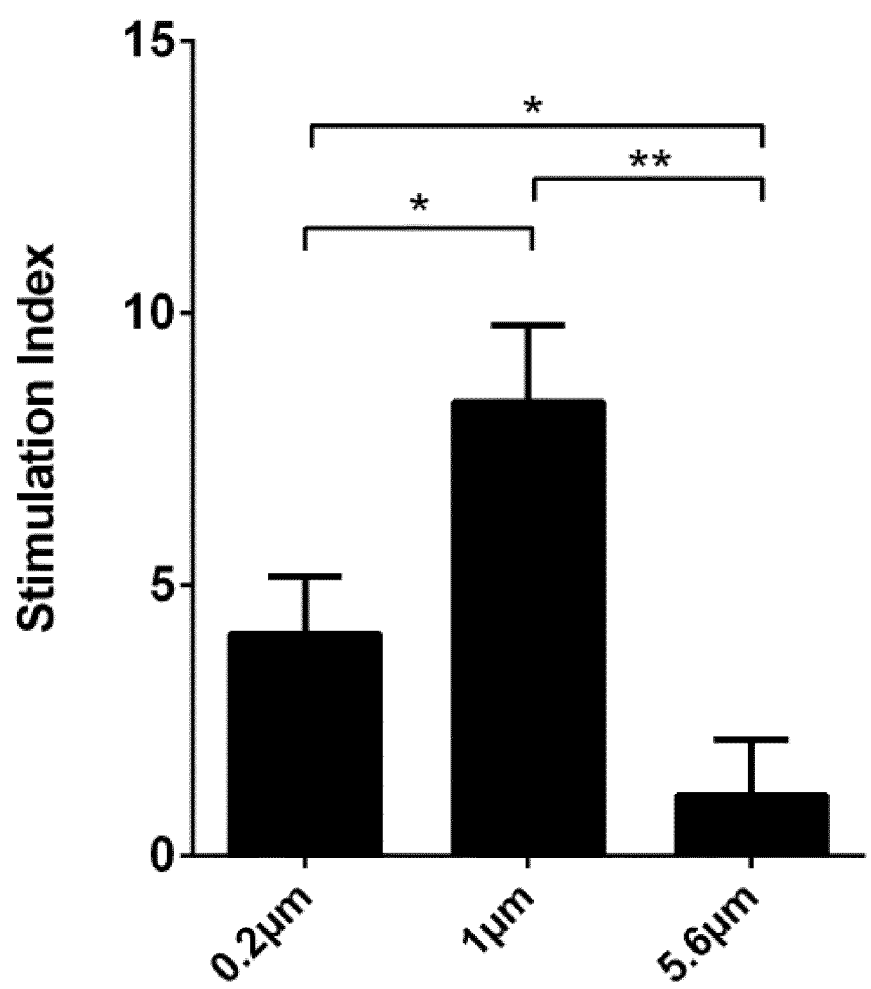
FIG. 1 shows the effect of phagocytosable particle size on T-cell activation. A proliferation assay (with thymidine incorporation) was used to assess the number of splenocytes obtained from ovalbumin sensitized mice. Comparison of ovalbumin coupled to differently sized phagocytosable particle with a diameter of 5.6 µm, 1 µm and 0.2 µm are shown. P-values determined using students T-test and written indicated when $p<0.05$ found. Staples denote SD.

HPV immunogens for use in the method of the invention may preferably be selected from the HPV viral replication proteins E1, E2, E3, E4, E5, E6 and E7 and the HPV coat proteins L1 and L2.

There are over 170 types of HPV virus. Certain HPV types are known to cause cancer in an infected individual, other HPV types are suspected of causing cancers and other types are not associated with cancer. HPV types 16, 18, 31, 33, 35, 39, 45, 51, 52, 56, 58, 59, 68, 73, and 82 are considered carcinogenic, and types 26, 53, and 66 are considered as probably carcinogenic (Munoz et al., N Engl J Med 2003, 348, 518-527). Thus, in preferred embodiments of the invention, the HPV immunogen has an amino acid sequence that corresponds to the amino acid sequence of a HPV protein derived from HPV types 16, 18, 31, 33, 35, 39, 45, 51, 52, 56, 58, 59, 68, 73, 82, 26, 53 or 66. For example, the HPV immunogen may have an amino acid sequence that corresponds to the amino acid sequence of a HPV protein selected from HPV viral replication proteins E1, E2, E3, E4, E5, E6 and E7 and the HPV coat proteins L1 and L2 derived for any one of HPV types 16, 18, 31, 33, 35, 39, 45, 51, 52, 56, 58, 59, 68, 73, 82, 26, 53 or 66. More preferably, the HPV immunogen has an amino acid sequence that corresponds to the amino acid sequence of a HPV protein derived from any one of HPV types 16, 18, 31, 33, 35, 39, 45, 51, 52, 56, 58, 59, 68, 73 or 82. More preferably, a HPV protein is derived from any one of HPV types 6, 11, 16, 18, 31, 33, 45, 52 and 58. For example, the HPV immunogen may have an amino acid sequence that corresponds to the amino acid sequence of a HPV protein selected from one of HPV viral replication proteins E1, E2, E3, E4, E5, E6 and E7 and the HPV coat proteins L1 and L2 derived for any one of HPV types 6, 11, 16, 18, 31, 33, 45, 52 and 58. More preferably, the HPV immunogen has an amino acid sequence that corresponds to the amino acid sequence of a HPV coat protein (e.g. L1 and L2) derived from any one of HPV types 6, 11, 16, 18, 31, 33, 45, 52 and 58. Even more preferably, the HPV immunogen has an amino acid sequence that corresponds to the amino acid sequence of a HPV coat protein L1 derived from any one of HPV types 6, 11, 16, 18, 31, 33, 45, 52 and 58.

In each case, the HPV immunogen may be a protein or peptide having an amino acid sequence corresponding to a part of the amino acid sequence of a HPV protein. The part should have a length sufficient to be able to bring about a specific immune response. For example, the part has a length of at least 10 amino acids. For example, it is at least 15, at least 20, at least 25, at least 30, at least 35, at least 40, at least 45 or at least 50 amino acids long. The part may optionally have a length of less than or equal to 600 amino acids. For example, it is less than or equal to 500, less than or equal to 400, less than or equal to 300, less than or equal to 200, less than or equal to 100, less than or equal to 75, less than or equal to 60 or less than or equal to 50 amino acids. For example, the part may have a length of 15, 20, 25, 30, 35, 40, 45, 50, 55, 60, 65, 70, 85, 90, 95, 100, 120, 130, 140, 150, 160, 170, 180, 190, 200, 250, 300, 350, 400, 450, 500, 550 or 600 amino acids.

The inventors have found that HPV immunogens contained in commercially available HPV vaccines such as Gardasil®, Gardasil 9° and/or Cervarix® are particularly effective for use with the method of the present invention. Gardasil® contains HPV coat protein L1 derived from HPV types 6, 11, 16 and 18; Gardasil 9° contains HPV coat protein L1 derived from HPV types 6, 11, 16, 18, 31, 33, 45, 52 and 58; and Cervarix® contains HPV coat protein L1 derived from HPV types 6 and 11. Thus, in preferred embodiments, the HPV immunogen for use in the method of the present invention is a peptide present in Gardasil®, Gardasil 9° and/or Cervarix®. Preferably, the one or more HPV immunogen are peptides present in Gardasil® and/or Gardasil 9®. In one embodiment, the one or more HPV immunogen are peptides selected from the group consisting of SEQ ID NO. 1, SEQ ID NO. 2, SEQ ID NO. 3, SEQ ID NO. 4 and SEQ ID NO. 5.

In another embodiment, the one or more HPV immunogen are peptides HPV coat protein L1, E6 or E7 derived from HPV types 6, 11, 16 and 18 selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14 and SEQ ID NO. 15.

| SEQ ID NO. | Description | Sequence |
| --- | --- | --- |
| 1 | HPV coat protein L1 derived from HPV type 18 | MCLYTRVLILHYHLLPLYGPLYHPRPLPLHSILVYMVHIIICGHYIILFLRNVNVFPIFL QMALWRPSDNTVYLPPPSVARVVNTDDYVTPTSIFYHAGSSRLLTVGNPYFRVPA GGGNKQDIPKVSAYQYRVFRVQLPDPNKFGLPDTSIYNPETQRLVWACAGVEIG RGQPLGVGLSGHPFYNKLDDTESSHAATSNVSEDVRDNVSVDYKQTQLCILGCA PAIGEHWAKGTACKSRPLSQGDCPPLELKNTVLEDGDMVDTGYGAMDFSTLQD TKCEVPLDICQSICKYPDYLQMSADPYGDSMFFCLRREQLFARHFWNRAGTMG DTVPQSLYIKGTGMPASPGSCVYSPSPSGSIVTSDSQLFNKPYWLHKAQGHNNG VCWHNQLFVTVVDTTPSTNLTICASTQSPVPGQYDATKFKQYSRHVEEYDLQFIF QLCTITLTADVMSYIHSMNSSILEDWNFGVPPPPTTSLVDTYRFVQSVAITCQKDA APAENKDPYDKLKFWNVDLKEKFSLDLDQYPLGRKFLVQAGLRRKPTIGPRKRSA PSATTSSKPAKRVRVRARK |
| 2 | HPV coat protein L1 derived from HPV type 16 | MSLWLPSEATVYLPPVPVSKVVSTDEYVARTNIYYHAGTSRLLAVGHPYFPIKKPN NNKILVPKVSGLQYRVFRIHLPDPNKFGFPDTSFYNPDTQRLVWACVGVEVGRG QPLGVGISGHPLLNKLDDTENASAYAANAGVDNRECISMDYKQTQLCLIGCKPPI GEHWGKGSPCTNVAVNPGDCPPLELINTVIQDGDMVDTGFGAMDFTTLQANK SEVPLDICTSICKYPDYIKMVSEPYGDSLFFYLRREQMFVRHLFNRAGAVGENVPD DLYIKGSGSTANLASSNYFPTPSGSMVTSDAQIFNKPYWLQRAQGHNNGICWG NQLFVTVVDTTRSTNMLSCAAISTSETTYKNTNFKEYLRHGEEYDLQFIFQLCKITL TADVMTYIHSMNSTILEDWNFGLQPPPGGTLEDTYRFVTSQAIACQKHTPPAPK EDPLKKYTFWEVNLKEKFSADLDQFPLGRKFLLQAGLKAKPKFTLGKRKATPTTSS TSTTAKRKKRKL |
| 3 | HPV coat protein L1 derived from HPV type 11 | MWRPSDSTVYVPPPNPVSKVVATDAYVKRTNIFYHASSSRLLAVGHPYYSIKKVN KTVVPKVSGYQYRVFKVVLPDPNKFALPDSSLFDPTTQRLVWACTGLEVGRGQPL GVGVSGHPLLNKYDDVENSGGYGGNPGQDNRVNVGMDYKQTQLCMVGCAPP LGEHWGKGTQCSNTSVQNGDCPPLELITSVIQDGDMVDTGFGAMNFADLQTN KSDVPLDICGTVCKYPDYLQMAADPYGDRLFFYLRKEQMFARHFFNRAGTVGEP VPDDLLVKGGNNRSSVASSIYVHTPSGSLVSSEAQLFNKPYWLQKAQGHNNGIC WGNHLFVTVVDTTRSTNMTLCASVSKSATYTNSDYKEYMRHVEEFDLQFIFQLCS ITLSAEVMAYIHTMNPSVLEDWNFGLSPPPNGTLEDTYRYVQSQAITCQKPTPEK EKQDPYKDMSFWEVNLKEKFSSELDQFPLGRKFLLQSGYRGRTSARTGIKRPAVS KPSTAPKRKRTKTKK |
| 4 | HPV coat protein L1 derived from HPV type 6A | MWRPSDSTVYVPPPNPVSKVVATDAYVTRTNIFYHASSSRLLAVGHPYFSIKRAN KTVVPKVSGYQYRVFKVVLPDPNKFALPDSSLFDPTTQRLVWACTGLEVGRGQPL GVGVSGHPFLNKYDDVENSGSGGNPGQDNRVNVGMDYKQTQLCMVGCAPPL GEHWGKGKQCTNTPVQAGDCPPLELITSVIQDGDMVDTGFGAMNFADLQTNK SDVPIDICGTTCKYPDYLQMAADPYGDRLFFFLRKEQMFARHFFNRAGEVGEPVP DTLIIKGSGNRTSVGSSIYVNTPSGSLVSSEAQLFNKPYWLQKAQGHNNGICWGN QLFVTVVDTTRSTNMTLCASVTTSSTYTNSDYKEYMRHVEEYDLQFIFQLCSITLSA EVMAYIHTMNPSVLEDWNFGLSPPPNGTLEDTYRYVQSQAITCQKPTPEKEKPD PYKNLSFWEVNLKEKFSSELDQYPLGRKFLLQSGYRGRSSIRTGVKRPAVSKASAA PKRKRAKTKR |
| 5 | HPV coat protein E6 derived from HPV type 68 | MWRPSDSTVYVPPPNPVSKVVATDAYVTRTNIFYHASSSRLLAVGHPYFSIKRAN KTVVPKVSGYQYRVFKVVLPDPNKFALPDSSLFDPTTQRLVWACTGLEVGRGQPL GVGVSGHPFLNKYDDVENSGSGGNPGQDNRVNVGMDYKQTQLCMVGCAPPL GEHWGKGKQCTNTPVQAGDCPPLELITSVIQDGDMVDTGFGAMNFADLQTNK SDVPIDICGTTCKYPDYLQMAADPYGDRLFFFLRKEQMFARHFFNRAGEVGEPVP DTLIIKGSGNRTSVGSSIYVNTPSGSLVSSEAQLFNKPYWLQKAQGHNNGICWGN QLFVTVVDTTRSTNMTLCASVTTSSTYTNSDYKEYMRHVEEYDLQFIFQLCSITLSA EVMAYIHTMNPSVLEDWNFGLSPPPNGTLEDTYRYVQSQAITCQKPTPEKEKPD PYKNLSFWEVNLKEKFSSELDQYPLGRKFLLQSGYRGRSSIRTGVKRPAVSKASAA PKRKRAKTKR |
| 6 | HPV viral replication protein L1 derived from HPV type 18 | MARFEDPTRRPYKLPDLCTELNTSLQDIEITCVYCKTVLELTEVFEFAFKDLFVVYRD SIPHAACHKCIDFYSRIRELRHYSDSVYGDTLEKLTNTGLYNLLIRCLRCQKPLNPAE KLRHLNEKRRFHNIAGHYRGQCHSCCNRARQERLQRRRETQV |
| 7 | HPV viral replication protein E6 derived from HPV type 16 | MHQKRTAMFQDPQERPRKLPQLCTELQTTIHDIILECVYCKQQLLRREVYDFAFR DLCIVYRDGNPYAVCDKCLKFYSKISEYRHYCYSLYGTTLEQQYNKPLCDLLIRCINC QKPLCPEEKQRHLDKKQRFHNIRGRWTGRCMSCCRSSRTRRETQL |
| 8 | HPV viral replication protein E6 derived from HPV type 11 | MESKDASTSATSIDQLCKTFNLSLHTLQIQCVFCRNALTTAEIYAYAYKNLKVVWR DNFPFAACACCLELQGKINQYRHFNYAAYAPTVEEETNEDILKVLIRCYLCHKPLCE IEKLKHILGKARFIKLNNQWKGRCLHCWTTCMEDLLP |

| SEQ ID NO. | Description | Sequence |
|---|---|---|
| 9 | HPV viral replication protein E6 derived from HPV type 6A | MESANASTSATTIDQLCKTFNLSMHTLQINCVFCKNALTTAEIYSYAYKQLKVLFR GGYPYAACACCLEFHGKINQYRHFDYAGYATTVEEETKQDILDVLIRCYLCHKPLC EVEKVKHILTKARFIKLNCTWKGRCLHCWTTCMEDMLP |
| 10 | HPV viral replication protein E7 derived from HPV type 18 | MHGPKATLQDIVLHLEPQNEIPVDLLCHEQLSDSEEENDEIDGVNHQHLPARRAE PQRHTMLCMCCKCEARIKLVVESSADDLRAFQQLFLNTLSFVCPWCASQQ |
| 11 | HPV viral replication protein E7 derived from HPV type 16 | MHGDTPTLHEYMLDLQPETTDLYCYEQLNDSSEEEDEIDGPAGQAEPDRAHYNI VTFCCKCDSTLRLCVQSTHVDIRTLEDLLMGTLGIVCPICSQKP |
| 12 | HPV viral replication protein E7 derived from HPV type 11 | MHGRLVTLKDIVLDLQPPDPVGLHCYEQLEDSSEDEVDKVDKQDAQPLTQHYQI LTCCCGCDSNVRLVVECTDGDIRQLQDLLLGTLNIVCPICAPKP |
| 13 | HPV viral replication protein E7 derived from HPV type 6A | MHGRHVTLKDIVLDLQPPDPVGLHCYEQLVDSSEDEVDEVDGQDSQPLKQHFQI VTCCCGCDSNVRLVVQCTETDIREVQQLLLGTLDIVCPICAPKT |
| 14 | HPV viral replication protein E7 derived from HPV type 68 | MHGRHVTLKDIVLDLQPPDPVGLHCYEQLVDSSEDEVDEVDGQDSQPLKQHFQI VTCCCGCDSNVRLVVQCTETDIREVQQLLLGTLNIVCPICAPKT |

The HPV immunogen for use in the present invention can be prepared recombinantly (for example, in *E. coli*, mammalian cells or insect cells), synthetically (for example, using standard organic chemistry techniques, such as solution or solid phase peptide synthesis), or they may be prepared from polypeptides isolated from a native protein or peptide derived from an animal source, for example a human HPV positive tissue. Preferably, HPV immunogens for use in the present invention are prepared recombinantly (for example, in *E. coli*, mammalian cells or insect cells). More preferably, HPV immunogen for use in the present invention is prepared recombinantly in *E. coli*.

In one embodiment of the invention, the HPV immunogen for use in the present invention is in the form of a HPV immunogen composition comprising one or more HPV immunogens. For the avoidance of doubt, the one or more HPV immunogens present in a HPV immunogen composition as described herein may independently have any of the properties and/or characteristics of the HPV immunogens described herein.

HPV immunogens that have different amino acids sequences are referred to herein as the "different kinds". HPV immunogen kinds may be different because they have amino acid sequences that correspond to different HPV proteins or they have amino acid sequences that correspond to a part of a different HPV protein, or they have amino acid sequences that correspond to a different part of the same HPV protein. HPV immunogens that have the same amino acid sequence are referred to herein as the "same kind". Thus, in preferred embodiments of the invention, a HPV immunogen composition for use in the present invention comprises two or more different kinds of HPV immunogen (for example two or more, 10 or more, 100 or more, 1000 or more, 10,000 or more, 100,000 or more, or 500,000 or more different kinds of HPV immunogen). In another embodiment of the invention, a HPV immunogen composition comprises more than 10 different kinds of HPV immunogen (for example 100 or more, 1000 or more, 10,000 or more, 100,000 or more, or 500,000 different kinds of HPV immunogen). For example, such a HPV immunogen composition may comprise 2 to 10 different kinds of HPV immunogens (for example 2, 3, 4, 5, 6, 7, 8, 9 or 10). Preferably, such a HPV immunogen composition may comprises 2 to 9 different kinds of HPV immunogen (for example 2, 3, 4, 6, 7, 8 or 9).

HPV immunogen kinds that are different because they have amino acid sequences that correspond to different HPV proteins, or parts of different HPV proteins, may be different because they correspond to a HPV viral replication protein E (for example E1, E2, E3, E4, E5, E6 or E7) or a HPV coat protein L (for example, L1 or L2)) and/or may be different because they correspond to HPV proteins of different HPV types (for example HPV types 6, 11, 16, 18, 31, 33, 35, 39, 45, 51, 52, 56, 58, 59, 68, 73, 82, 26, 53 or 66, such as HPV types 6, 11, 16, 18, 31, 33, 45, 52 and 58).

In a preferred embodiment of the invention, the HPV immunogen composition comprises 9 different kinds of HPV immunogen. More preferably, the HPV immunogen composition comprises 9 different kinds of HPV immunogen each having an amino acid sequence corresponding to the amino acid sequence of a HPV coat protein L1 derived from HPV types 6, 11, 16, 18, 31, 33, 45, 52 and 58. In another preferred embodiment of the invention, the HPV immunogen composition comprises 4 different kinds of HPV immunogen. More preferably, the HPV immunogen composition comprises 4 different kinds of HPV immunogen each having an amino acid sequence corresponding to the amino acid sequence of a HPV coat protein L1 derived from a different one of HPV types 6, 11, 16 and 18. In another preferred embodiment of the invention, the HPV immunogen composition comprises 2 different kinds of HPV immunogen. More preferably, the HPV immunogen composition comprises 2 different kinds of HPV immunogen each having an amino acid sequence corresponding to the amino acid sequence of a HPV coat protein L1 derived from a different one of HPV types 6 and 11.

In another embodiment of the invention, the HPV immunogen composition comprises at least 2 different kinds of immunogen. More preferably, the HPV immunogen composition comprises at least 2 different kinds of HPV immunogen wherein at least one amino acid sequence corresponds to the amino acid sequence of a HPV coat protein L (for example, a HPV coat protein L1 or L2, and in particular a HPV coat protein L1, for example derived from HPV types 6, 11, 16, 18, 31, 33, 45, 52 and 58) and at least one amino acid sequence corresponds to the amino acid sequence of a HPV viral replication protein E (for example, a HPV viral replication protein E1, E2, E3, E4, E5, E6 or E7, in particular E6 or E7, for example derived from HPV types 6, 11, 16, 18, 31, 33, 45, 52 and 58).

In another embodiment of the invention, the HPV immunogen composition comprises at least 2 different kinds of immunogen. More preferably, the HPV immunogen composition comprises at least 2 different kinds of HPV immunogen corresponding to a HPV viral replication protein E (for example, a HPV viral replication protein E1, E2, E3, E4, E5, E6 or E7, in particular E6 or E7, for example derived from HPV types 6, 11, 16, 18, 31, 33, 45, 52 and 58). For example, wherein at least one amino acid sequence corresponds to the amino acid sequence of a HPV viral replication protein E6 (in particular a HPV viral replication protein E6 derived from HPV types 6, 11, 16, 18, 31, 33, 45, 52 and 58), and at least one amino acid sequence corresponds to the amino acid sequence of a HPV viral replication protein E7 (in particular a HPV viral replication protein E7 derived from HPV types 6, 11, 16, 18, 31, 33, 45, 52 and 58).

In another embodiment of the invention, the HPV immunogen composition comprises at least 3 different kinds of immunogen. More preferably, the HPV immunogen composition comprises at least 3 different kinds of HPV immunogen wherein at least one amino acid sequence corresponds to the amino acid sequence of a HPV coat protein L1 (in particular a HPV coat protein L1 or L2, and in particular a HPV coat protein L1, for example derived from HPV types 6, 11, 16, 18, 31, 33, 45, 52 and 58), at least one amino acid sequence corresponds to the amino acid sequence of a HPV viral replication protein E6 (in particular a HPV viral replication protein E6 derived from HPV types 6, 11, 16, 18, 31, 33, 45, 52 and 58), and at least one amino acid sequence corresponds to the amino acid sequence of a HPV viral replication protein E7 (in particular a HPV viral replication protein E7 derived from HPV types 6, 11, 16, 18, 31, 33, 45, 52 and 58).

In certain embodiments, the HPV immunogen composition comprises 4 different kinds of HPV immunogen each having an amino acid sequence corresponding to the amino acid sequence of a HPV coat protein L1 derived from SEQ ID NO. 1, SEQ ID NO. 2, SEQ ID NO. 3, SEQ ID NO. 4 and SEQ ID NO. 5. In another preferred embodiment of the invention, the HPV immunogen composition comprises 2 different kinds of HPV immunogen. More preferably, the HPV immunogen composition comprises 2 different kinds of HPV immunogen each having an amino acid sequence corresponding to the amino acid sequence of a HPV coat protein L1 derived from a different one of SEQ ID NO. 3, SEQ ID NO. 4 and SEQ ID NO. 5.

In each case, the HPV immunogen may be a protein or peptide having an amino acid sequence corresponding to a part of the amino acid sequence of a HPV protein. The part should have a length sufficient to be able to bring about a specific immune response. For example, the part has a length of at least 10 amino acids. For example, it is at least 15, at least 20, at least 25, at least 30, at least 35, at least 40, at least 45 or at least 50 amino acids long.

Thus, in certain embodiments the HPV immunogen may be a protein or peptide having an amino acid sequence corresponding to a part of the amino acid sequence of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, or SEQ ID NO. 14. The part should have a length sufficient to be able to bring about a specific immune response. For example, the part has a length of at least 10 amino acids. For example, it is at least 15, at least 20, at least 25, at least 30, at least 35, at least 40, at least 45 or at least 50 amino acids long.

A HPV immunogen compositions for use in the present invention may further comprise an adjuvant. The term "adjuvant" as used herein is to be understood as any substance that enhances an immune response towards an antigen. Examples of adjuvants for use in the present invention include dsRNA analogues, such as polyinosinic:polycytidylic acid, Incomplete Freund's Adjuvant, cytokines (for example, interleukins), CD40, keyhole limpet hemocyanin, Toll-like receptors, CpG oligodeoxynucleotides, saponins, aluminium salts (for example aluminium hydroxyphosphate sulphate, or aluminium hydroxide, hydrated ($Al(OH)_3$, for example with 3-O-desacyl-4'-monophosphoryl lipid A (MPL) adsorbed on its surface), colloidal alum, and analogues of lipid A of lipopolysaccharide.

The Phagocytosable Particle and the Core of the Phagocytosable Particle

A phagocytosable particle of the present invention is a particle able to be phagocytosed by cells of the immune system. It should be understood, however, that phagocytosable particles of the present invention may also be internalised by cells of the immune system via different routes (e.g. pinocytosis, clathrin-mediated endocytosis and non-clathrin-mediated endocytosis). Preferably, the phagocytosable particles are phagocytosable by an APC, for example a monocyte, dendritic cell, B-cell or macrophage, or other cells that either phagocytose or internalise extracellular molecules, such as antigens, and present antigen-derived peptides on MHC class II and/or MHC class I molecules to CD4+ T-cells and/or CD8+ T-cells.

Antigens that are internalised into an APC by the phagocytic route are degraded in a non-uniform manner, which subsequently leads to a wide variety of antigen-derived peptides being presented by the APC. Without wishing to be bound by theory, it is believed that the phagocytosable particles for use in the present invention bring about particularly effective activation and expansion of HPV immunogen specific T-cells because the HPV immunogen is phagocytosed by APCs, which subsequently leads to a wide variety of HPV immunogen-derived peptides being presented by the APC and thus particularly effective activation and expansion of HPV immunogen specific T-cells.

For a particle to be phagocytosed by a cell of the immune system, such as an APC, the particle needs to be within a size range suitable to allow for phagocytosis. For example, a particle that is too small may not trigger phagocytosis by a particular APC, or a particle that is too large may not be phagocytosable by a particular APC. Complete phagocytosis leads to good antigen degradation by APCs and subsequently good presentation to T-cells via the MHC class II pathway. The optimal size has been investigated by the current inventors (see Examples 3a and 3b, and FIGS. 1, 2A-C, and 3A-E).

A phagocytosable particle of the present invention comprises a core, and a HPV immunogen tightly associated to the core. Thus, the size of the core needs to be within a range such that when the core is tightly associated to a HPV immunogen, the core and the tightly associated HPV immunogen are phagocytosable by a cell of the immune system, and in particular an APC. It is preferred that the size of the core is within a range such that when the core is tightly associated to a HPV immunogen, the core and the tightly associated HPV immunogen are small enough that more than one phagocytosable particle can enter the same APC by phagocytosis. Having more than one phagocytosed particle in an APC maximises presentation of HPV immunogen fragments on the cell surface via the MHC class II pathway. Furthermore, it allows particles having different HPV immunogen (in particular HPV immunogens comprising different kinds of HPV immunogen) to enter an APC, which means that the APC can present different HPV immunogens from several particles in different phagosomes at the same.

As such, in one preferred embodiment, the core has a largest dimension of less than 6 μm, less than 5.6 μm, less than 4 μm, less than 3 μm, less than 2.5 μm, less than 2 μm or less than 1.5 μm. More preferably the core has a largest dimension of less 1.5 μm. In another preferred embodiment, the core may have a largest dimension of greater than 0.001 μm, greater than 0.005 μm, greater than 0.01 μm, greater than 0.05 μm, greater than 0.1 μm, greater than 0.2 μm or greater than 0.5 μm. More preferably the core has a largest dimension of greater than 0.5 μm.

In one especially preferred embodiment, the core has a largest dimension in the range of 0.1 to 6 μm, for example 0.1 to 5.6 μm, 0.2 to 5.6 μm, 0.5 to 5.6 μm, 0.1 to 4 μm or 0.5 to 4 μm. More preferably the core has a largest dimension in the range of 0.1 to 3 μm, for example, 0.5 to 3 nm, 0.2 to 2.5 nm, 0.5 to 2.5 nm, 0.2 to 2 nm, 0.5 to 2 μm or 1 to 2 nm. Even more preferably, the core has a largest dimension of about 1 μm, about 1.5 μm or about 2 μm. In a very preferred embodiment of the invention, the core is about 1 μm.

The core of the phagocytosable particle of the invention takes the form of any three-dimensional shape, for example any regular or irregular three-dimensional shape. Preferably, the phagocytosable particle is substantially spherical, in which case the dimensions of the phagocytosable particle refers to diameter.

The core of a phagocytosable particle may comprise a polymer, glass, ceramic material (e.g. the core may be a polymer particle, a glass particle or a ceramic particle). The material of the core may be a biodegradable and/or biocompatible material (e.g. the particle may be a biodegradable and/or biocompatible particle).

Preferably, the core comprises a polymer (for example, the core is a polymer particle). If the core comprises a polymer, it may be selected from the group consisting of a synthetic aromatic polymer (such as polystyrene e.g. the core is a polystyrene particle), a synthetic non-aromatic polymer (such as polyethylene, polylactic acid, poly(lactic-co-glycolic acid) and polycaprolactone, e.g. the core is a polyethylene particle, polylactic acid particle, poly(lactic-co-glycolic acid) particle or polycaprolactone particle), a naturally occurring polymer (such as collagen, gelatine, proteins (e.g. virus-like particles), lipids or albumin, e.g. the core is a collagen particle, gelatine particle or albumin particle), a polymeric carbohydrate molecule (such as a polysaccharide, for example agarose, alginate, chitosan or zymosan e.g. the core is an agarose particle, alginate particle, chitosan particle or zymosan particle).

In one preferred embodiment, the core comprises polystyrene or polyethylene, and more preferably comprises polystyrene (e.g. the core is a polystyrene particle). Such polymers are biocompatible.

The present inventors have found that polystyrene particles are a particularly useful core for a phagocytosable particle of the present invention because they are nontoxic and are widely commercially available in various sizes and in various functionalisable forms. Furthermore, the present inventors have found phagocytosable particles comprising a polystyrene core, such as a polystyrene particle, are able to withstand stringent sterilisation procedures to prepare the particles for administration to a subject. Such sterilisation procedures may include repeated washed with acid or alkali solutions and/or exposure to high temperatures.

In one very preferred embodiment of the invention, the core is a polystyrene particle with a largest dimension of less than 6 μm, preferably from about 1 μm to about 3 μm, and more preferably about 1 μm. Phagocytosable particles comprising a polystyrene particle core with a dimension of about 1 μm to about 3 μm, and especially about 1 μm, are efficiently phagocytosed by APCs and are also able to withstand stringent sterilisation procedures to remove pathogens (e.g. bacteria, fungus and viruses) and antigenic contaminants, such as pyrogens (e.g. endotoxins), which may be associated to the core or HPV immunogen.

In one embodiment of the invention, the core has magnetic properties. For example, the core may have paramagnetic or superparamagnetic properties. Preferably, the core has superparamagnetic properties.

An example of a superparamagnetic core suitable for use with the invention are Dynabeads™ (Invitrogen). Dynabeads™ are available in various functionalisable forms, for example Dynabeads M-270 Carboxylic acid, Dynabeads M-270 Amine, and Dynabeads MyOne Carboxylic acid. Dynabeads™ are monosized superparamagnetic particles, which are composed of highly cross-linked polystyrene with evenly distributed magnetic material. The magnetic material may be iron oxide. Other examples of magnetic cores, in particular superparamagnetic cores, include Encapsulated Carboxylated Estapor® SuperParamagnetic Microspheres (Merck Chimie S.A.S.) and Sera-Mag SpeedBeads (hydrophilic) Carboxylate-Modified Magnetic particles (GE Healthcare UK Limited). Encapsulated Carboxylated Estapor® SuperParamagnetic Microspheres are made of a core-shell structure which encapsulates an iron oxide core. Preferably, the core is a Sera-Mag SpeedBeads (hydrophilic) Carboxylate-Modified Magnetic particle (GE Healthcare UK Limited).

A phagocytosable particle of the present invention comprises a HPV immunogen tightly associated to the core. A HPV immunogen may be tightly associated to a core using a variety of means. For example, the HPV immunogen may be attached to a core by a covalent bond, for example an amide bond between an amine group or a carboxylic acid group of the HPV immunogen and a carboxylic acid group or an amine group on the surface of the core. Alternatively, a HPV immunogen may be linked to a core via a metal chelate. For example, cores linked with a metal chelating ligand, such as iminodiacetic acid can bind metal ions such as $Cu^{2+}$, $Zn^{2+}$, $Ca^{2+}$, $Co^{2+}$ or $Fe^{3+}$. These metal chelates can in turn bind proteins and peptides containing for example histidine or cysteine with great strength. Thus, cores with metal chelates can non-covalently bind to a HPV immunogen. Preferably, the HPV immunogen is covalently attached to the core. One example of associating a polypeptide, such as a HPV immunogen, to the core is shown in Example 1.

A phagocytosable particle of the present invention comprises a core, and a HPV immunogen tightly associated to the core. A phagocytosable particle of the invention may comprise one or more HPV immunogens associated to the core. For example, a phagocytosable particle of the invention may comprise 1 to 3 million HPV immunogens, preferably 1 to 2 million HPV immunogens, and more preferably 1 to 1 million HPV immunogens, for example 1 to 800,000, 1 to 500,000, 1 to 100,000, 1 to 10,000, 1 to 1000, 1 to 100, or 1 to 10 HPV immunogens; or for example 10 to 1 million, 100 to 1 million, 1000 to 1 million, 10,000 to 1 million, 100,000 to 1 million, or 500,000 to 1 million. Preferably a phagocytosable particle of the invention may comprise 500,000 to 1 million HPV immunogens.

In preferred embodiments, to maximise the delivery of HPV immunogen into an APC (which can then be cleaved from the phagocytosable particle and processed by an APC, thus resulting in the presentation of a wide variety of HPV-derived peptides on the surface of the APCs), a phagocytosable particle of the invention may comprise more than one (i.e. two or more, for example two to 3 million) HPV immunogen associated to the core. For example, phagocytosable particle of the invention may comprise a 2 to 1 million HPV immunogens tightly associated to a core (for example 2 to 800,000, 2 to 500,000, 2 to 100,000, 2 to 10,000, 2 to 1000, 2 to 100, or 2 to 10 HPV immunogens tightly associated to a core). Preferably, a phagocytosable particle of the invention comprises 10 or more HPV immunogens tightly associated to a core, such as 10 to 1 million HPV immunogens tightly associated to a core (for example 10 to 800,000, 10 to 500,000, 10 to 100,000, 10 to 10,000, 10 to 1000, or 10 to 100 HPV immunogens tightly associated to a core). More preferably a phagocytosable particle of the invention comprises 100 or more HPV immunogens tightly associated to a core, such as 100 to 1 million HPV immunogens tightly associated to a core (for example 100 to 800,000, 100 to 500,000, 100 to 100,000, 100 to 10,000, or 100 to 1000 HPV immunogens tightly associated to a core). In certain embodiments a phagocytosable particle of the invention comprises 1000 or more HPV immunogens tightly associated to a core, such as 1000 to 1 million HPV immunogens tightly associated to a core (for example 1000 to 800,000, 1000 to 500,000, 1000 to 100,000, or 1000 to 10,000 HPV immunogens tightly associated to a core). In certain embodiments a phagocytosable particle of the invention comprises 10,000 or more HPV immunogens tightly associated to a core, such as 10,000 to 1 million HPV immunogens tightly associated to a core (for example 10,000 to 800,000, 10,000 to 500,000, or 10,000 to 100,000 HPV immunogens tightly associated to a core). In certain embodiments a phagocytosable particle of the invention comprises 100,000 or more HPV immunogens tightly associated to a core, such as 100,000 to 1 million HPV immunogens tightly associated to a core (for example 100,000 to 800,000 or 100,000 to 500,000 HPV immunogens tightly associated to a core).

In embodiments of the invention, where a phagocytosable particle of the invention may comprise more than one HPV immunogen associated to the core (for example 2 or more, 10 or more, 100 or more, 1000 or more, 10,000 or more, 100,000 or more, or 500,000 or more HPV immunogens associated to the core), the HPV immunogen associated to the core may be the same kind, or may be different kinds (i.e. some or all of the HPV immunogens associated to the core may be different kinds).

Phagocytosable particles comprising two or more different kinds of HPV immunogens are able to deliver a wide variety of HPV immunogens into an APC and thus increase the variety of HPV-derived peptides that are presented by the APC. The present inventors have found that this significantly improves the activation and expansion of HPV immunogen specific T-cells that are able to target cancer cells.

A phagocytosable particle comprising more than one HPV immunogen associated to the core (for example two or more, 10 or more, 100 or more, 1000 or more, 10,000 or more, 100,000 or more, or 500,000 or more HPV immunogens associated to the core) of the invention can comprise one kind of HPV immunogen tightly associated to a core (i.e. all the HPV immunogens tightly associated to the core are the same). In one embodiment of the invention, a phagocytosable particle comprises 100,000 to 1 million HPV immunogens tightly associated to a core, wherein the 100,000 to 1 million HPV immunogens are the same kind of HPV immunogen. Preferably, the HPV immunogen has an amino acid sequence corresponding to the amino acid sequence of an HPV protein selected from HPV viral replication proteins E1, E2, E3, E4, E5, E6 and E7 and the HPV coat proteins L1 and L2 derived from any one of HPV types 16, 18, 31, 33, 35, 39, 45, 51, 52, 56, 58, 59, 68, 73, 82, 26, 53 or 66. More preferably, the HPV immunogen has an amino acid sequence corresponding to the amino acid sequence of a HPV protein selected from HPV viral replication proteins E1, E2, E3, E4, E5, E6 and E7 and the HPV coat proteins L1 and L2 derived from any one of HPV types 16, 18, 31, 33, 35, 39, 45, 51, 52, 56, 58, 59, 68, 73 or 82. More preferably, the HPV immunogen has an amino acid sequence corresponding to the amino acid sequence of a HPV protein selected from HPV viral replication proteins E1, E2, E3, E4, E5, E6 and E7 and the HPV coat proteins L1 and L2 derived from any one of HPV types 6, 11, 16, 18, 31, 33, 45, 52 and 58. For example, the HPV immunogen has an amino acid sequence corresponding to the amino acid sequence of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14 or SEQ ID NO. 15. More preferably, the HPV immunogen has an amino acid sequence corresponding to the amino acid sequence of a HPV protein selected the HPV coat protein L1 derived from any one of HPV types 6, 11, 16, 18, 31, 33, 45, 52 and 58. For example, the HPV immunogen has an amino acid sequence corresponding to the amino acid sequence of SEQ ID NO. 1, SEQ ID NO. 2, SEQ ID NO. 3, SEQ ID NO. 4, or SEQ ID NO. 5.

In another embodiment of the invention, a phagocytosable particle comprising more than one HPV immunogen associated to the core (for example two or more, 10 or more, 100 or more, 1000 or more, 10,000 or more, 100,000 or more, or 500,000 or more associated to the core) can comprise two different kinds of HPV immunogen tightly associated to a core. For example, a phagocytosable particle comprising more than 10 HPV immunogens associated to the core (for example 100 or more, 1000 or more, 10,000 or more, 100,000 or more, or 500,000 or more HPV immunogens associated to the core) can comprise two or more different kinds of HPV immunogen tightly associated to a core. For example, such a phagocytosable particle may comprise two or more different kinds of HPV immunogen (for example two or more, 10 or more, 100 or more, 1000 or more, 10,000 or more, 100,000 or more, or 500,000 or more different kinds of HPV immunogen). Preferably, each of the two or more different kinds of HPV immunogen has an amino acid sequence corresponding to the amino acid sequence of a HPV protein selected from HPV viral replication proteins E1, E2, E3, E4, E5, E6 and E7 and the HPV coat proteins L1 and L2 derived from any one of HPV types 16, 18, 31, 33, 35, 39, 45, 51, 52, 56, 58, 59, 68, 73, 82, 26, 53 or 66. More preferably, each of the two or more different kinds of HPV immunogen has an amino acid sequence corresponding to the amino acid sequence of a HPV protein selected from HPV viral replication proteins E1, E2, E3, E4, E5, E6 and E7 and the HPV coat proteins L1 and L2 derived from any one of HPV types 16, 18, 31, 33, 35, 39, 45, 51, 52, 56, 58, 59, 68, 73 or 82. More preferably, each of the two or more different kinds of HPV immunogen has an amino acid sequence corresponding to the amino acid sequence of a HPV protein selected from HPV viral replication proteins E1, E2, E3, E4, E5, E6 and E7 and the HPV coat proteins L1 and L2 derived from any one of HPV types 6, 11, 16, 18, 31, 33, 45, 52 and 58. More preferably, each of the two or more different kinds of HPV immunogen has an amino acid sequence corresponding to the amino acid sequence of a HPV protein selected the HPV coat protein L1 derived from any one of HPV types 6, 11, 16, 18, 31, 33, 45, 52 and 58.

In preferred embodiments of the invention, a phagocytosable particle comprising more than one HPV immunogen associated to the core (for example two or more, 10 or more, 100 or more, 1000 or more, 10,000 or more, 100,000 or more, or 500,000 or more HPV immunogens associated to the core) comprises 9 different kinds of HPV immunogen. More preferably, the phagocytosable particle comprises 9 different kinds of HPV immunogen each having an amino acid sequence corresponding to the amino acid sequence of a HPV coat protein L1 derived from HPV types 6, 11, 16, 18, 31, 33, 45, 52 and 58. In another preferred embodiment of the invention, a phagocytosable particle comprising more than one HPV immunogen associated to the core (for example two or more, 10 or more, 100 or more, 1000 or more, 10,000 or more, 100,000 or more, or 500,000 or more HPV immunogens associated to the core) comprises 4 different kinds of HPV immunogen. More preferably, the phagocytosable particle comprises 4 different kinds of HPV immunogen each having an amino acid sequence corresponding to the amino acid sequence of a HPV coat protein L1 derived from HPV types 6, 11, 16 and 18. In another preferred embodiment of the invention, a phagocytosable particle comprising more than one HPV immunogen associated to the core (for example two or more, 10 or more, 100 or more, 1000 or more, 10,000 or more, 100,000 or more, or 500,000 or more HPV immunogens associated to the core) comprises 2 different kinds of HPV immunogen. More preferably, the phagocytosable particle comprises 2 (or 3, or 4) different kinds of HPV immunogen each having an amino acid sequence corresponding to the amino acid sequence of a HPV coat protein L1 derived from HPV types 6 and 11.

In each case, the HPV immunogen may be a protein or peptide having an amino acid sequence corresponding to a part of the amino acid sequence of a HPV protein (for example, corresponding to a part of the amino acid sequence of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14 or SEQ ID NO. 15, and in particular a part of SEQ ID NO. 1, SEQ ID NO. 2, SEQ ID NO. 3, SEQ ID NO. 4 or SEQ ID NO. 5). The part should have a length sufficient to be able to bring about a specific immune response. For example, the part has a length of at least 10 amino acids. For example, it is at least 15, at least 20, at least 25, at least 30, at least 35, at least 40, at least 45 or at least 50 amino acids long. The part may optionally have a length of less than or equal to 600 amino acids. For example, it is less than or equal to 500, less than or equal to 400, less than or equal to 300, less than or equal to 200, less than or equal to 100, less than or equal to 75, less than or equal to 60 or less than or equal to 50 amino acids. For example, the part may have a length of 15, 20, 25, 30, 35, 40, 45, 50, 55, 60, 65, 70, 85, 90, 95, 100, 120, 130, 140, 150, 160, 170, 180, 190, 200, 250, 300, 350, 400, 450, 500, 550 or 600 amino acids. If the phagocytosable particle comprises two different kinds of HPV immunogen tightly associated to a core, each different kind may be a protein or peptide having an amino acid sequence of the same length or an amino acid sequence of a different length.

The present invention also provides a phagocytosable particle composition comprising a phagocytosable particle of the invention. A phagocytosable particle composition of the invention comprising a phagocytosable particle as described herein may comprise one or more phagocytosable particles. Preferably, it comprises more than one particle. In such embodiments, the phagocytosable particles may be the same, or they may be different. Phagocytosable particles may be different due to the core and/or may be different due to comprising different types of HPV immunogens tightly associated to the core. Preferably, in a composition comprising phagocytosable particles of the invention in which the phagocytosable particles are different, the phagocytosable particles have the same core and are different due to the particles comprising different types of HPV immunogen tightly associated to the core.

Phagocytosable particles having different cores (e.g. cores having different sizes and/or comprising different materials/polymers as described herein) are referred to herein as phagocytosable particles of a "different set". Phagocytosable particles having the same core (e.g. cores having the same size and comprising the same materials/polymer) may be referred to herein as phagocytosable particles of the "same set".

Phagocytosable particles that have the same core (i.e. they are of the same phagocytosable particle set), but that are different due to having different kind(s) of HPV immunogen construct tightly associated to the core, are referred to herein as phagocytosable particles of "different groups". Phagocytosable particles that have the same core and the same kind(s) of HPV immunogen tightly associated to the core are referred to herein as phagocytosable particles of the "same group".

In one embodiment, a phagocytosable particle composition of the invention comprises one phagocytosable particle set which consists of one phagocytosable particle group (i.e. all of the phagocytosable particles in the composition are the same). Alternatively, a phagocytosable particle composition of the invention can comprise one phagocytosable particle set which comprises two or more different groups of phagocytosable particle (for example 2, 3, 4, 5, 6, 7, 8, 9, 10, 12, 16, 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or more phagocytosable particle groups). In another embodiment, a phagocytosable particle composition of the invention can comprise one phagocytosable particle set which comprises 2 to 75 different groups of phagocytosable particle (for example 2, 3, 4, 5, 6, 7, 8, 9, 10, 12, 15, 18, 20, 25, 30, 35, 40, 45, 50, 55, 60, 65, 70 or 75 phagocytosable particle groups). In another embodiment, a phagocytosable particle composition of the invention can comprise one phagocytosable particle set which comprises 2 to 40 different groups of phagocytosable particle (for example 2, 3, 4, 5, 6, 7, 8, 9, 10, 12, 14, 16, 18, 20, 22, 24, 26, 28, 30, 32, 34, 36, 38 or 40 phagocytosable particle groups). In another embodiment, a phagocytosable particle composition of the invention can comprise one phagocytosable particle set which comprises 2 to 18 different groups of phagocytosable particle (for example 2, 3, 4, 5, 6, 7, 8, 9, 10, 11, 12, 13, 14, 15, 16, 17 or 18 phagocytosable particle groups). In another embodiment, a phagocytosable particle composition of the invention can comprise one phagocytosable particle set which comprises 2 to 15 different groups of phagocytosable particle (for example 2, 3, 4, 5, 6, 7, 8, 9, 10, 11, 12, 13, 14 or 15 phagocytosable particle groups). In another embodiment, a phagocytosable particle composition of the invention can comprise one phagocytosable particle set which comprises 2 to 9 different groups of phagocytosable particle (for example 2, 3, 4, 5, 6, 7, 8 or 9 phagocytosable particle groups). In another embodiment, a phagocytosable particle composition of the invention can comprise one phagocytosable particle set which comprises 2 to 4 different groups of phagocytosable particle (for example 2, 3 or 4 phagocytosable particle groups).

In one embodiment, a phagocytosable particle composition of the invention can comprise two or more different phagocytosable particle sets (i.e. each set having different cores, for example each set having cores of different sizes and/or comprising different materials as described herein) and each set can consist of one phagocytosable particle group. For example, the phagocytosable particle composition of the invention may comprise 2, 3, 4, 5, 6, 7, 8 or 9 phagocytosable particle sets and each set can consist of one phagocytosable particle group.

In one embodiment of the invention, a phagocytosable particle composition of the invention can comprise two or more different phagocytosable particle sets (for example 2, 3, 4, 5, 6, 7, 8 or 9 phagocytosable particle sets) and each set can comprise of two or more different phagocytosable particle group (for example 2, 3, 4, 5, 6, 7, 8, 9, 10, 12, 16, 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or more phagocytosable particle groups). In another embodiment of the invention, a phagocytosable particle composition of the invention can comprise two or more different phagocytosable particle sets (for example 2, 3, 4, 5, 6, 7, 8 or 9 phagocytosable particle sets) and each set can comprise of 2 to 75 different groups of phagocytosable particle (for example 2, 3, 4, 5, 6, 7, 8, 9, 10, 12, 15, 18, 20, 25, 30, 35, 40, 45, 50, 55, 60, 65, 70 or 75 phagocytosable particle groups). In another embodiment of the invention, a phagocytosable particle composition of the invention can comprise two or more different phagocytosable particle sets (for example 2, 3, 4, 5, 6, 7, 8 or 9 phagocytosable particle sets) and each set can comprise of 2 to 40 different groups of phagocytosable particle (for example 2, 3, 4, 5, 6, 7, 8, 9, 10, 12, 14, 16, 18, 20, 22, 24, 26, 28, 30, 32, 34, 36, 38 or 40 phagocytosable particle groups). In another embodiment of the invention, a phagocytosable particle composition of the invention can comprise two or more different phagocytosable particle sets (for example 2, 3, 4, 5, 6, 7, 8 or 9 phagocytosable particle sets) and each set can comprise of 2 to 18 different groups of phagocytosable particle (for example 2, 3, 4, 5, 6, 7, 8, 9, 10, 11, 12, 13, 14, 15, 16, 17 or 18 phagocytosable particle groups). In another embodiment of the invention, a phagocytosable particle composition of the invention can comprise two or more different phagocytosable particle sets (for example 2, 3, 4, 5, 6, 7, 8 or 9 phagocytosable particle sets) and each set can comprise of 2 to 15 different groups of phagocytosable particle (for example 2, 3, 4, 5, 6, 7, 8, 9, 10, 11, 12, 13, 14 or 15 phagocytosable particle groups). In another embodiment of the invention, a phagocytosable particle composition of the invention can comprise two or more different phagocytosable particle sets (for example 2, 3, 4, 5, 6, 7, 8 or 9 phagocytosable particle sets) and each set can comprise of 2 to 9 different groups of phagocytosable particle (for example 2, 3, 4, 5, 6, 7, 8 or 9 phagocytosable particle groups). In another embodiment of the invention, a phagocytosable particle composition of the invention can comprise two or more different phagocytosable particle sets (for example 2, 3, 4, 5, 6, 7, 8 or 9 phagocytosable particle sets) and each set can comprise of 2 to 4 different groups of phagocytosable particle (for example 2, 3 or 4 phagocytosable particle groups).

For the avoidance of doubt, in phagocytosable particle compositions in embodiments having more than one group of phagocytosable particle and more than one set of phagocytosable particle, each group of a phagocytosable particle set is independent from each group of another phagocytosable particle set. Thus, a group from one phagocytosable particle set can have the same kind(s) of HPV immunogen as a group from another phagocytosable particle set. Alternatively, a group from one phagocytosable particle set can have HPV immunogens that are a different kind(s) to those of a group from another phagocytosable particle set.

Sterilisation of the Phagocytosable Particles

It has been found that phagocytosable particles comprising a core and a HPV immunogen tightly associated to the core, may be efficiently washed and sterilised before administration to a subject. This is particularly advantageous because the washed and sterilised phagocytosable particles comprise lower levels pathogens (e.g. bacteria, fungus and viruses) and other antigenic contaminants such as pyrogens (e.g. endotoxins). Such contaminants can elicit non-specific immune responses in the subject. Washing and sterilising phagocytosable particles of the invention before administration to APCs (i.e. contacting the phagocytosable particles with APCs) therefore improves their safety and efficacy.

In one embodiment of the invention, the phagocytosable particle comprises a magnetic core, for example a paramagnetic or superparamagnetic core. A phagocytosable particle comprising a magnetic core, can be collected and/or held in place by a magnet. It is also possible to perform a wash by other means, such as by holding the phagocytosable particles (whether paramagnetic or not) in a column, or sedimenting the particles by gravity or by centrifugation.

The particular manner of the wash is not critical in the context of the present invention. For instance, the wash may involve subjecting a phagocytosable particle to a high pH, to a low pH, to a high temperature, to a sterilising/denaturing agent or a combination thereof.

The wash may involve subjecting the phagocytosable particle to alkali, preferably a strong alkali, for example at least 0.1M, 0.5M, 1M, 2M, 3M, 4M, 5M, 6M, 7M or 8M alkali. Preferably, the wash may involve subjecting the phagocytosable particle to at least 1M sodium hydroxide (NaOH), for example at least 2M NaOH. Preferably, the wash involves subjecting the phagocytosable particle to a high pH of at least 13.0, more preferably at least 14.0, most preferably at least 14.3. Other alkalis that may be used include, but are not limited to: lithium hydroxide (LiOH), potassium hydroxide, (KOH), rubidium hydroxide (RbOH), cesium hydroxide (CsOH), magnesium hydroxide (Mg(OH)$_2$), calcium hydroxide (Ca(OH)$_2$), strontium hydroxide (Sr(OH)$_2$), and barium hydroxide (Ba(OH)$_2$). Preferably, the wash involves subjecting the phagocytosable particle to a high pH of at least 13.0, more preferably at least 14.0, most preferably at least 14.3.

The wash may also involve subjecting the phagocytosable particle to an acid, preferably a strong acid, for example at least 0.1M, 0.5M, 1M, 2M, 3M, 4M, 5M, 6M, 7M or 8M acid. Preferably, the wash may involve subjecting the phagocytosable particle to at least 1M hydrochloric acid (HCl), for example at least 2M HCl. Other acids that may be used include, but are not limited to: hydroiodic acid (HI), hydrobromic acid (HBr), perchloric acid (HClO$_4$), nitric acid (HNO$_3$) and sulfuric acid (H$_2$SO$_4$).

The wash may also involve subjecting the phagocytosable particle to further sterilising/denaturing agents, such as urea and/or guanidine-HCl.

Preferably, the wash results in the phagocytosable particle being aseptic and/or sterile. More preferably, the wash results in the phagocytosable particle being sterile. Aspetic as defined herein is being free from pathogens (i.e. disease-causing microorganisms and viruses). Sterile is defined herein as being free from all biological contaminants. Preferably, the wash also removes antigenic contaminants such as pyrogens (e.g. endotoxins) from the phagocytosable particle. Preferably, the wash provides the phagocytosable particle with an endotoxin contamination of less than 100 pg/ml, preferably less than 50 pg/ml, more preferably less than 25 pg/ml and most preferably less than 10 pg/ml. Thus, in a preferred embodiment of the invention the phagocytosable particle is sterile and has an endotoxin contamination of less than 100 pg/ml.

A particular advantage of the wash is that the conditions may be selected such that the phagocytosable particle is both sterilized and denatured in a single step. In particular, a high pH wash (e.g. pH>14) can conveniently, simultaneously and quickly, sterilise the phagocytosable particle and eliminate a sufficient quantity of endotoxin and other antigenic contaminants.

The wash may comprise a single wash or several repeated washes, such as 2, 3, 4 or 5 washes. In addition, or alternatively, the phagocytosable particle may be subjected to a high temperature, such as at least 90° C., preferably at least 92° C., more preferably at least 95° C., for example at least 100° C. or at least 110° C.

The present inventors have advantageously found that when a HPV immunogen is associated to a core by a covalent bond, the phagocytosable particle can withstand stringent sterilisation and washing procedures that reduce the amount of pathogens (e.g. bacteria, fungus and viruses) and other antigenic contaminants such as pyrogens (e.g. endotoxins), that may be bound to a HPV immunogen or core. This means that the phagocytosable particles described herein are especially suitable for use in the present method of expanding HPV immunogen specific T-cells for use in the treatment or prophylaxis of cancer.

Kits of the Invention

The invention further provides a kit comprising phagocytosable particle of the invention and reagents suitable for use in expanding a T-cell population. The kit may further comprise reagents for assisting in expanding a T-cell population, such as IL-2. It may optionally also comprise IL-7 and/or IL-15. The kit may further comprise reagents for sterilising the phagocytosable particles of the invention.

The invention further provides a kit comprising a core as described herein, coupling reagents for coupling one or more HPV immunogens to the core, and reagents suitable for use in expanding a T-cell population.

The kit may further comprise one or more HPV immunogens or reagents for producing HPV immunogens, for example ready-to-use vectors adjusted for different cloning and expression conditions, or that comprise a cDNA sequence encoding one or more HPV immunogens. The one or more HPV immunogens in the kit may include the immunogenic peptide components of a commercially available vaccine composition, for example it may contain one or more of the components of a composition sold under the name Gardasil®, Gardasil 9° or Cervarix®. For example, in one embodiment the kit may comprise immunogenic peptide components selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14 and SEQ ID NO. 15.

Ex-Vivo Activation and Expansion of HPV Immunogen Specific T-Cells

The method of the invention includes the provision of APCs in step ii and T-cells in step iv. The T-cells are T-cells that have been harvested from a subject having a HPV positive cancer. The T-cell sample is therefore expected to contain T-cells that are HPV immunogen specific. They are generally present at only a low level.

The harvested APCs must be compatible with the HPV immunogen specific T-cells, such that they are capable of presenting antigens to the HPV immunogen specific T-cells in an antigen-specific context (MHC restricted) that the HPV immunogen specific T-cells can react to.

The APCs and HPV immunogen specific T-cells are preferably obtained from the same species and donor-matched with respect to MHC receptors. However, use of genetically engineered APCs from a different species is also envisioned. More preferably the APCs and HPV immunogen specific T-cells are obtained from the same subject. If the APCs and HPV immunogen specific T-cells are derived from the same subject, any potential for a mismatch between the APCs and HPV immunogen specific T-cells is avoided.

The APCs harvested from a subject may comprise phagocytes, monocytes and/or dendritic cells. The HPV immunogen specific T-cells may comprise CD4+ and/or CD8+ T-cells.

The APCs and HPV immunogen specific T-cells may be harvested from a blood sample derived from a subject. Preferably, the blood sample is a peripheral blood mononuclear cell (PBMC) sample. Obtaining PBMCs from peripheral blood samples is a routine protocol, which provides a convenient source for both APCs and T-cells at the same time and from the same subject. The PBMC sample may be freshly used or it may be subjected to freezing for storage before use. PBMCs are a fraction of human blood prepared by density gradient centrifugation of whole blood. The PBMCs mainly consists of lymphocytes (70-90%) and monocytes (10-30%), while red blood cells, granulocytes and plasma have been removed. Monocytes may in some instances make up 10 to 20% of the cell numbers in a PBMC sample, for example 10 to 15%.

APCs and HPV immunogen specific T-cells may also may be derived from a tumour of the subject, for example a sample derived from a lymphatic vessel in a tumour or a tumour draining lymph node (sometimes referred to as a sentinel node). Preferably, the APCs and HPV immunogen specific T-cells are harvested from a HPV positive tumour and/or a sentinel node associated with a HPV positive cancer in a subject.

Preferably, the APCs and HPV immunogen specific T-cells are harvested from the same sample derived from the subject and/or the same tumour of the subject. Alternatively, or additionally, APCs and HPV immunogen specific T-cells may be harvested from different samples derived from the subject. For example, the APCs may be harvested from a blood sample and the HPV immunogen specific T-cells may be harvested from a tumour and/or a sentinel node.

In the expansion method of the invention, the harvested APCs are contacted with a HPV immunogen (optionally tightly associated with a core as part of a phagocytosable particle). The HPV immunogen may be at a concentration of 0.01 µg/ml to 1000 µg/ml, 0.01 µg/ml to 100 µg/ml, 0.01 µg/ml to 10 µg/ml or 0.01 µg/ml to 1 µg/ml. For example, the dose may be 0.1 µg/ml to 1000 µg/ml, 0.1 µg/ml to 750 µg/ml, 0.1 µg/ml to 500 µg/ml, 0.1 µg/ml to 400 µg/ml, 0.1 µg/ml to 300 µg/ml, 0.1 µg/ml to 200 µg/ml, 0.1 µg to 100 µg, 0.1 µg to 50 µg/ml, 0.1 µg/ml to 40 µg/ml, 0.1 µg/ml to 30 µg/ml, 0.1 µg/ml to 20 µg/ml, 0.1 µg/ml to 10 µg/ml or 0.1 µg/ml to 10 µg/ml, 0.1 µg/ml to 9 µg/ml 0.1 µg/ml to 8 µg/ml 0.1 µg/ml to 7 µg/ml 0.1 µg/ml to 6 µg/ml 0.1 µg/ml to 5 µg/ml, 0.1 µg/ml to 4 µg/ml, 0.1 µg/ml to 3 µg/ml, 0.1 µg/ml to 2 µg/ml or 0.1 µg/ml to 1 µg/ml. Preferably, 0.1, 0.2, 0.3, 0.4, 0.5, 0.6, 0.7, 0.8, 0.9 or 1 µg/ml.

In one embodiment, the harvested APCs are contacted with a phagocytosable particle comprising a core and an HPV immunogen tightly associated to the core. The T-cell expansion method may comprise contacting APCs with 100 to $1 \times 10^9$ phagocytosable particles, for example 100 to $1 \times 10^8$, for example 100 to $1 \times 10^7$ phagocytosable particles are used in a given expansion run, for example 1000 to $1 \times 10^7$ phagocytosable particles. For example, the ratio of phagocytosable particle to APC is in the range 1000:1 to 1:10. The ratio can be optimised depending on the size of the phagocytosable particle. For example, for a phagocytosable particle with a largest diameter of about 1 µm, the ratio may be in the range 50:1 to 2:1, for example 25:1 to 5:1, 15:1 to 7:1, or 10:1.

In some embodiments, the phagocytosable particle provided in step i) is a phagocytosable particle of the present invention and may have any of the properties and/or characteristics of the phagocytosable particles of the present invention described herein.

In one embodiment of the invention, the in vitro T-cell expansion method comprises adding low doses IL-2 to the HPV immunogen specific T-cell sample, for example greater than 1.25 U/ml (for example 1.25 U/ml, 2.5 U/ml, 5 U/ml, or 50 U/ml), preferably greater than 2.5 U/ml, 5 U/ml, or 50 U/ml. Antigen specific T-cell expansion occurs in the presence of the antigen-presenting cell when IL-2 is simultaneously present. The IL-2 promotes the differentiation of HPV immunogen specific T-cells into effector HPV immunogen specific T-cells and into memory HPV immunogen specific T-cells. Following expansion of HPV immunogen specific T-cells, the APCs may be removed from the expanded T-cell population, for example by magnetic separation.

In another embodiment of the invention, the method of expanding HPV immunogen specific T-cells comprises adding IL-2 and/or IL-7 and/or IL-15 to the HPV immunogen specific T-cell sample, for example a low dose of IL-2 to the HPV immunogen specific T-cell sample, for example greater than 1.25 U/ml (for example 1.25 U/ml, 2.5 U/ml, 5 U/ml, or 50 U/ml), preferably greater than 2.5 U/ml, 5 U/ml, or 50 U/ml of IL-2, with optional addition of IL-7 and/or IL-15. For example a low dose of IL-7 to the HPV immunogen specific T-cell sample, for example greater than 1.25 U/ml (for example 1.25 U/ml, 2.5 U/ml, 5 U/ml, or 50 U/ml), preferably greater than 2.5 U/ml, 5 U/ml, or 50 U/ml of IL-7; and/or for example, a low dose of IL-15 to the HPV immunogen specific T-cell sample, for example greater than 1.25 U/ml (for example 1.25 U/ml, 2.5 U/ml, 5 U/ml, or 50 U/ml), preferably greater than 2.5 U/ml, 5 U/ml, or 50 U/ml of IL-15.

In preferred embodiments of the invention, the method of activating and expanding HPV immunogen specific T-cells comprises a step of removing the APCs that have phagocytosed a phagocytosable particle of the invention from the HPV immunogen specific T-cells. In embodiments of the invention, wherein the phagocytosable particles of the invention comprises a magnetic core, the APCs are removed from the HPV immunogen specific T-cells by using magnetic separation.

Following contact of an HPV immunogen specific T-cell with an APC that has phagocytosed a phagocytosable particle of the invention, the degree of HPV immunogen specific T-cell activation may be determined, for example by comparing the degree of HPV immunogen specific T-cell activation to a relevant reference. Determining the degree of HPV immunogen specific T-cell activation may be performed using T-cell activation assays known in the art, for example an ELISpot, FluoroSpot, intracellular staining of cytokines with flow cytometry, FASCIA, proliferation assays (e.g. thymidine incorporation, CFSE or BrdU staining), specific TCR-detection with MHC-I or II tetramers, and ELISA- or Luminex analysis of secreted cytokinesELIS potassays. The method may comprise the step of comparing the degree of HPV immunogen specific T-cell activation to a relevant reference. Suitable references include, for example, a T-cell sample that does not comprise HPV immunogen specific T-cells, or an HPV immunogen specific T-cell sample that has not been contacted with an APC that has phagocytosed a phagocytosable particle.

T-Cell Populations

T-cell populations for use in the present invention generally comprises the T-cells in an appropriate physiologically acceptable medium. Such mediums are known in the art and include, for example, aqueous sterile injectable solutions (e.g. saline, such as PBS), cell culture mediums suitable for clinical use and autologous plasma, which may also contain anti-oxidants, buffering agent (e.g. sodium phosphate, potassium phosphate, TRIS and TEA), bacteriostats, and solutes which render the T-cell population dose isotonic with the blood of the intended recipient.

The population of T-cells for use in the present invention preferably comprises CD4+ T-cells and CD8+ T-cells, for example a mixture of CD4+ T-cells and CD8+ T-cells. For example, in one embodiment, the T-cell population may comprise predominantly CD4+ T-cells. Preferably, the T-cell population comprises predominantly HPV immunogen specific T-cells, for example, HPV immunogen specific CD4+ T-cells and CD8+ T-cells.

A T-cell population for use in the present invention may further comprise an adjuvant. The term "adjuvant" as used herein is to be understood as any substance that enhances an immune response towards an antigen. Examples of adjuvants for use in the present invention include dsRNA analogues, such as polyinosinic:polycytidylic acid, Incomplete Freund's Adjuvant, cytokines (for example, interleukins), CD40, keyhole limpet hemocyanin, Toll-like receptors, CpG oligodeoxynucleotides, saponins, aluminium salts (for example aluminium hydroxyphosphate sulphate, or aluminium hydroxide, hydrated $(Al(OH)_3$, for example with 3-O-desacyl-4'-monophosphoryl lipid A (MPL) adsorbed on its surface), colloidal alum, and analogues of lipid A of lipopolysaccharide.

Treatments

The present invention provides a population of T-cells for use in the treatment or prophylaxis of HPV positive cancer in a subject. The present invention also provides methods of treating or preventing HPV positive cancer in a subject comprising the step of administering to the subject a population of T-cells of the invention. The present invention also provides a use of a population of T-cells of the invention for the manufacture of a medicament for the treatment or prevention of HPV positive cancer.

The treatments of the invention may be used to treat or prevent any form of HPV positive cancer, for example any HPV positive solid cancer, metastatic solid cancer or hematologic malignancy. The treatments of the invention are especially effective in the treatment of HPV positive cervical, vaginal, vulval, penile, anal, mouth, throat and head and neck cancers. The current invention is particularly effective for the treatment of penile cancers.

The treatments of the invention also find use in the treatment of patients having a refractory and/or relapsed HPV positive cancer. For example, the population of T-cells of the invention finds use in the treatment or prophylaxis of refractory and/or relapsed HPV positive cancers in patients that have previously been treated with a currently available treatment, such as single or repeat treatment cycles of a chemotherapeutic agent.

The treatments of the invention also find use in the treatment of subjects that have previously received a prophylactic HPV vaccine, for example a dose of a HPV vaccine such as Gardasil®, Gardasil 9° or Cervarix®. For example, the method of treatment can comprise a first step of injecting a subject with a HPV vaccine, followed by administering a dose of a population of HPV specific T-cells. The subject may also receive one or more further doses of HPV specific T-cells as required and described herein. The one or more doses of HPV specific T-cells can be administered to a subject immediately after a dose of HPV vaccine has been administered or one or more doses of HPV specific T-cells can be administered days, weeks, months or years after a dose of a HPV vaccine has been administered.

It is expected that the HPV specific T-cells of the invention will be effective in treating HPV positive cancers in subjects that have previously received a dose of a HPV vaccine that was ineffective at preventing the development of a HPV positive cancer in the subject. For example, the HPV cancer may have been ineffective at inducing immunity against a HPV immunogen in the subject, or the HPV vaccine may have induced immunity against a HPV immunogen from one strain of HPV, but the HPV positive cancer in the subject is caused by a different HPV strain. The present invention allows for the ex vivo expansion of T-cells that are specific to HPV immunogens that are known or suspected of being associated with a HPV positive cancer in a subject. The versatility of the method, phagocytosable particles and kits of the present invention enable the tailoring of the treatment to target the HPV positive cancer in the subject.

The treatments of the invention also find use in the treatment of subjects that are known or suspected of lacking immunity to the strain of HPV known or suspected of being associated with the cancer in the subject. The treatments of the invention also find use in subjects that are known or suspected of having reduced immunity against HPV or have an ineffective or compromised immune system. For the treatment of such subject, the method of the invention can comprise the ex vivo expansion of HPV specific T-cells that have been obtained from a compatible donor. In addition, or alternatively, the method can comprise obtaining T cells from the subject and expanding the HPV specific T-cells to a level that can be used a treat the HPV positive cancer in the subject.

Whilst a population of T-cells of the present invention may be use as the sole active ingredient for the treatment or prophylaxis of HPV positive cancer in a subject or in methods of treating or preventing HPV positive cancer in a subject comprising the step of administering to the subject a population of T-cells of the invention, it is also possible for a population of T-cells to be used in combination with one or more further therapeutic agents and/or in combination with radiation therapy.

Thus, the invention also provides a population of T-cells according to the invention together with a further therapeutic agent, for simultaneous, sequential or separate administration. The invention also provides a population of T-cells according to the invention together with a further therapeutic agent, for simultaneous, sequential or separate administration for use in the treatment or prophylaxis of HPV positive cancer in a subject, or for use in methods of treating or preventing HPV positive cancer in a subject comprising the step of administering to the subject a population of T-cells of the invention and the further therapeutic agent.

The further therapeutic agent may a therapeutic agent for use in the treatment or prophylaxis treatment or prophylaxis of HPV positive cancer. The further therapeutic agent may a therapeutic agent for use in the treatment or prophylaxis of cervical, vaginal, vulval, penile, anal, mouth, throat or head and neck cancers.

For example, the further therapeutic agent may be an immune checkpoint inhibitor, a chemotherapeutic agent or a phagocytosable particle comprising a core and a HPV immunogen of the present invention.

Examples of chemotherapeutic agent include alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, antimetabolites, erlotinib, vemurafenib, crizotinib, sorafenib, ibrutinib, enzalutamide, folic acid analogues, purine analogs, androgens, anti-adrenals, folic acid replenisher such as folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid 2-ethylhydrazide, procarbazine, PSK® polysaccharide complex (JHS Natural Products, Eugene, OR), razoxane, rhizoxin, sizofiran, spirogermanium, tenuazonic acid, triaziquone; 2,2',2"-trichlorotriethylamine, trichothecenes (especially T-2 toxin, verracurin A, roridin A and anguidine), urethan, vindesine, dacarbazine, mannomustine, mitobronitol, mitolactol, pipobroman, gacytosine, arabinoside ("Ara-C"), cyclophosphamide, thiotepa, taxoids, chloranbucil, gemcitabine, 6-thioguanine, mercaptopurine, methotrexate, platinum analogs, vinblastine, platinum, etoposide (VP-16), ifosfamide, mitoxantrone, vincristine, vinorelbine, novantrone, teniposide, edatrexate, daunomycin, aminopterin, xeloda, ibandronate, irinotecan (Camptosar, CPT-11), topoisomerase inhibitor RFS 2000, difluorometlhylornithine, retinoids, capecitabine, combretastatin, leucovorin, oxaliplatin, inhibitors of PKC-alpha, Raf, H-Ras, EGFR and VEGF-A that reduce cell proliferation, and pharmaceutically acceptable salts, acids or derivatives thereof, and combinations thereof.

Examples of immune checkpoint inhibitors include an agent or antibody that inhibits one or more of CTLA4, PD-1, PD-L1, LAG-3, B7-H3, B7-H4, TIM3, VISTA and KIR. In one preferred embodiment, the further therapeutic agent is an immune checkpoint inhibitors, and in particular an immune checkpoint inhibitors that is an agent or antibody that inhibits one or more of CTLA4, PD-1, PD-L1, LAG-3, B7-H3, B7-H4, TIM3, VISTA and KIR. For example, the checkpoint inhibitor is an agent or antibody that inhibits CTLA-4, PD-1 or PD-L1. Examples of PD-1 inhibitors include cemiplimab, nivolumab and pembrolizumab. Examples of PD-L1 inhibitors include atezolizumab, avelumab and durvalumab. An example of a CTLA-4 inhibitor is ipilimumab.

Dosing and Dosage Regimens

A therapeutic dose of the population of T-cells expanded using the method of the present invention is a dose sufficient to treat or prevent cancer in a subject. For example, the therapeutic dose is sufficient to reduce the size of a HPV positive cancer and/or reduce the proliferation of HPV positive cancer cells in the subject. The population of T-cells may be administered to the subject intravenously, intraarterially, intrathecally or intraperitoneally. The precise dosage of a population of T-cells will vary with the characteristics of the T-cell population, for example, the number of T-cells, number of CD4+ T-cells, the number of CD8+ T-cells, and the number of HPV specific T-cells in the T-cell population expanded using the method of the present invention. Further factors, include for example, the dosing schedule, the age, size, sex and condition of the subject (typically mammal or human), the nature and severity of the condition, and other relevant medical and physical factors. Thus, a precise therapeutically effective amount can be readily determined by the clinician. An appropriate amount can be determined by routine experimentation from animal models and human clinical studies. For humans, an effective dose will be known or otherwise able to be determined by one of ordinary skill in the art.

In certain preferred embodiments, a subject is administered a therapeutic dose of HPV specific T-cells and is then administered at least one further (or "subsequent") therapeutic dose of HPV specific T-cells of the invention, or an injectable composition comprising a therapeutic dose of HPV specific T-cells of the invention. Further (or "subsequent") therapeutic doses of HPV specific T-cells may be administered daily, every second or third day, weekly, every second, third or fourth week, monthly, every second, third or fourth month, every 6 months, or every year. The number and frequency of further therapeutic dose(s) of HPV specific T-cells of the invention will depend on the subject, and the form and severity of the cancer to be treated.

In certain embodiments, a subject is administered a therapeutic dose of HPV specific T-cells and is then administered at least one further (or "subsequent") therapeutic dose of HPV specific T-cells of the invention, or an injectable composition comprising a therapeutic dose of HPV specific T-cells of the invention. Further (or "subsequent") therapeutic doses of phagocytosable particles may be administered daily, every second or third day, weekly, every second, third or fourth week, monthly, every second, third or fourth month, every 6 months, or every year. The number and frequency of further therapeutic dose(s) of HPV specific T-cells of the invention will depend on the subject, and the form and severity of the cancer to be treated. In one embodiment, the use of HPV specific T-cells for the treatment or prophylaxis of HPV positive cancer comprises administering one or more subsequent therapeutic doses of HPV specific T-cells to the subject, wherein the subject is one whom has previously been administered a therapeutic dose of HPV specific T-cells, or an injectable composition comprising a therapeutic dose of HPV specific T-cells of the invention. Each of the one or more subsequent therapeutic doses are a dose sufficient to reduce the size of a HPV positive cancer or reduce proliferation of a HPV positive cancer in a subject.

In another embodiment, the use of HPV specific T-cells for the treatment or prophylaxis of HPV positive cancer comprises administering one or more subsequent therapeutic doses of HPV specific T-cells to the subject, wherein the subject is one whom has previously been administered a therapeutic dose of HPV specific T-cells, or an injectable composition comprising a therapeutic dose of phagocytosable particles of the invention. Each of the one or more subsequent therapeutic doses are a dose sufficient to reduce the size of a HPV positive cancer or reduce proliferation of a HPV positive cancer in a subject.

In embodiments of the invention comprising administering one or more subsequent therapeutic doses of HPV specific T-cells to the subject, preferably 2, 3, 4, 5, 6, 7, 8, 9, 10 or n subsequent therapeutic doses of the HPV specific T-cells wherein "n" is any number of doses greater than 10 doses (for example 11, 12, 13, 14, 15, 16, 17, 18, 19, 20, 21, 22, 23, 24, 25, 26, 27, 28, 29 or 30 doses). Preferably, the number and frequency of subsequent therapeutic doses administered to the subject is sufficient to treat or prevent cancer in the subject.

In embodiments of the invention comprising administering one or more subsequent therapeutic doses of HPV specific T-cells to the subject, preferably, the one or more subsequent therapeutic doses are administered to the subject at intervals of days, weeks or months. For example, one or more subsequent therapeutic doses are administered to the subject every day, every second day, every third day, every fourth day, every fifth day or every sixth day. Alternatively, or additionally, one or more subsequent therapeutic doses are administered to the subject, for example, once every week, once every two weeks, once every three weeks or once every four weeks. Alternatively, or additionally, one or more subsequent therapeutic doses are administered to the subject, for example, once every month, once every two months, once every three months or once every 6$^{th}$ month. Alternatively, or additionally, one or more subsequent therapeutic doses are administered to the subject, for example, once every year.

In one embodiment of the invention, the one or more subsequent therapeutic doses are administered to the subject once every year, two times every year or three times every year. For example, the one or more subsequent therapeutic doses may be administered to the subject once every year, two times every year or three times every year for a period of 1 to 10 years, 10 to 20 years, 20 to 30 years, 30 to 40 years or 50 to 60 years.

It is expected that by administering one or more subsequent therapeutic doses to a subject over a long period of time (i.e. over one or more years), it is possible to boost the number of HPV specific memory T-cells that are present in the subject. It is expected that by boosting the number of HPV immunogen specific memory T cells in a subject maintains the HPV immunogen specific immunological memory in the subject, such that a HPV positive cancer is prevented from growing or returning.

In certain embodiments of the invention, a booster dose is administered to a subject whose cancer has been successfully treated (with one or more therapeutic doses as described herein) to prevent the HPV positive cancer returning.

A booster dose of HPV specific T-cells may independently have any of the properties and/or characteristics of a therapeutic dose of HPV specific T-cells as described herein.

In one embodiment of the invention, one or more booster doses are administered to the subject, for example, once every week, once every two weeks, once every three weeks or once every four weeks. Alternatively, or additionally, one or more booster doses are administered to the subject, for example, once every month, once every two months, once every three months or once every 6$^{th}$ month. Alternatively, or additionally, one or more booster doses are administered to the subject, for example, once every year.

In another embodiment of the invention, the one or more booster doses are administered to the subject once every year, two times every year or three times every year. For example, the one or more booster doses may be administered to the subject once every year, two times every year or three times every year for a period of 1 to 10 years, 10 to 20 years, 20 to 30 years, 30 to 40 years or 50 to 60 years.

It is expected that boosting the number of HPV immunogen specific memory T cells in a subject by administering one or more booster doses maintains the HPV immunogen specific immunological memory in the subject, such that the cancer is prevented from growing or returning.

Further aspects of the invention are defined in the following numbered clauses:

§ 1. A method for the expansion of HPV immunogen specific T-cells, comprising the steps of:
 i. providing a human papillomavirus (HPV) immunogen or a phagocytosable particle comprising a core and a HPV immunogen tightly associated to the core; wherein the HPV immunogen has an amino acid sequence that corresponds to the amino acid sequence of a HPV protein, or has an amino acid sequence that corresponds to an amino acid sequence of a part of a HPV protein;
 ii. providing APCs
 iii. contacting the HPV immunogen or the phagocytosable particle comprising a core and a HPV immunogen with the APCs from step ii in vitro, and under conditions allowing phagocytosis of the HPV immunogen by the APCs;
 iv. providing T-cells that have been harvested from the subject;
 v. contacting the T-cells with the APCs from step iii) in vitro, and under conditions allowing specific activation of HPV immunogen specific T-cells.

§ 2. A method as described in § 1 in which the T-cells have been harvested from a tumour draining lymph node in the subject.

§ 3. A method as described in § 1 or § 2 in which the HPV immunogen includes one or more HPV proteins necessary for viral replication (e.g. E1 to E7) and HPV coat proteins (e.g. L1 and L2).

§ 4. A method as described in § 3 in which the HPV immunogen includes one or more of HPV coat protein L1 derived from any one of HPV types 6, 11, 16, 18, 31, 33, 45, 52 and 58.

§ 5. A method as described in § 4 in which the HPV immunogenic construct comprises HPV immunogens contained in a commercially available HPV vaccine (for example Gardasil®, Gardasil 9® or Cervarix®).

§ 6. An expanded population of T-cells obtained by a method as claimed in any one of § 1 to § 5.

§ 7. A population of T-cells as described in § 6 for use in the treatment of an HPV-mediated cancer.

§ 8. A population of T-cells for use a described in § 7 wherein the HPV-mediated cancer is selected from cervical, vaginal, vulval, penile, anal, mouth, throat and head and neck cancers, for example penile cancer.

§ 9. A phagocytosable particle comprising a core and a HPV immunogen tightly associated to the core; wherein the HPV immunogen has an amino acid sequence that corresponds to the amino acid sequence of a HPV protein, or has an amino acid sequence that corresponds to an amino acid sequence of a part of a HPV protein.

The invention is further described by the following examples, which are not intended to limit the scope of the invention.

EXAMPLES

Example 1: General Protocol for Coupling HPV Immunogens or Model Peptides/Proteins to Magnetic Cores Coupling of HPV immunogenic constructs or model peptides/proteins to a core: Dynabeads® MyOne™ Carboxylic Acid (ThermoFischer Scientific) were used (1 µm diameter spheres) as the core. Dynabeads® MyOne™ Carboxylic Acid particles are paramagnetic polystyrene particles comprising iron oxide and functionalised on the surface of the particle with free carboxylic acid groups. The coupling procedure may be carried out according to the manufacturer's protocol (Two-Step procedure using NHS (N-Hydroxysuccinimide) and EDC (ethyl carbodiimide)):

Step 1): The polystyrene particles are washed twice with MES-Buffer (25 mM MES (2-(N-morpholino)ethanesulfonic acid), pH 6). The carboxylic acid groups are then activated by adding 50 mg/ml NHS (N-Hydroxysuccinimide) and 50 mg/ml EDC (N-(3-Dimethylaminopropyl)-N'-ethylcarbodiimide) in MES-buffer to the polystyrene particles and incubated for 30 min at room temperature (RT). The polystyrene particles are collected with a magnet and the supernatant removed. The polystyrene particles are then washed twice with MES-buffer.

Step 2): The HPV immunogenic construct or model peptide/protein sample is diluted in MES-buffer to a concentration of 1 mg/ml, total 100 μg and added to the polystyrene particles and incubated for 1 h in room temperature. The polystyrene particles are collected with a magnet and the supernatant was removed and saved for peptide-concentration measurement. The non-reacted activated carboxylic acid groups are quenched with 50 mM Tris pH 7.4 for 15 min. The polystyrene particles are then washed with PBS pH 7.4 and then stored in −80° C.

A BCA (bicinchoninic acid) protein assay kit (Pierce BCA Protein Assay Kit, ThermoFisher Scientific) is used according to the manufacturer's protocol, to measure the amount of peptidic material coupled to the polystyrene particles and to measure the peptidic material concentration of the HPV immunogenic construct or model peptides/protein in a sample before coupling as well as the peptidic material concentration of the supernatant after coupling.

Example 2: Washes

Phagocytosable particles comprising a core (Dynabeads®) and a model protein (Ovalbumin or Cytomegalovirus protein pp65) attached to the core were prepared according to the protocol described in Example 1. After coupling the phagocytosable particles were washed with one of 3 different wash-buffers: 2M NaOH pH 14.3, 8 M Urea or 6 M Guanidine (Guanidine-HCl), all in sterile water at RT, or they were incubated in PBS at 95° C. The polystyrene particles were suspended in the buffer and shaken for 4 min, collected with a magnet and the supernatant removed. This was repeated 3 times. The heat treated polystyrene particles were put in PBS pH 7.4 and put in a heating block at 95° C. for 5 minutes, then collected with a magnet and the supernatant removed. This was repeated 3 times. The particles were then washed 3 times with sterile PBS to remove any remaining wash-buffer.

Four different washing conditions were tested: (a) High pH (2M NaOH pH 14.3), (b) Heat (95° C.) and sterilising/denaturing agents ((c) 8M Urea and (d) 6M guanidine hydrochloride). In every case, the model proteins associated with the polystyrene particles remained associated with the polystyrene particles.

Example 3a: Identification of Suitable Particle Size for Phagocytosable Particles Using Ovalbumin as Model Antigen A cell proliferation assay measuring Thymidine incorporation was used to test the effect of phagocytosable particle size on antigen-specific T-cell activation. Splenocytes from ovalbumin (OVA) immunized mice were stimulated with OVA coupled polystyrene particles of different sizes to measure antigen specific proliferation.

Dynabeads® MyOne™ Carboxylic Acid particles with a diameter of 5.6 μm, 1 μm and 0.2 μm were coupled with OVA (OVA-particles) or bovine serum albumin (BSA-particles) according to the protocol in Example 1.

To test the effectiveness of the OVA-particles to stimulate antigen specific T-cell activation a proliferation assay (with $^3$H thymidine incorporation) was used. Particle concentration in relation to cell concentration was 1:1 for the 5.6 μm particles, 10:1 for the 1 μm particles and 500:1 for the 0.2 μm particles. Total protein concentration during the incubation with the cells was calculated to 125 ng/ml, 160 ng/ml and 160 ng/ml for the 5.6 μm, 1 μm and 0.2 μm respectively. The proliferation assay was run as follows:

Proliferation assay with thymidine incorporation with splenocytes from ovalbumin sensitized mice. As stimuli, ovalbumin (SigmaAldrich) and BSA (SigmaAldrich) coupled to Dynabeads® MyOne™ Carboxylic Acid particles were used. Mice were immunized to ovalbumin via monthly injections of 100 μg ovalbumin (Sigma) adsorbed to aluminium hydroxide. Three months after the first injection the mice were killed and spleens harvested. Splenocytes were prepared by standard procedures, as described in Thunberg et al. 2009, Allergy 64:919.

The cells were incubated in cRPMI either with ovalbumin coupled beads or BSA coupled beads (10 beads per cell) for 5 days. All cells were incubated for 6 days in a humidified atmosphere with 6% $CO_2$ at 37° C. One μCu/well [$^3$H] thymidine was added to cell cultures for the final 18 h of incubation. Mean counts per minute (cpm) obtained from stimulated triplicates were divided by mean cpm values from un-stimulated cells and expressed as stimulation indices (SI). SI-values 2.0 are generally considered positive.

As seen in FIG. 1, cells incubated with OVA-particles with a diameter of 0.2 μm showed increase in proliferation with a mean SI of 4.1 (95% CI 2.4-5.8, P=0.007). The cells incubated with OVA-particles with a diameter of 1 μm showed increase in proliferation with a mean SI of 8.4 (95% CI 6.1-10.6, P<0.005). The cells incubated with OVA-particles with a diameter of 5.6 μm failed to stimulate proliferation, mean SI 1.1 (95% CI 0.4-2.7, P=0.876).

These results show that antigen coupled to particles of different sizes can stimulate cell proliferation. The particles with a diameter of about 1 μm appear to be most efficient at stimulating cells, but particles with a size of 0.2 μm still work. The inventors predict that particles of sizes larger than 1 μm also work, although as the diameter comes close to 5.6 μm the particles completely fail to stimulate the cells. It is reasonable to assume that 1 μm is an optimal size, since it is similar to the size of bacteria. Our immune system has evolved to phagocytose and react to microorganisms/particles of this size. A normal antigen presenting cell has a size in the range 10-15 μm.

Example 3b: Comparison of Antigen Coupled Particles of Different Particle Sizes and their Effectiveness in Activating and Expanding T-Cells (i) Preparation of Antigen Coupled Phagocytosable Particles:

Three kinds of paramagnetic polystyrene phagocytosable particles of different sizes were used:
diameter of 1 μm (Dynabeads MyOne Carboxylic Acid, ThermoFisher),
diameter of 2.8 μm (Dynabeads M-270 Carboxylic acid, ThermoFisher) and
diameter of 4.5 μm (Dynabeads M-450 Epoxy, ThermoFisher).

The phagocytosable particles were coupled with the model virus antigen Cytomegalovirus (CMV) protein pp65 construct according to the manufacturer's instruction. The pp65 construct has as amino acid sequence according to SEQ ID NO. 15. The CMV pp65 construct contains five linked 22 to 23-amino acid pp65 peptides, an N-terminal histidine-tag, and N-terminal albumin-binding domain (ABD)-tag. The construct was recombinantly expressed using *E. coli* and purified using column chromatography. To remove endotoxin, the phagocytosable particles were washed five times with a 0.75M sodium hydroxide buffer and subsequently resuspended in sterile PBS.

SEQ ID NO. 15:
MGSSHHHHHHSSGSLAEAKVLANRELDKYGVSDYHKNLINNAKTVEGVK

DLQAQVVESAKKARISEATDGLSDFLKSQTPAEDTVKSIELAEAKVLAN

RELDKYGVSDYYKNLINNAKTVEGVKALIDEILAALPGGSAETRLLQTG

IHVRVSQPSLILVGGSIIKPGKISHIMLDVAFTSHEHFGGSWPPWQAGI

LARNLVPMVATVQGGSRGPQYSEHPTFTSQYRIQGKLGGSQNLKYQEFF

WDANDIYRIFAE (ii) Incubation of Antigen Coupled Phagocytosable Particles:

Peripheral blood mononuclear cells (PBMCs) from a CMV-sensitive healthy donor, isolated via standard ficoll-based density gradient centrifugation were cultured together with the phagocytosable particles coupled with the CMV construct (hereinafter referred to as "CMV-particles") in a 48-well plate for 18 h at 37° C., 5% $CO_2$, 500,000 cells/well at a concentration of 1,000,000 cells/ml. The concentration of CMV-particles were equalized based on total surface area (a surrogate marker for CMV amount as it is bound to the surface of the CMV-particles). This equalled to 10 CMV-particles/PBMC for the 1 μm sized particles, 1.4 CMV-particle/PBMC for the 2.8 μm sized particles and 0.5 CMV-particles/PBMC for the 4.5 μm sized particles, based on the number of total PMBCs in the sample. The results for each particle sized is shown below in Table 1.

cell vs estimated 2.4 CMV-particles/cell) and can as such be assumed to accurately estimate the amount of 1 μm CMV-particles as well.

Figure 2:
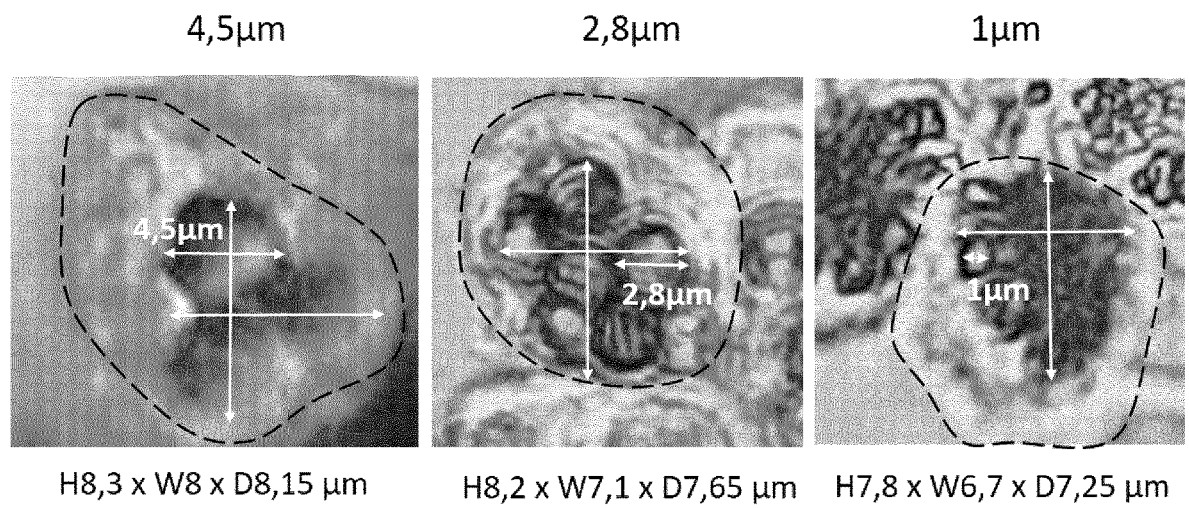
FIG. 2A shows the confocal microscope images of PBMCs with intracellular, phagocytosed particles. Three sizes of phagocytosable particle are shown (4.5 µm, 2.8 µm or 1 µm) following incubation for 18 h at 37° C. of PBMCs with the phagocytosed particles.
FIG. 2B shows the cellular uptake of phagocytosable particles of two sizes (4.5 µm or 2.8 µm) after incubation with PBMCs for 18 h at 37° C., as assessed by manual counting.
FIG. 2C shows the cellular uptake of phagocytosable particles of three sizes (4.5 µm, 2.8 µm or 1 µm) after incubation in PBMCs for 18 h at 37° C., as assessed by volume calculation (*$p<0.05$ $p<0.01$ *$p<0.001$, calculated using Student's T-test).
Figure 2:
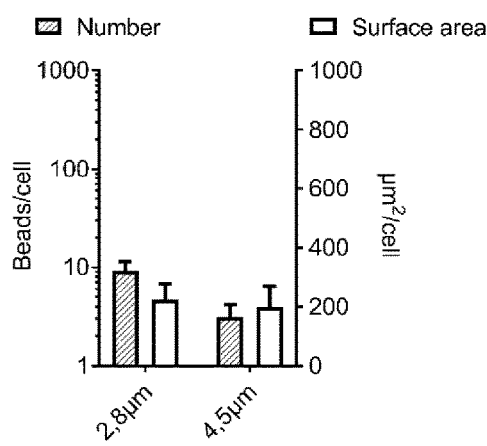
Figure 2:
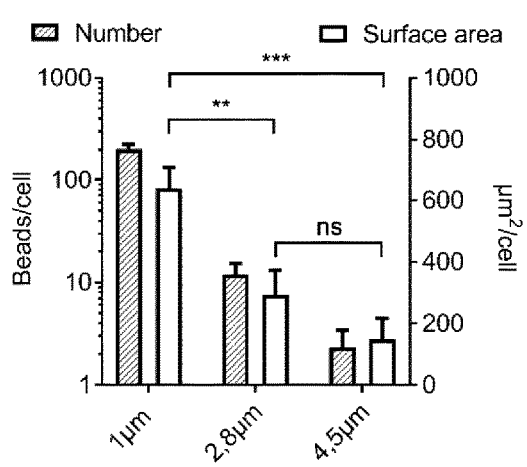

The uptake of CMV-particles in shown in FIGS. 2B and 2C. FIG. 2B shows the number of CMV-particles taken up by each cell as assessed by manual counting (8 cells counted per bead-type). Using the manual counting method, it was found that the number of phagocytosed particles per cell for the 4.5 μm CMV-particles was of 3.1 (±1.1). For the 2.8 μm CMV-particles it was 9.1 (±2.2). It was not possible to count the number of 1 μm CMV-particles using this method.

FIG. 2C shows the number of CMV-particles taken up by each cell as assessed by the volume calculation (3 cells measured per bead-type) (*$p<0.05$ $p<0.01$ *$p<0.001$, calculated using Students T-test). Using the volume calculation method, it was found that the number of phagocytosed particles per cell for the 4.5 μm CMV-particles was of 2.4 (±1.1). For the 2.8 μm CMV-particles it was 11.9 (±3.2). For the 1 μm CMV-particles it was 203.7 (±21.9).

Based on the number of CMV-particles taken up by each cell as assessed by the volume calculation method, the total phagocytized surface area, and by extension the total amount of CMV, was calculated. The surface area that was taken up was calculated as 639.6 (±68.9) μm² for the 1 μm CMV-particles, 293.1 (±79.3) μm² for the 2.8 μm CMV-particles and 150.7 (±67.0) μm² for the 4.5 μm CMV-particles. These data are shown in Table 2 below.

TABLE 2

| Particle size | CMV-particles uptake per cell (counted) | CMV-particles uptake per cell (calculated from volume) | Surface area taken up per cell |
|---|---|---|---|
| 1 μm | — | 203.7 (±21.9) | 639.6 (±68.9) μm² |
| 2.8 μm | 9.1 (±2.2) | 11.9 (±3.2) | 293.1 (±79.3) μm² |
| 4.5 μm | 3.1 (±1.1) | 2.4 (±1.1) | 150.7 (±67.0) μm² |

TABLE 1

| Particle size | Number of PBMCs in sample | Ratio of CMV-particles to PBMCs | Number of CMV-particles in sample |
|---|---|---|---|
| 1 μm | 500,000 | 10:1 | 5,000,000 |
| 2.8 μm | 500 000 | 1.4:1 | 700 000 |
| 4.5 μm | 500 000 | 0.5:1 | 250 000 |

(iii) Assessment of Uptake:

After incubation, the number of phagocytosed CMV-particles were manually counted using a confocal microscope. Eight cells were counted to obtain mean and standard deviation values. In FIG. 2A, there are shown images from the confocal microscope of representative cells with intracellular phagocytosed CMV-particles. Black dashed line indicates the outline of the cell. The white line shows the dimensions of the total intracellular CMV-particles.

This method was not applicable for the 1 μm CMV-particles as they were too small to accurately count. In order to assess the amount of 1 μm CMV-particles, the total volume of all phagocytosed CMV-particles were measured and the amount of individual CMV-particles were back-calculated based on the total volume, assuming a packing density of 60%. This method proved reasonably accurate for the 2.8 μm CMV-particles (manually counted 9.1 CMV-particles/cell vs estimated 11.9 CMV-particles/cell) and 4.5 μm CMV-particles (manually counted 3.1 CMV-particles/

(iv) Assessment of T-Cell Stimulation

The ability of the antigen coupled particles to stimulate T-cells and hence promote their expansion was assessed by measuring the release of IFNγ, IL-22 and IL-17A from PBMCs using a FluoroSpot assay (Mabtech, Sweden). PBMCs (250,000/well) from CMV-sensitive healthy donors (n=2) were stimulated with the CMV-particles in triplicates. The concentration of antigen coupled particles were as previously described equalized based on total surface area: 10×1 μm CMV-particles/cell, 1.4×2.8 μm CMV-particles/PBMC and 0.5×4.5 μm CMV-particles/cell. The number of PBMCs per well of the FluoroSpot assay is shown below (Table 3) for each particle size, together with the estimated number of monocytes per well (based on an estimated 20% monocyte content of a PBMC sample).

TABLE 3

| particle size | Number of PBMCs per well | Number of monocytes per well |
|---|---|---|
| 1 μm | 250,000 | 50,000 |
| 2.8 μm | 250,000 | 50,000 |
| 4.5 μm | 250,000 | 50,000 |

The PBMCs were incubated for 44 h at 37° C., 5% $CO_2$. The plates were developed according to the manufacturer's instructions and read in an automated FluoroSpot reader. The data reported for the FluoroSpot is spot-numbers when the cells are stimulated with CMV-particles above the spot-numbers when not stimulated with CMV-particles.

Figure 3:
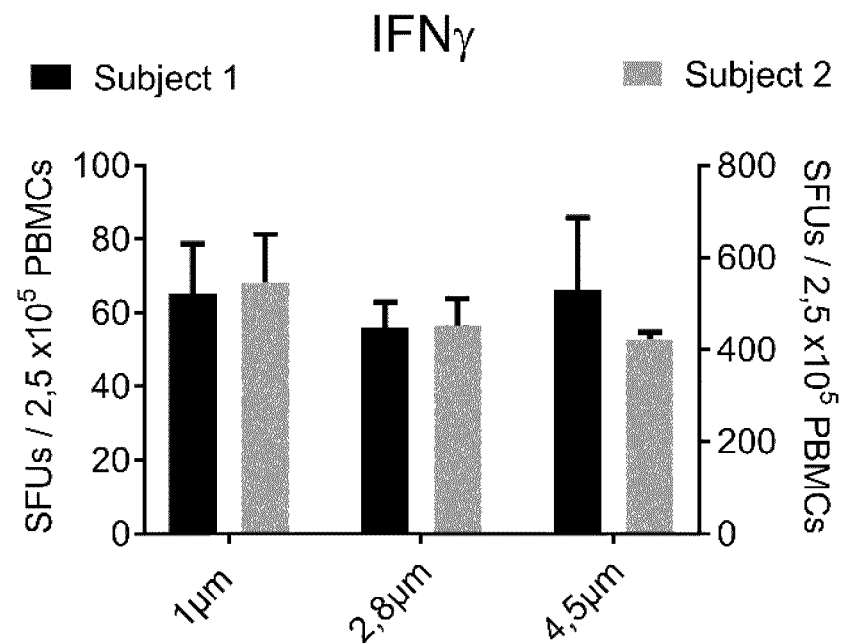
FIG. 3A shows the relative increase in the level of IFNγ-production in PBMCs from cytomegalovirus (CMV) sensitive healthy donors (also referred to herein as CMV positive donors), (n=2) stimulated with phagocytosable particles of three sizes (4.5 µm, 2.8 µm or 1 µm) compared to non-stimulated cells, as assessed in the FluoroSpot assay of Example 3a(iv).
FIG. 3B shows the relative increase in the level of IL-22-production in PBMCs from a CMV-sensitive healthy donor (n=1) stimulated with phagocytosable particles of three sizes (4.5 µm, 2.8 µm or 1 µm) compared to non-stimulated cells, as assessed in the FluoroSpot assay of Example 3a(iv).
FIG. 3C shows the relative increase in the level of IL-17-production in PBMCs from CMV-sensitive healthy donor (n=1) stimulated with phagocytosable particles of three sizes (4.5 µm, 2.8 µm or 1 µm) compared to non-stimulated cells, as assessed in the FluoroSpot assay of Example 3a(iv).
FIG. 3D shows the relative increase in the dual-cytokine production of IFNγ and IL-17 in PBMCs from a CMV-sensitive healthy donor (n=1) stimulated with phagocytosable particles of three sizes (4.5 µm, 2.8 µm or 1 µm) compared to non-stimulated cells, as assessed in the FluoroSpot assay of Example 3a(iv).
FIG. 3E shows the relative increase in the dual-cytokine production of IL-22 and IL-17 in PBMCs from a CMV-sensitive healthy donor (n=1) stimulated with phagocytosable particles of three sizes (4.5 µm, 2.8 µm or 1 µm) compared to non-stimulated cells, as assessed in the FluoroSpot assay of Example 3a(iv).
Figure 3:
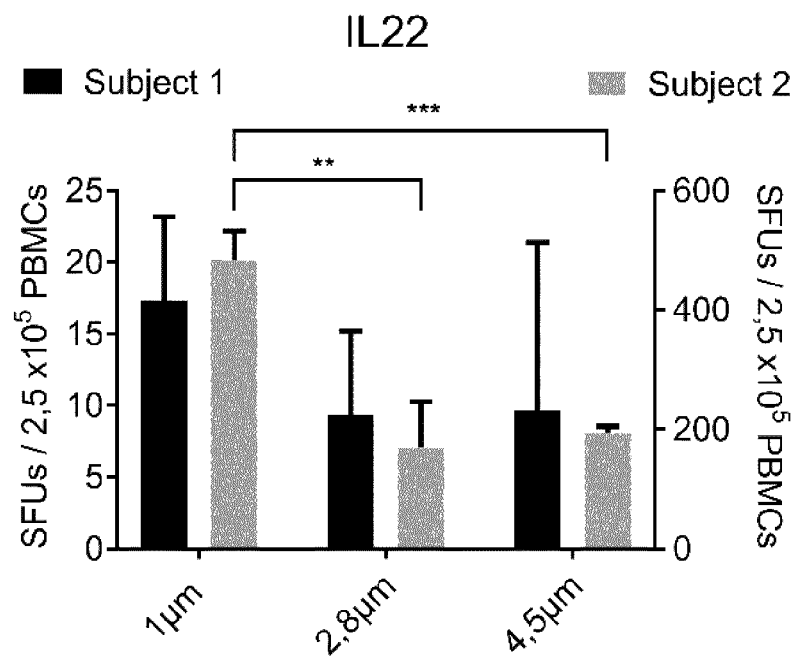
Figure 3:
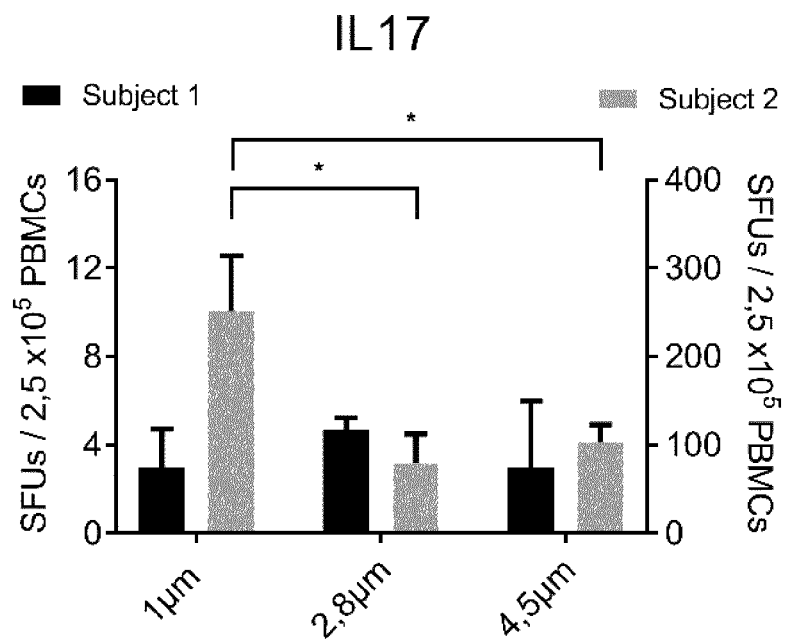
Figure 3:
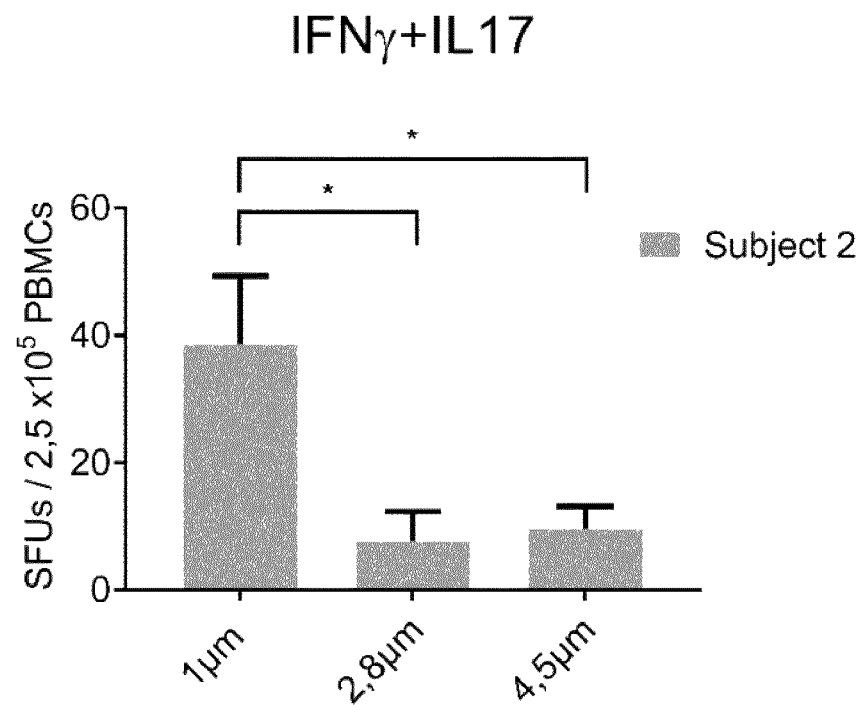
Figure 3:
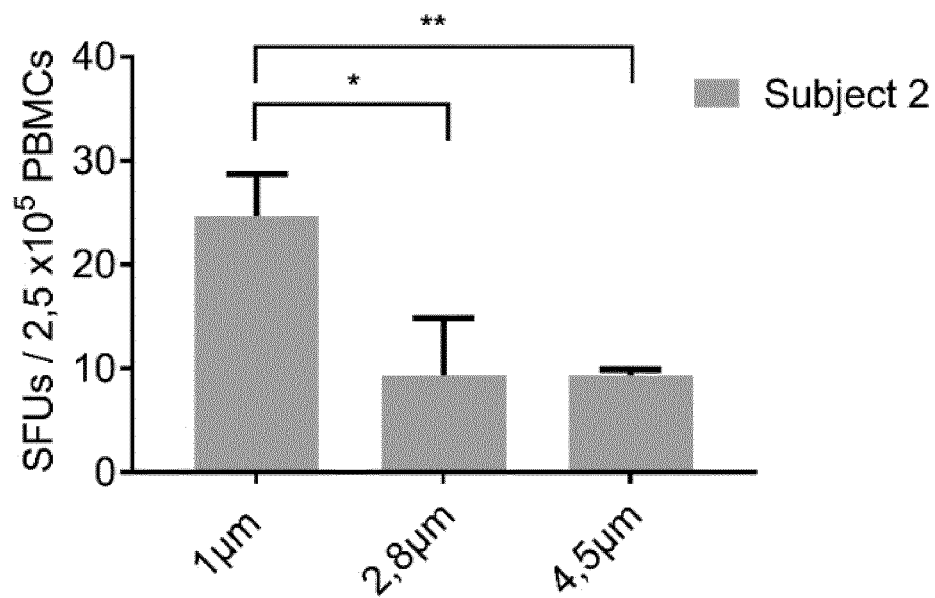

The level of IFNγ-production, as assessed in the FluoroSpot assay, is shown in FIG. 3A. It is seen that there is little difference between the CMV-particles.

The level of IL-22 and IL-17 production, as assessed in the FluoroSpot assay, is shown in FIGS. 3B and 3C. It is seen that the 1 µm CMV-particles caused a significantly higher IL-22 and IL-17 production in one individual than the larger CMV-particles, with a similar trend seen for the other individual in regards to IL-22.

The level of dual-cytokine production, as assessed in the FluoroSpot assay, is shown in FIGS. 3D and 3E. It is seen that the 1 µm CMV-particles caused a significantly higher dual-cytokine release (IFNγ+IL-17 and IL-22γ+IL-17) for one healthy donor when stimulated with the 1 µm CMV-particles than with the larger CMV-particles.

The cytokine release in these experiments serves as a proxy for T-cell expansion. In general, IFNγ is produced by CD4+ T-cells (Th1 subclass) and CD8+ T-cells. IL-17 and IL-22 are mainly produced by pro-inflammatory Th17 CD4+ T-cells. Such cells are pro-inflammatory have been shown to assist in tumour eradication. The data suggest that the 1 µm phagocytosable particles activate and cause expansion of Th1 CD4+ T-cells and CD8+ T-cells to the same degree as the other beads, with the added benefit of also activating and causing expansion of additional pro-inflammatory Th17 CD4+ T-cells and the less distinct but still pro-inflammatory double cytokine producing T-cells.

Example 4: Study of HPV in a Cohort of Penile Cancer Patients

Patients 11 patients with invasive penile cancer, 50-84 years old, from Sodersjukhuset, Stockholm and Norrlands Universitetssjukhus, Umea, Sweden, (2013-2015) undergoing radical surgery and regional lymph node dissection, were included (Table 4). Preoperative staging; cT1-2N0-1M0. The study was approved by the regional ethical committee and informed consent was obtained from all participants (EPN-$^{2013}$/$_{835}$-32).

TABLE 4

| Patient No | Age | Clinical Tumour staging | No of excised lymph nodes | No of metastatic lymph nodes |
|---|---|---|---|---|
| 1 | 84 | T2N0M0 | 4 | 0 |
| 2 | 72 | T1N0M0 | 3 | 0 |
| 3 | 72 | T2N0M0 | 4 | 0 |
| 4 | 78 | T1N0M0 | 2 | 0 |
| 5 | 66 | T1N0M0 | 5 | 0 |
| 6 | 50 | T2N0M0 | 4 | 0 |
| 7 | 80 | T2N0M0 | 7 | 0 |
| 8 | 77 | T1N0M0 | 4 | 0 |
| 9 | 78 | T2N1M0 | 8 | 1 |
| 10 | 78 | T1N0M0 | 4 | 2 |
| 11 | 70 | T2N0M0 | 4 | 0 |

Preparation of Specimens

One piece of primary tumour was dissected at surgery, and further used for PCR analyses and antigen source preparation. Lymph nodes (LNs) were identified and removed, and one half of LNs respectively underwent routine histopathology and immunological evaluation.

Preparation of Single Cells

Venous blood, LNs, and tumour specimens were immediately harvested. Peripheral blood mononuclear cells (PBMC) were purified by ficoll-hypaque (Pharmacia, Amersham). Single cell suspensions from tissue specimens were obtained by gentle pressure using a loose-fit glass-homogenizer. Cells were washed twice and resuspended in AIM V® (Life technologies).

Flow Cytometry (FACS)

PBMC, LNs and tumour cell suspensions at 0.5×10$^6$ cells/sample were washed in PBS containing 2% FCS and 0.05% NaN$_3$ (FACS-buffer). For investigating subtypes of lymphocytes and their functions, staining was performed with fluorophore conjugated antibodies: Blue Live/Dead stain, anti-CD4 Pacific-Blue, anti-CD8 APC, anti-CD19 APC-Cy7 and anti-CD56 PE (Becton Dickinson). Cells were investigated with LSRFORTESSA (Becton Dickinson) and analysed using the FACS DIVA software (Becton Dickinson).

Activation of T Cells

Tumour samples were homogenized using an Ultra-Turrax homogenizer in 5 volumes (w/v) of RPMI, followed by 5 minutes denaturation at 98° C. Activation of single cell suspensions of PBMC, lymph node cells and T-cells were tested at 0.5 million cells/tube using tumour homogenate, Gardasil® (0.1-1.0 µg/ml) or Pokeweed mitogen (PWM) (5 mg/ml) (Sigma-Aldrich) in medium. Activation was measured by blast transformation (day 7) and cell surface markers according to FASCIA, using the methods as described in Svahn et al. J. Immunol. Methods, 2003, 277(1-2):17-25.

PCR Assay

Tumour samples were stored in RNA-later (Ambion, Austin, TX, USA) and extracted for DNA by DNAeasy Blood and Tissue kit (Qiagen). Primers (see Camargo et al., J. Virol. Methods 2011, 178(1-2), 68-74, and Sahiner et al., Diagn. Microbiol. Infect. Dis. 2014, 80(1), 43-9) were used for detection of the L1-region of HPV Type 16 (HPV16) and HPV Type 18 (HPV18). HPV18 DNA extracted from HeLa cells and HPV16 DNA (Advanced Biotechnologies) were used as positive controls. PCR assay was performed by Bio-Rad T100 following a standard PCR protocol.

Example 4:1: HPV Classification of Tumours

DNA was extracted from 5 available tumours (for patients 7 to 11) and analysed by PCR using HPV primers for the L1 gene from the most common disease-causing strains: HPV 16 and 18. In samples from 2 of the 5 tested patients HPV virus was detected (patients 8 and 9). The observed frequency of 40% was comparable with the reported frequency in the literature of 46.3% (Tornesello M L, et al., Int. J. Cancer, 2008, 122:132-137).

Example 4:2: Immunophenotyping of LNs

Single cell suspensions obtained from tumour, lymph nodes and peripheral blood were analysed by FACS. The proportion of different lymphocyte population in LNs varied between the patients and they are shown in Table 5.

TABLE 5

| Patient No. | Average % CD4+ | Average % CD8+ | Average CD4/CD8 | Average % CD19+ | Average % CD56+ | HPV |
|---|---|---|---|---|---|---|
| 1 | 43.9 | 7.87 | 6.11 | 38 | 5.2 | ND |
| 2 | 21.40 | 4.97 | 4.46 | 52.67 | 0.50 | ND |
| 3 | 49.9 | 20 | 2.57 | 41.25 | 25.4 | ND |
| 4 | 68.4 | 13.95 | 4.94 | 43.35 | 1.5 | ND |
| 5 | 69.05 | 5 | 13.81 | 15.05 | 0.6 | ND |
| 6 | 59.57 | 7.37 | 8.53 | 21.77 | 0.83 | ND |
| 7 | 81.30 | 3.60 | 19.92 | 6.67 | 0.43 | No |

TABLE 5-continued

| Patient No. | Average % CD4+ | Average % CD8+ | Average CD4/CD8 | Average % CD19+ | Average % CD56+ | HPV |
|---|---|---|---|---|---|---|
| 8 | 74 | 11.7 | 5.60 | 12.4 | 2.4 | Yes |
| 9 | 38.9 | 2.55 | 15.39 | 33.5 | 1.25 | Yes |
| 10 | 29.33 | 39.43 | 0.75 | 20.57 | 12.00 | No |
| 11 | 66.67 | 5.57 | 11.97 | 18.83 | 0.80 | No |

(ND = Not determined)

It is seen that the average fraction of CD4+ T-cells in LNs was between 21-81% and for CD8+ T-cells was 2.5-39%.

Next, the CD4/CD8 ratios between LN and peripheral blood were compared. There was a significant difference (p=0.0009) in the CD4+/CD8+ ratios between PBMCs and LNs: the CD4+/CD8+ ratio in PBMCs was 2.5 compared to 10 in LNs. This demonstrates expansion of CD4+ T-cells in LNs.

Figure 4:
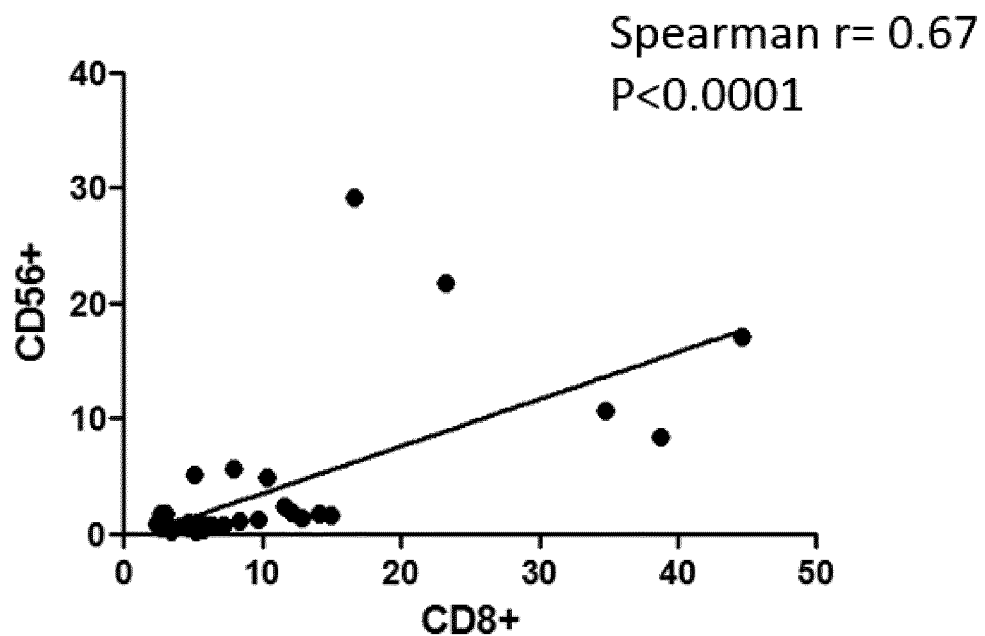
FIG. 4A shows a correlation between CD8+ T-cells and CD56+ expressing lymphocytes in lymph nodes of the penile cancer patients in the study.
FIG. 4B shows an inverse correlation between the fraction of CD19+ B cells and CD4+ T-cells in lymph nodes of the penile cancer patients in the study.
FIG. 4C shows, an inverse correlation between the fraction of CD19+ B cells and the CD4+/CD8+ ratio in lymph nodes of the penile cancer patients in the study.
Figure 4:
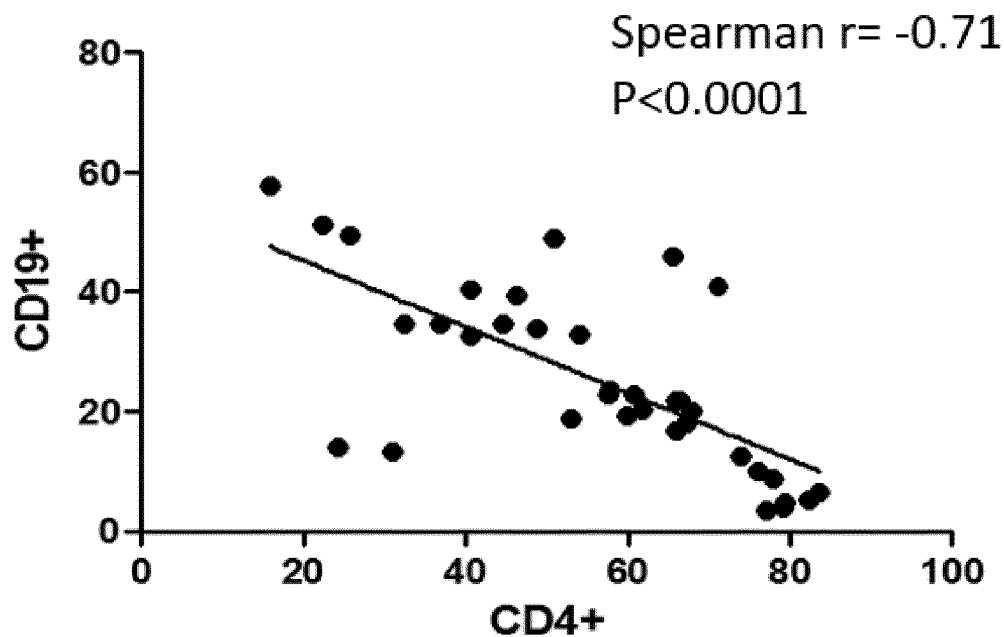
Figure 4:
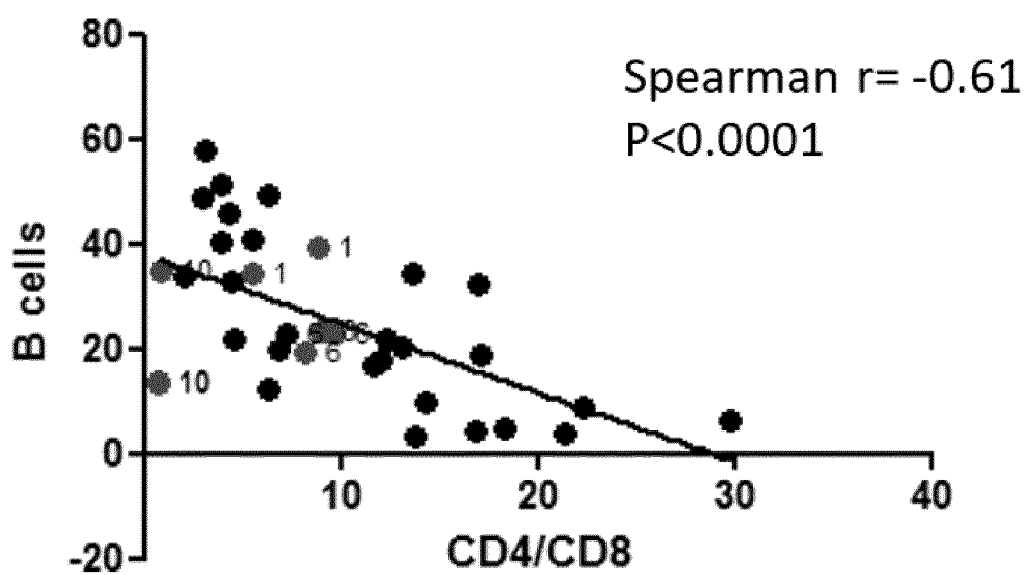

The lymphocyte populations were compared and a significant correlation between CD8+ T-cells and CD56+ expressing lymphocytes was found (Spearman r=0.67, p<0.0001), (FIG. 4A). Furthermore, an inverse correlation between the fraction of CD19+ B cells and CD4+ T-cells was also found (Spearman r=−0.71, p<0.0001) (FIG. 4B). In addition, an inverse correlation between the fraction of CD19+ B cells and the CD4+/CD8+ ratio (Spearman r=−0.61, p<0.0001) (FIG. 4C) was found. It was noted that patients who died from penile cancer within two years from diagnosis (patients 1, 6, 10) displayed low CD4+/CD8+ ratio and/or low CD19+ cells.

Figure 5:
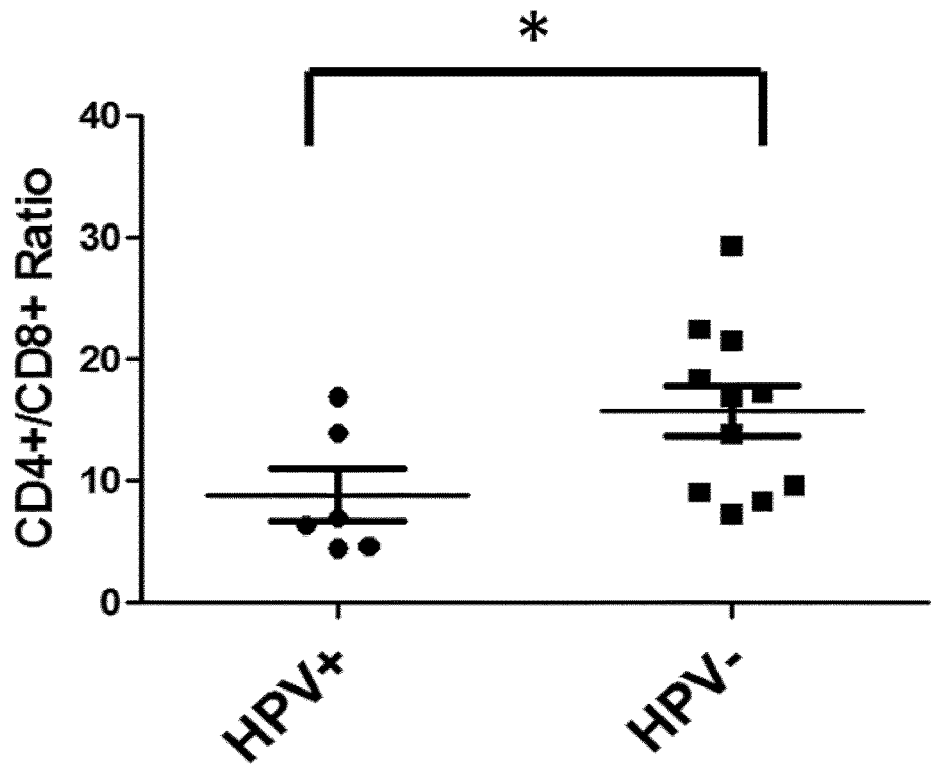
FIG. 5 shows the CD4+/CD8+ ratios in lymph nodes according to respective HPV-status of penile cancer patients in the study.

The CD4+/CD8+ ratios in LNs according to respective HPV-status was analysed. The inventors found a significantly decreased (p<0.05) CD4+/CD8+ ratio in LNs derived from HPV positive patients. These results suggest that there was a relative increase in HPV recognizing CD8+ T-cells in HPV patients (FIG. 5).

Example 4:3: Tumour and Reactivity in Draining Lymph Nodes

T-cell responses were tested against a tumour lysis extract. In 13 available LNs from six patients, immune responses towards tumour extract were investigated by FASCIA, as described in Marits et al. Clin. Immunol., 2014, 153(2):332-342.

Figure 6:
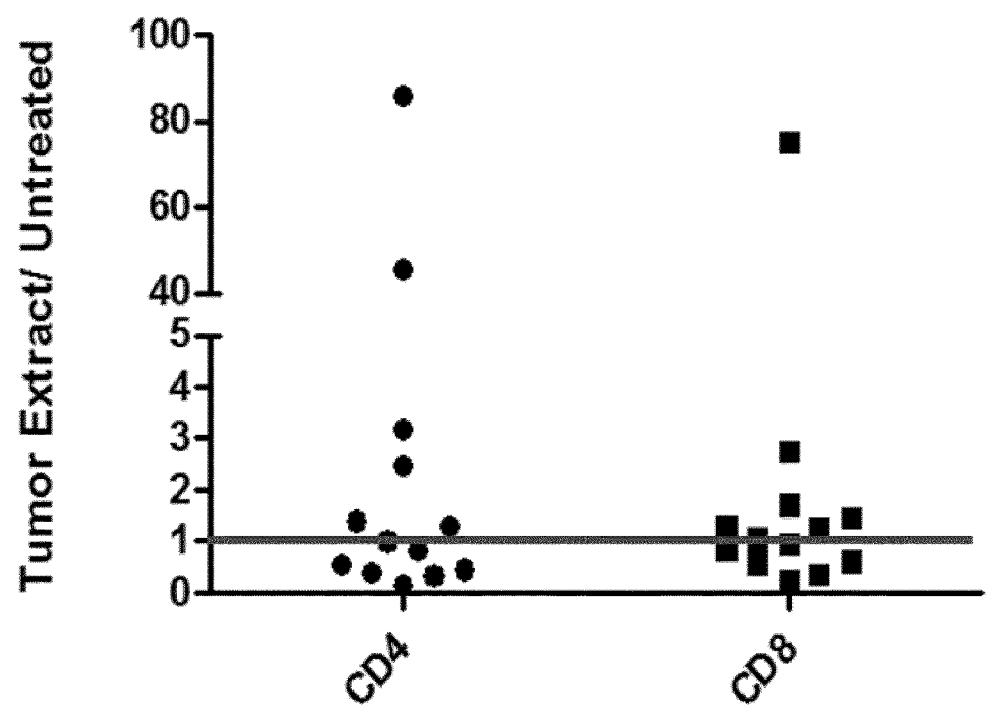
FIG. 6 shows the ratio of the level of blast transformation response for CD4+ and CD8+ T-cells after exposure to tumour extract from penile cancer patients in the study.

CD4+ T-cell blast transformation was observed as a response in 6/13 LNs (46%) to tumour extract. Correspondingly, CD8+ T-cell blast responses were seen in 7/13 (54%) LNs (FIG. 6). In total an immune response (either CD4+ or CD8+) was observed in 9 out of 13 tested LNs by FASCIA using autologous tumour extract as antigen (69%). Thus, 5 out of 6 tested patients (83%) demonstrated a T-cell recognition of a tumour associated antigen present in autologous tumour extract.

Example 4:4: HPV Reactivity in Draining Lymph Nodes

Both Gardasil® and tumour extract stimulation was carried out with LN cells from the two HPV positive patients (patient No 8 and 9). When tumour extract was used as antigen for stimulation, a small T-cell response (for both CD4+ T-cells and CD8+ T-cells) in the FASCIA was noted with PBMC cells (see FIG. 7 in which the data for a PBMC sample from patient No 8 are shown). However, a strong response (for both CD4+ and CD8+ T-cells) was found in PBMCs and in LN cells in the HPV positive patients when Gardasil® was used as the antigen for stimulation (see FIG. 7 in which the data for samples from PBMCs and two LNs from patient No 8 are shown).

Both HPV-positive patients (patients 8 and 9) responded to Gardasil® and to tumour extract. Only absent or very weak responses towards Gardasil® were noted in HPV-negative patients, demonstrating that L1 protein responses were restricted to HPV-positive patients.

In a dose response assay, Gardasil® was added to the cell culture at levels from 0.1-1 µg/ml and blast transformation was evaluated on day 7. The LN-derived lymphocytes from HPV-positive patient 9 responded in a dose dependent manner against Gardasil® (FIG. 8A), where 1 µg/ml of Gardasil® resulted in a 5-fold increase in response compared to 0.3 µg/ml of added antigen.

Figure 8:
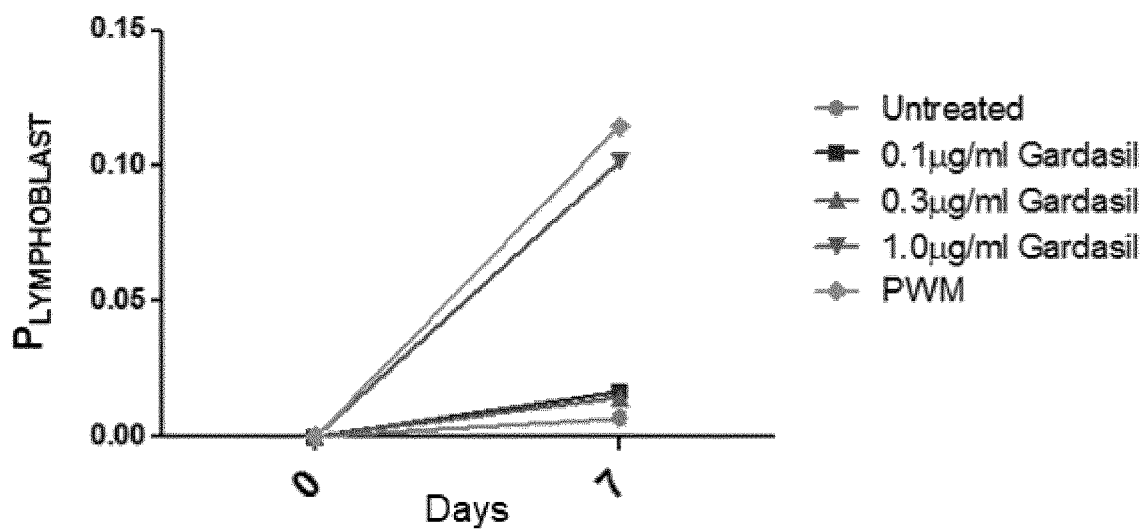
FIG. 8A shows the results of a dose response assay of blast transformation after Gardasil® was added at various levels to lymph node cell cultures from HPV positive patients.
FIG. 8B shows the cell surface expression of the T-cell activation marker HLA-DR (Human Leukocyte Antigen—DR Isotype) in cell cultures after Gardasil® was added at various levels to lymph node cell cultures from HPV positive patients.
Figure 8:
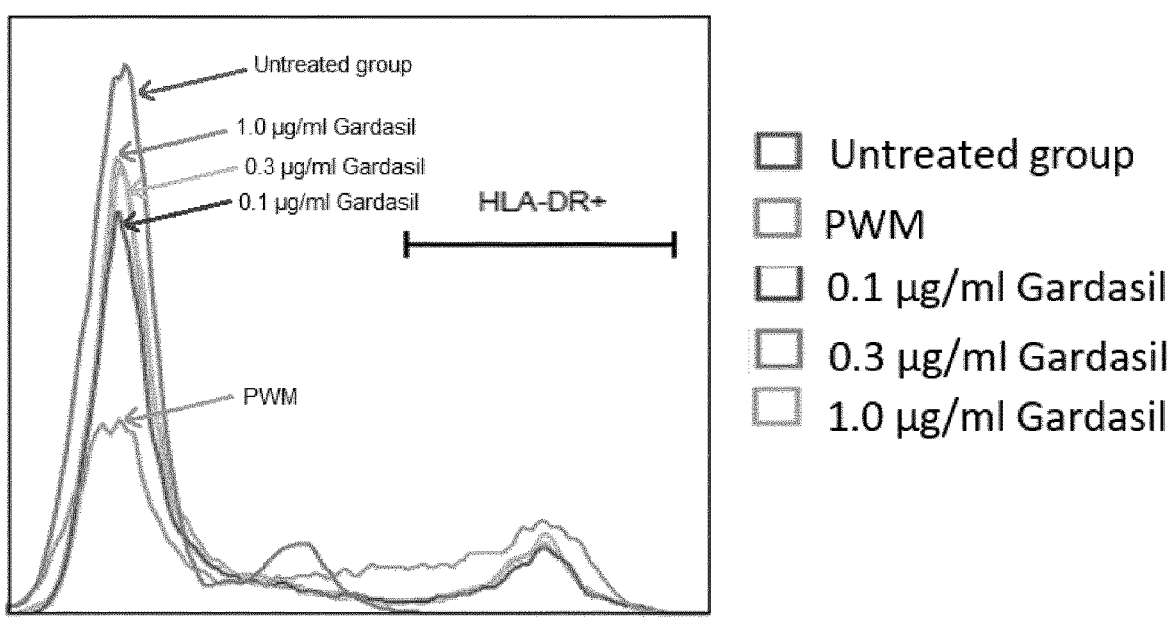

When the cell surface expression of the T-cell activation marker HLA-DR (Human Leukocyte Antigen—DR isotype) was investigated, a 10-fold increase from unstimulated to Gardasil® stimulated group was seen, substantiating that there was Gardasil® dependent T-cell activation (FIG. 8B).

SUMMARY

The present inventors have observed tumour antigen specific T-cell responses in LNs from patients with penile cancer for the first time. Moreover, HPV-positive patients demonstrated T-cell responses against the L1 components of the Gardasil® vaccine.

The distribution of lymphocytes varied, but a significant increase in the CD4+/CD8+ ratios in LNs compared to PBMCs was detected (FIG. 4B) indicating expansion of CD4+ T-cells in LNs.

The present inventors also found that HPV infected penile cancer patients displayed a significant decrease of the CD4+/CD8+ ratio in LNs, indicating activation and expansion of HPV recognizing CD8+ T-cells (FIG. 5).

Although, CD56+ is known as a Natural Killer (NK) lymphocyte cell marker, CD56 is also expressed on activated cytotoxic CD8+ T-cells (Pittet et al., J. Immunol. 2000, 1, 164(3), 1148-1152), indicating that LNs contain an increased number of activated CD8+ T-cells, further demonstrating their state of activation (FIG. 4A). Additionally, an activation of CD4+ T-cells in LNs responding to the HPV-L1 proteins from HPV 16 and/or 18 present in Gardasil® was observed, further supporting the notion of a HPV specific immune response.

Figure 7:
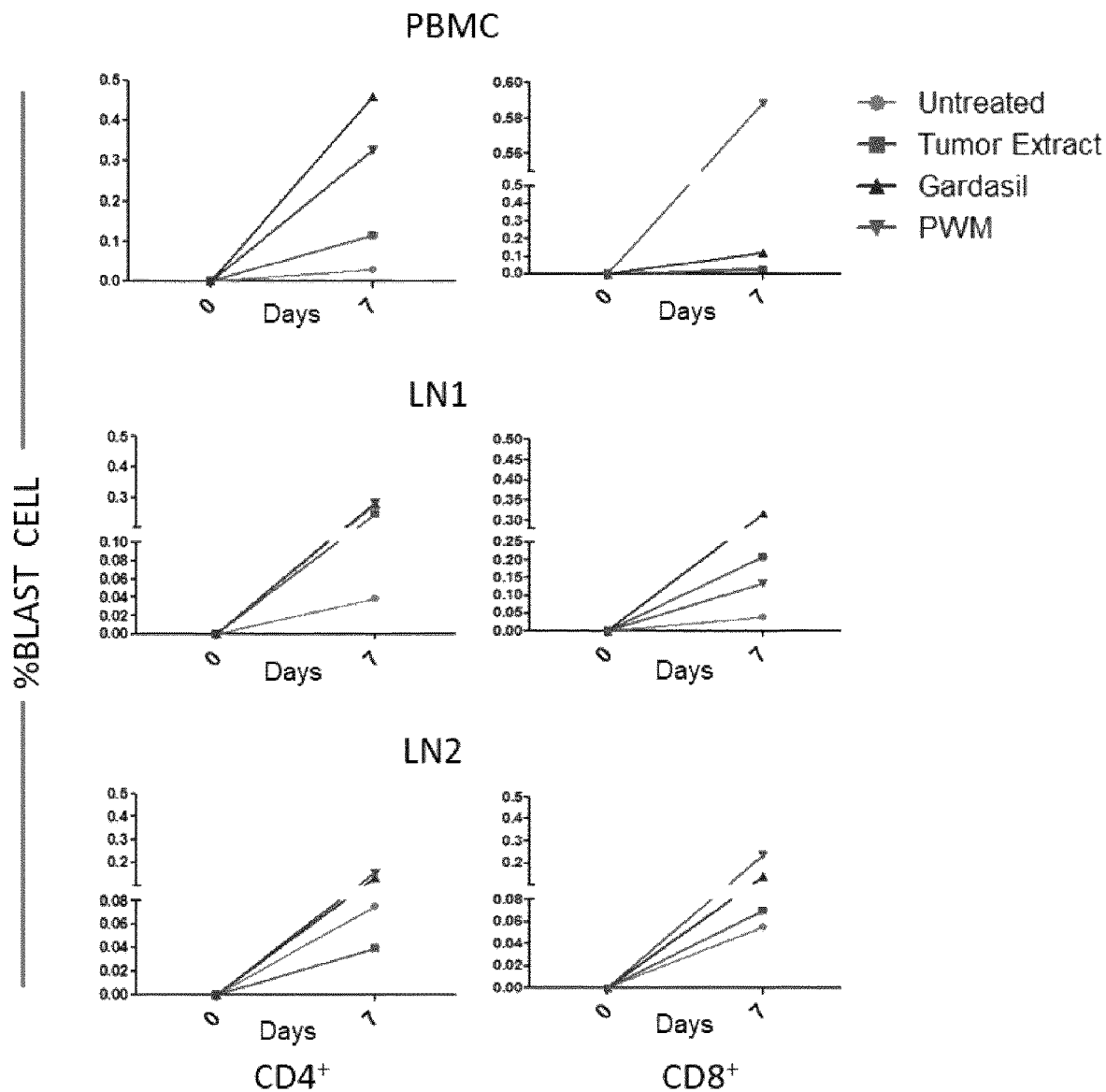
FIG. 7 shows the % cell blast cell response in the FASCIA assay for lymphocytes obtained PBMCs and lymph nodes of an HPV-positive penile cancer patient under various stimulation conditions.

The FASCIA assay used the addition of tumour homogenate or L1 proteins from HPV 16 and/or 18 present in Gardasil®, and the length of the peptides or the exogenously provided homogenate promotes presentation in the MHC class II pocket and hence stimulation of CD4+ T-cells. The activation of CD8+ T-cells against Gardasil® was poor in PBMC cultures, but they responded significantly in LN cultures (FIG. 7). This suggests that cross presentation is present in LN cultures where specialized dendritic cells may have the capacity to load MHC class I molecule for CD8+ T cell activation (Bonaccorsi et al., Crit. Rev. Immunol., 2015, 35(5), 349-364).

The increased T-cell proliferation to Gardasil® compared to tumour extract suggests that Gardasil® contains higher concentrations of pure antigens compared to autologous tumour extracts. The demonstration of a dose-dependent response towards L1 proteins shows that Gardasil® is a useful source of antigen for expansion of HPV-specific T-cells in HPV-positive penile cancer patients. The expanded cells find use in adoptive T-cell therapy.

Example 5: Ex-Vivo T-Cell Expansion Using Particles Coupled to the Model Virus Antigen CMV pp65

(i) Preparation of the CMV Pp65 Construct Coupled Phagocytosable Particles (Herein Referred to as "CMV-Particles"):

The phagocytosable particles (Sera-Mag Speed Beads Carboxylate-Modified magnetic particles, GE Healthcare) were coupled with the CMV pp65 construct (SEQ ID NO. 15). To remove endotoxin, the phagocytosable particles were washed five times with a 2M sodium hydroxide buffer and subsequently resuspended in sterile PBS.

Figure 9:
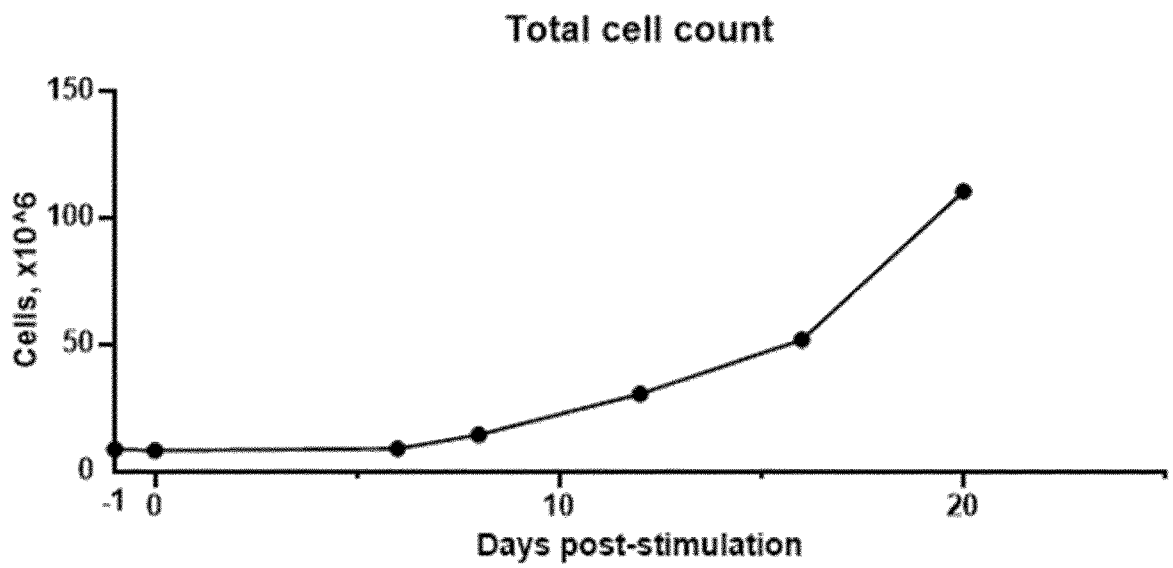
FIG. 9A shows that the increase in the number of cells over 20 days in the PBMC culture after stimulation with model virus antigen particle (i.e. CMV-particles).
FIG. 9B shows that the viability of the cells in the PBMC culture remained substantially constant over the 20 days of culturing.
Figure 9:
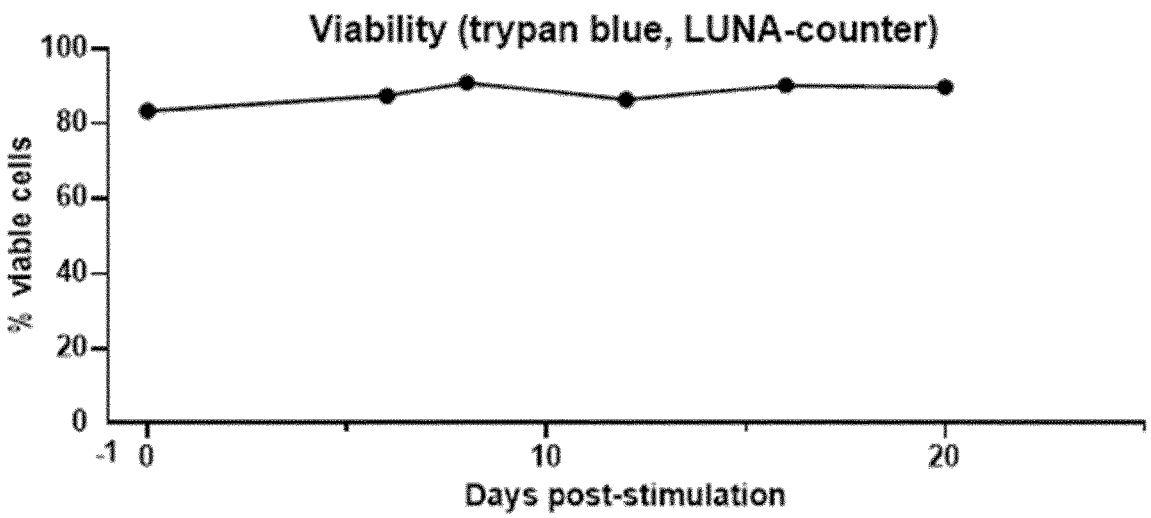

(ii) Incubation of CMV-Particles with PBMCs:

Peripheral blood mononuclear cells (PBMCs) from a CMV positive donor, isolated via standard ficoll-based density gradient centrifugation were cultured together with the CMV-particles. PBMCs were seeded in cell culture media at approximately 2 to 5 million cells/ml. On Day 0, the CMV-particles were added to the culture at a ratio of particles to antigen-presenting cells of between 1:1 and 1:20. Cells were cultured for 20 days and the cell density was maintained at approximately 2 to 5 million cells/ml throughout the entire culture procedure. At appropriate intervals during the culture procedure, the culture media was changed and the cell number and the cell viability assessed. Cell viability was assessed using a Trypan blue exclusion assay (Saveen Werner). Cell number and viable cells were counted using a LUNA™ Automated Cell Counter following the manufacture's guidelines. After 20 day, the cell number in the culture had expanded approximately 13 times (FIG. 9A), and approximately 80% of the cells in the culture were viable (FIG. 9B). Notably, the percentage of viable cells remained substantially constant (at around 80%) throughout the entire culturing procedure.

(iv) Immunophenotyping of PMBCs Following Addition of CMV-Particles

The viability and phenotype of the cultured PBMCs were assessed using FACS analysis. PBMCs that did not undergo stimulation with CMV particles were also analysed as a control (referred to as PBMC baseline). FACS was performed using a LSRFORTESSA (Becton Dickinson) and data were analysed using the FACS DIVA software (Becton Dickinson). PBMC samples were removed from the culture and washed in PBS containing 2% FCS and 0.05% Na $N_3$ (FACS-buffer). For investigating subtypes of lymphocytes and their functions, staining was performed with the following fluorophore conjugated antibodies: Blue Live/Dead stain, anti-CD4 Pacific-Blue, anti-CD8 APC, and anti-CD3 (Becton Dickinson). The FACS gating used in the analysis is shown in FIG. 10A.

Figure 10:
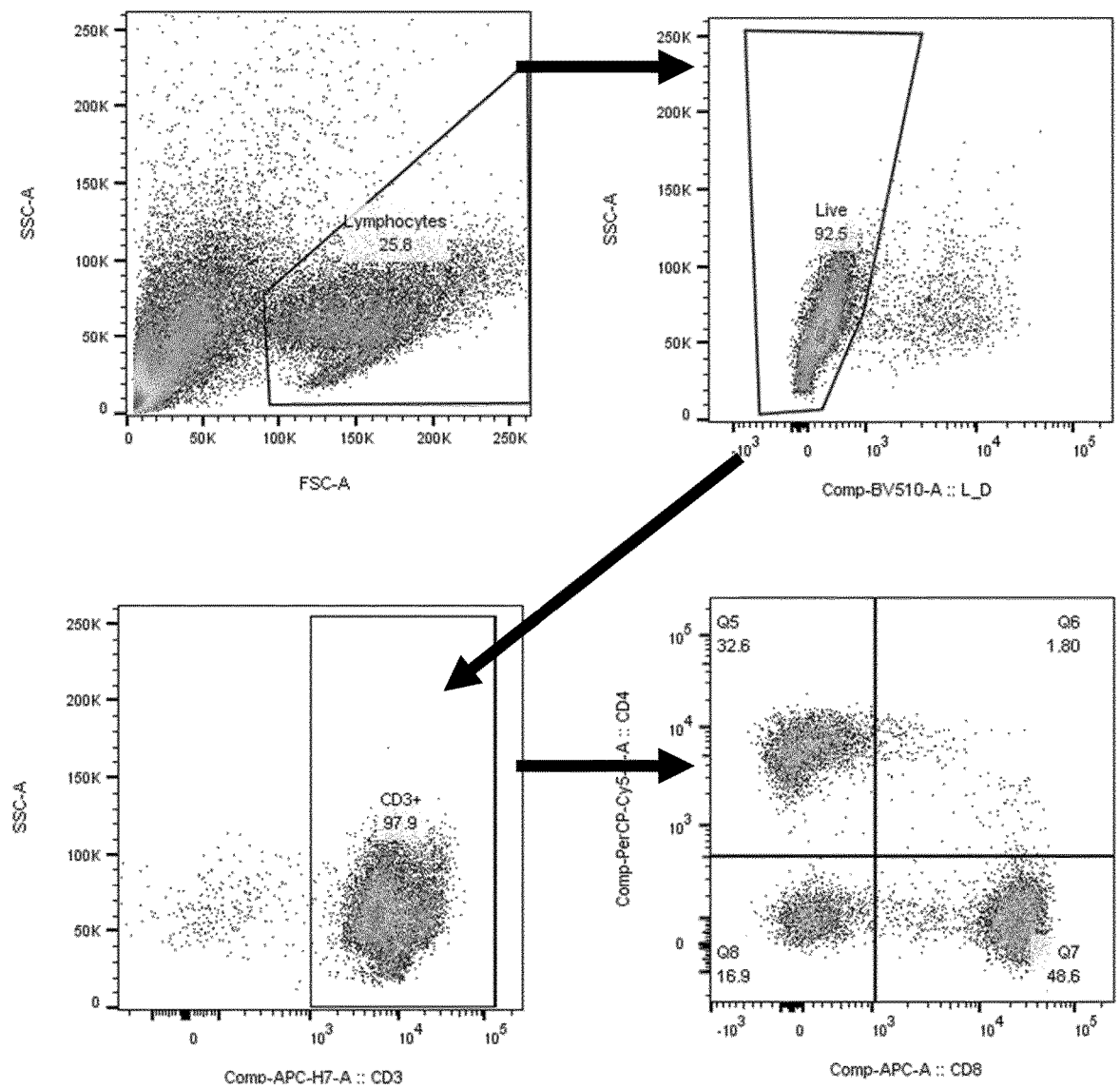
FIG. 10A shows the FACS gating strategy used to determine the viability and phenotype of the cells present in the PBMC culture after stimulation with the CMV-particles.
FIG. 10B shows the percentage of cells in the PBMC culture that are CD3+ cells at Day 0 and Day 19.
FIGS. 10C and 10D show the proportion of the cells in the PBMC culture that are CD4+, CD8+ cells, CD4+/CD8+ cells (Double Positive cells—DP) or CD4−/CD8− (Double Negative cells—DN) at Day 0 (CD4 CD8 baseline) and Day 19 (CD4 CD8 d19), respectively.
Figure 10:
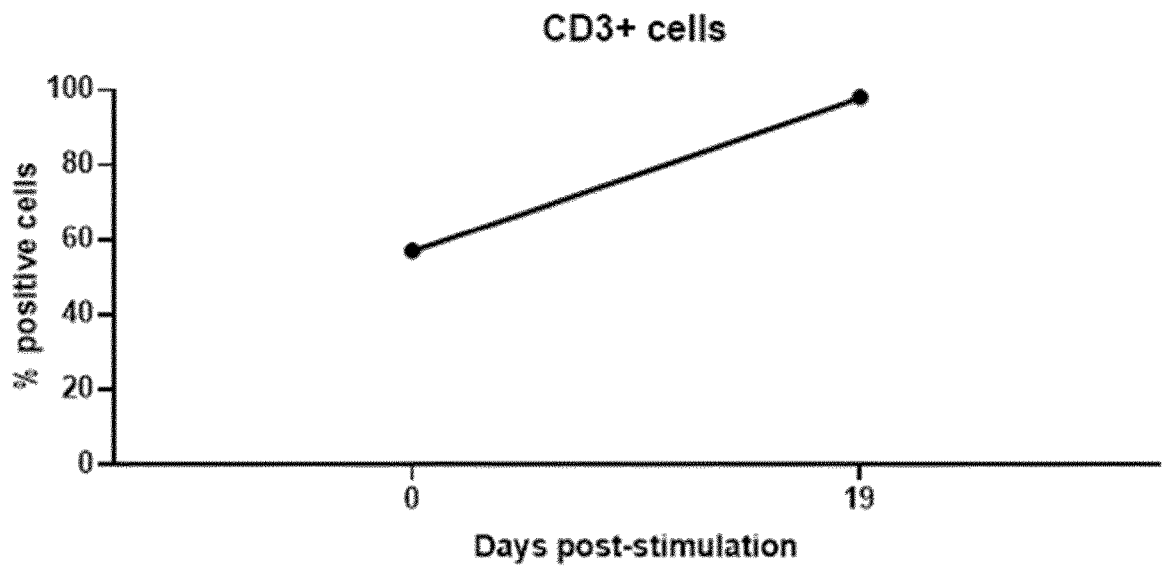
Figure 10:
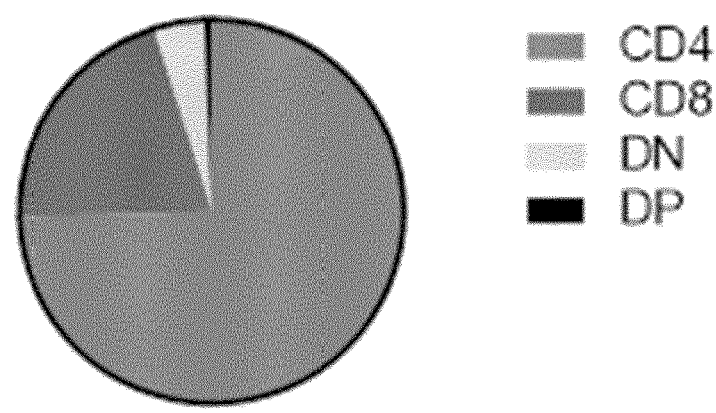
Figure 10:
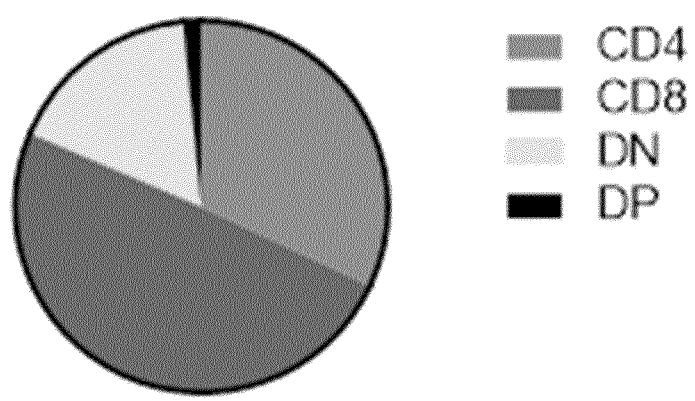

The FACS analysis shows that after 19 days of culturing the PBMC cells with the CMV-particles, 98% of the cells in the culture were CD3+ cells, of which 49% were CD8+ cells and 33% were CD4 cells (FIGS. 10B, C and D).

(iv) Assessment of T-Cell Stimulation

The ability of the CMV-particles to stimulate T-cells and hence promote T-cell expansion was also assessed by measuring the release of IFNγ from the expanded T-cells using a FluoroSpot assay (Mabtech, Sweden). Cells ("Expanded PMBCs") were removed from the culture 19 days after addition of the CMV-particles and re-exposed to the same type of CMV-particles as used in the expansion protocol, or exposed to uncoupled beads (phagocytosable particles without an antigen attached), media, or albumin-binding domain (ABD). IFNγ release from these cells was then analysed using the FluoroSpot assay, which was used in accordance with the manufacture's guidelines. As a negative control, a PBMC sample that had not undergone ex-vivo expansion using the CMV-particles ("PBMC Baseline") was exposed to CMV-particles, uncoupled beads, media only or albumin-binding domain (ABD). Wells containing cells that released high levels of IFN-γ displayed a higher level of fluorescence. To show that the cell culture contained T-cells, samples of the Expanded PMBCs and PBMC Baseline cells were also exposed to a fluorescently labelled anti-CD3 antibody (shown as "a-CD3" in FIG. 11A).

Results

Figure 11A:
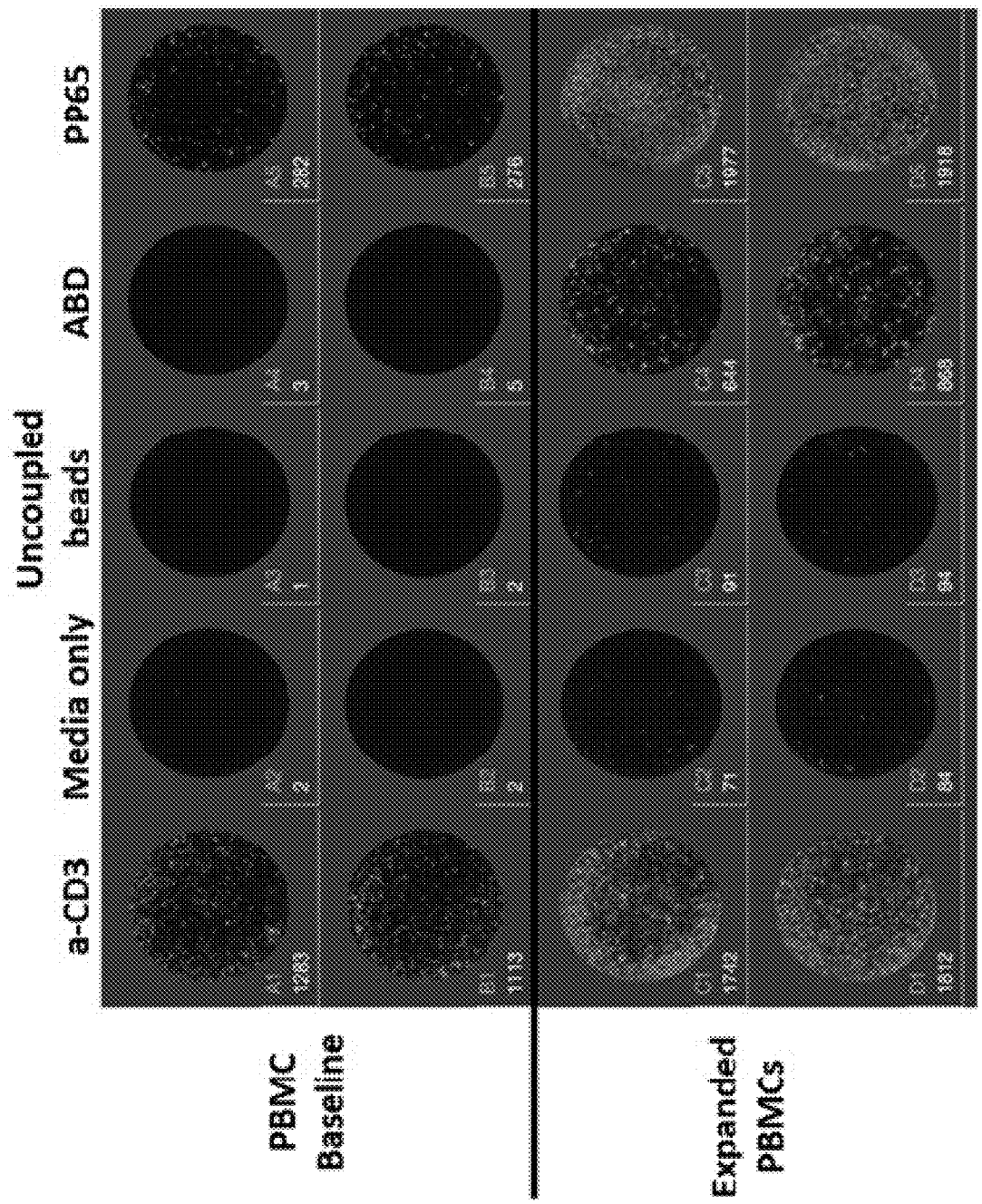
FIG. 11A shows a fluorescent read of a FluoroSpot assay plate containing PBMCs that have not undergone ex-vivo expansion using the CMV-particles (referred to herein as "PBMC baseline") and PBMCs from a culture that has been expanded using the CMV-particles (referred to as "Expanded PBMCs"). Both the PBMC baseline and the Expanded PBMCs were exposed to uncoupled beads, fresh media, albumin-binding domain (ABD), or CMV-particles prior to analysis of IFNγ release using the FluoroSpot assay. Wells containing cells that released high levels of IFN-γ displayed a higher level of fluorescence. As a control, a fluorescently tagged anti-CD3 antibody was used (first column, a-CD3).
Figure 11:
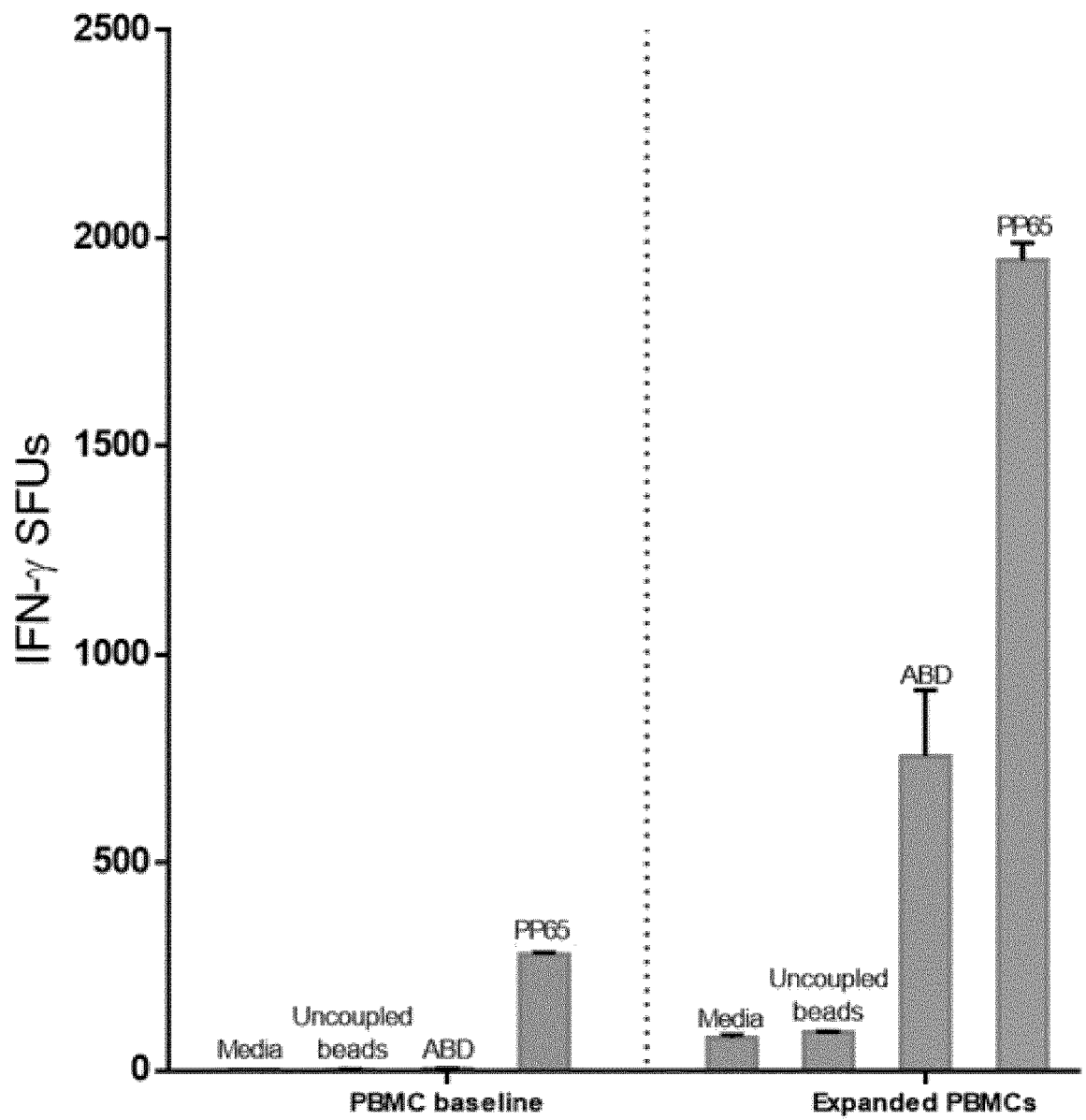
FIG. 11B shows a graphical representation of the fluorescence/IFNγ release shown in FIG. 11A.

As shown in FIGS. 11A and 11B, the expanded T-cells ("Expanded PBMCs") showed notably higher levels of IFNγ release compared to the cells exposed to uncoupled beads, media only or albumin-binding domain (ABD). Only a low level of IFNγ release was observed for the PBMC Baseline cells incubated with the CMV-particles prior to analysis in the FluoroSpot assay. This data indicates that the CMV-particles enriched the PBMCs taken from the CMV-positive donor with CMV-specific T-cells.

Example 6: Phagocytosable Particle Toxicity and Biodistribution Study

Materials and Method

Particles used in study: Sera-Mag SpeedBead Carboxylate-Modified Magnetic Particles (Hydrophilic). These particles are supplied by GE Healthcare Life Sciences (Particle Lot/Batch Number GE: 16807675, concentration: 2.3% solids (g/100 g) (corresponding to 10 mg Fe/mL) in Dulbecco's phosphate buffered saline, pH 7.1). The particles are stored prior to use at 2-8° C.

Animal details: Rats, Wistar. On arrival to the study location, the rats have an approximate weight of 250 g. Rats are acclimatised for a minimum of 5 days prior to the start of the study. The rats are kept in individually ventilated cages (type IVC 4) at +22° C.±3° C., a humidity of 50%±20% and with 12-hour light/12-hour dark cycles. Food and water are available ad libitum. There are three rats per cage.

Study 1):

Five female Wistar rats are used in the pilot study. Rat #1 is subjected to intravenous (IV) injection with the maximum feasible concentration of particle (concentration equivalent to 50 mg/kg iron at 5 mL/kg), after which the rat is placed in a computed tomography (CT) camera for acquisition of an image. Intravenous injection is performed as slowly as possible. If a toxic response is evident, particles are delivered to the remaining rats by slow infusion over a period of 20 minute (max 20 mL/kg). The particle concentration delivered to the rats is titrated until a maximum tolerated dose is identified. A rat that has not received a dose of particles is used as a negative control and for acquisition of a background CT scan.

Following IV injection/infusion of the particles, the rats are anaesthetised with isoflurane and ophthalmic ointment is placed on the eyes to prevent dehydration. Rats are then placed on the heated bed of a CT instrument, where inhalation anaesthesia is maintained. Vital parameters (pulse and respiration) are monitored during the course of the experiment using a respiration sensor and rectal thermometer. Rats are inserted into the CT camera, where a picture is acquired over the course of about 20 minutes. Health status following IV injection of particles is documented to assess possible toxic reactions, and a whole-body CT image is used to assess particle visibility and to determine the location of particles following injection. Following acquisition of a CT image, the rats are euthanised.

Study 2):

A further study is performed using twelve rats to identify the rate of particle elimination. All rats receive an IV injection of the particles at a dose identified in the pilot study. Immediately after administration of the particles, the rats are placed in a CT camera. The rats are thereafter monitored in the CT camera at 24 h, 3 days, 7 days, 14 days and 1 month after administration. At each time point, two rats are euthanised for excision of organs for histopathological analysis. The rats are monitored for changes in health status and body weights 24 h, 3 days and 7 days after administered and once weekly thereafter.

Example 7: Exemplification of Phagocytosable Particle Sterilisation Protocol Using *Bacillus subtilis*

This experiment was performed under sterile conditions in a laminar air flow (LAF) safety cabinet. Phagocytosable particles comprising a core (Sera-Mag SpeedBeads Carboxylate-Modified magnetic particles, GE Healthcare) attached to a neoantigen construct were washed four times with high concentration alkaline solution (2M to 5M NaOH). After the first wash, the phagocytosable particles were transferred to a new sterile tube, the supernatant was removed, and a second volume of alkaline solution was added. Phagocytosable particles were sonicated for 10 minutes in a sonication bath, and then incubated for 30 minutes with end-over-end rotation in the same alkali solution. This process was repeated a further two times, followed by four washes with sterile Dulbecco-modifies PBS.

Effectiveness of the NaOH treatment protocol was evaluated by spiking phagocytosable particles (Sera-Mag SpeedBeads Carboxylate-Modified magnetic particles, without attached neoantigen) with a high load (>1.2 CFU) of *Bacillus subtilis* subsp. *spizizenii* (ATCC® 6633™ Epower 106 CFU), followed by the above described NaOH treatment protocol. After NaOH treatment, both full bead suspension and supernatant from non-treated (positive control) vs 5M or 2M NaOH treated samples were plated on nutrient agar in the absence of antibiotics, and incubated at 37° C. overnight (>16 hours).

Results

Both 5M and 2M NaOH treatment effectively abolished bacterial growth, whereas colonies of *Bacillus subtilis* subsp. *spizizenii* were abundantly growing in the absence of washes. In conclusion, both the 2M and 5 M NaOH treatments were highly effective at removing an artificially high bioburden load from the phagocytosable particles.

The invention claimed is:

1. A method for the expansion of human papillomavirus (HPV) immunogen specific T-cells, comprising the steps of:
   i. contacting a phagocytosable particle comprising a core and an HPV immunogen tightly associated to the core with antigen presenting cells (APCs) in vitro, and under conditions allowing phagocytosis of the HPV immunogen by the APCs, wherein:
      (a) the core is paramagnetic or superparamagnetic and has a largest dimension of 0.5 µm to 2.5 µm; and
      (b) the HPV immunogen has an amino acid sequence that corresponds to the amino acid sequence of an HPV protein, or has an amino acid sequence that corresponds to an amino acid sequence of a part of an HPV protein; and
   contacting T-cells that have been harvested from a subject with the APCs from step i) in vitro, and under conditions allowing specific activation of HPV immunogen specific T-cells.

2. The method of claim 1, n wherein the T-cells have been harvested from a subject having an HPV positive cancer.

3. The method of claim 1, wherein the T-cells have been harvested from a tumour draining lymph node in the subject or from a PBMC sample derived from the subject.

4. The method of claim 1, wherein the T-cells have been harvested from a PBMC sample derived from the subject, and wherein the subject is one that has previously received a dose of an HPV vaccine.

5. The method of claim 1, wherein the HPV protein is one necessary for viral replication or an HPV coat protein.

6. The method of claim 1, wherein the HPV protein is an HPV coat protein L1 selected from the group consisting of HPV types 6, 11, 16, 18, 31, 33, 45, 52 and 58.

7. The method of claim 1, wherein the HPV immunogen is covalently attached to the core.

8. The method of claim 1, wherein the core comprises polystyrene.

9. The method of claim 1, wherein the phagocytosable particle comprises two or more HPV immunogens.

10. The method of claim 1, wherein the phagocytosable particle comprises two or more different kinds of HPV immunogen.

11. The method of claim 4, wherein the HPV vaccine comprises HPV coat protein L1 derived from HPV types 6, 11, 16 and 18.

12. The method of claim 4, wherein the HPV vaccine comprises HPV coat protein L1 derived from HPV types 6, 11, 16, 18, 31, 33, 45, 52 and 58.

13. The method of claim 4, wherein the HPV vaccine comprises HPV coat protein L1 derived from HPV types 6 and 11.

14. The method of claim 9, wherein the HPV immunogens comprise HPV coat protein L1 derived from HPV types 6, 11, 16 and 18.

15. The method of claim 9, wherein the HPV immunogens comprise HPV coat protein L1 derived from HPV types 6, 11, 16, 18, 31, 33, 45, 52 and 58.

16. The method of claim 9, wherein the HPV immunogens comprise HPV coat protein L1 derived from HPV types 6 and 11.

17. The method of claim 1, wherein the amino acid of the HPV immunogen comprises SEQ ID NO: 1, SEQ ID NO:2, SEQ ID NO:3, SEQ ID NO:4, or SEQ ID NO:5.

* * * * *